United States Patent
Carswell et al.

(10) Patent No.: US 11,020,396 B2
(45) Date of Patent: Jun. 1, 2021

(54) PYRIMIDINONE DERIVATIVES AS CDC7 INHIBITORS

(71) Applicant: Cancer Research Technology Limited, London (GB)

(72) Inventors: Emma L. Carswell, Cambridge (GB); Mark David Charles, Cambridge (GB); Chukuemeka Tennyson Ekwuru, Cambridge (GB); Frederic Elustondo, Bordeaux (FR); Katherine M. Fowler, Cambridge (GB); Gregory R. Ott, West Chester, PA (US); Jonathan R. Roffey, Cambridge (GB); Joanna L. Brookfield, Cambridge (GB); Daniel James Ford, Sydney (AU); Mathew L. Calder, Cambridge (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 16/348,073

(22) PCT Filed: Nov. 7, 2017

(86) PCT No.: PCT/GB2017/053336
§ 371 (c)(1),
(2) Date: May 7, 2019

(87) PCT Pub. No.: WO2018/087527
PCT Pub. Date: May 17, 2018

(65) Prior Publication Data
US 2019/0336502 A1    Nov. 7, 2019

(30) Foreign Application Priority Data
Nov. 8, 2016 (GB) .................... 1618845

(51) Int. Cl.
| | | |
|---|---|---|
| *C07D 403/14* | (2006.01) |
| *A61K 31/506* | (2006.01) |
| *A61K 31/437* | (2006.01) |
| *A61K 31/551* | (2006.01) |
| *C07D 413/14* | (2006.01) |
| *C07D 417/14* | (2006.01) |
| *C07D 471/04* | (2006.01) |

(52) U.S. Cl.
CPC .......... *A61K 31/506* (2013.01); *A61K 31/437* (2013.01); *A61K 31/551* (2013.01); *C07D 403/14* (2013.01); *C07D 413/14* (2013.01); *C07D 417/14* (2013.01); *C07D 471/04* (2013.01)

(58) Field of Classification Search
CPC .................................................. C07D 403/14
See application file for complete search history.

(56) References Cited

U.S. PATENT DOCUMENTS

2015/0158882 A1    6/2015    Homma et al.

FOREIGN PATENT DOCUMENTS

| WO | WO-2007/124288 A1 | 11/2007 |
| WO | WO-2009/086264 A1 | 7/2009 |
| WO | WO-2011/133388 A1 | 10/2011 |
| WO | WO-2016/198663 A1 | 12/2016 |
| WO | WO-2017/133667 A1 | 8/2017 |
| WO | WO-2017/133670 A1 | 8/2017 |

OTHER PUBLICATIONS

McMahon et al. (2000).*
Pinedo et al. (2000).*
International Search Report and Written Opinion for International Application No. PCT/GB2017/053336 dated Dec. 11, 2017.
UK Search Report for Application No. GB1618845.0 dated Aug. 17, 2017.
Woods et al., "Aminopyrimidinone Cdc7 Kinase Inhibitors," Bioorganic & Medicinal Chemistry Letters, 22(5):1940-1943 (2012).

* cited by examiner

*Primary Examiner* — Paul V Ward
(74) *Attorney, Agent, or Firm* — Foley Hoag LLP; David P. Halstead

(57) ABSTRACT

The present invention relates to compounds of formula I as defined herein, and salts and solvates thereof, that function as inhibitors of cell division cycle 7 (Cdc7) kinase enzyme activity. The present invention also relates to pharmaceutical compositions comprising them, and to their use in the treatment of proliferative disorders, such as cancer, as well as other diseases or conditions in which Cdc7 kinase activity is implicated.

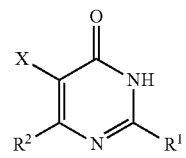

Formula I

20 Claims, No Drawings

PYRIMIDINONE DERIVATIVES AS CDC7 INHIBITORS

RELATED APPLICATIONS

This application is a § 371 national-stage application based on Patent Cooperation Treaty Application serial number PCT/GB17/53336, filed Nov. 7, 2017; which claims the benefit of priority to Great Britain Application No. 1618845.0, filed on Nov. 8, 2016.

INTRODUCTION

This application relates to compounds of Formula I as defined herein and salts or solvates thereof.

The compounds of Formula I and their salts have Cdc7 inhibitory activity, and may be used to treat diseases or conditions mediated, at least in part, by Cdc7.

The present application further provides pharmaceutical compositions comprising a compound of Formula I and/or a pharmaceutically acceptable salt or solvate thereof and an pharmaceutically acceptable excipient.

The present application also provides methods of treating a disease or condition mediated, at least in part, by Cdc7 in a subject in need thereof comprising administering to the subject a compound of Formula I and/or a pharmaceutically acceptable salt or solvate thereof.

BACKGROUND OF THE INVENTION

Eukaryotic cells divide by a directed, highly regulated step-wise process known as the cell cycle. DNA replication is an essential part of cell cycle progression and tight regulation ensures that DNA is replicated accurately only once during S-phase. In mammalian cells DNA replication is initiated at multiple sites (origins of replication). Numerous pre-replication complexes (pre-RC) form at origins of replication along each DNA strand during G1 to ensure that the whole genome is completely replicated in S-phase. The inactive pre-RC consists of the heterohexamer helicase complex Minichromosome maintenance 2-7 (MCM2-7), Cell division cycle 6 (Cdc6) and Chromatin licensing and DNA replication factor 1 (Cdt1) (Donaldson et al., 1998; Masai et al., 2002). Cell division cycle 7 (Cdc7) is a Ser/Thr kinase, which together with its regulatory partner Dumbbell former 4 (Dbf4), forms the active S-phase kinase complex, Dbf4 dependent kinase (DDK) (Kumagai et al., 1999; Jiang et al., 1999; Duncker et al., 2003). DDK is essential in controlling the initiation of DNA replication in combination with Cdk/cyclins by activation or licensing of the pre-RC; this activation involves phosphorylation of MCM2 and MCM4 (Kim 2003, Bousset et al., 1998, Takeda et al., 2001; Bruck et al., 2009; Francis et al., 2009; Sheu et al., 2006; Sheu et al., 2010). Cdc7 phosphorylates MCM2 at various sites, including Ser53 and Ser40 exclusively (Charych et al., 2008; Tsuji et al., 2006; Montagnoli et al., 2006; Cho et al., 2006). The phosphorylation of the amino-terminus of MCM4 by Cdc7 is also essential for replication, but the exact phoshorylation sites are unknown (Masai et al., 2006; Pereverzeva et al., 2000).

Cdc7 depletion by siRNA inhibits phosphorylation of MCM2 in both non-transformed primary fibroblasts and cancer cell lines, however non-transformed primary fibroblast cells arrest in G1 whereas cancer cells apoptose (Rodriguez-Acebes et al., 2010; Kulkarni et al., 2009., Montagnoli et al., 2004). The lack of cell death in normal cells is believed to be due to the induction of a functioning G1 checkpoint which is deficient in cancer cell lines. Thus, when Cdc7 is depleted, cancer cells enter a defective S-phase and undergo apoptosis due to checkpoint dysfunction (Tudzarova et al., 2010; Im et al., 2008; Shreeram et al., 2002). Cdc7 depletion by siRNA in combination with hydroxyurea or etoposide treatment impairs hyper-phosphorylation of Mcm2 at specific Cdc7-dependent phosphorylation sites and drug-induced hyper-phosphorylation of chromatin-bound Mcm4. Indeed, sustained inhibition of Cdc7 in the presence of hydroxyurea or etoposide increases cell death supporting the notion that the Cdc7 kinase plays a role in maintaining cell viability during replication stress (Tenca et al., 2007).

In a panel of 62 cancer cell lines Cdc7 protein expression was found to be increased in ~50% human tumour cell lines examined, whereas, Cdc7 protein was very low or undetectable in normal tissues and cell lines. In addition most of the cancer cell lines with increased Cdc7 protein levels also had increased Dbf4 abundance and a high expression of Cdc7 protein was also detected in primary breast, colon, and lung tumours but not in the matched normal tissues (Bonte et al., 2008). Analysis of tumour samples from breast and ovarian cancers have shown a correlation between overexpression of Cdc7 and poor survival, tumour grade, genetic instability and aneuploidy (Rodriguez-Acebes et al., 2010; Kulkarni et al., 2009; Choschzick et al., 2010), supporting the importance of Cdc7 in regulating cellular proliferation. Moreover, Cdc7-Dbf4 is overexpressed in oral squamous cell carcinoma and expression is positively associated with poor clinical outcome and enhances resistance to the DNA-damaging cytotoxic agents such as hydroxyurea and camptothecin (Cheng et al., 2013).

The observation that siRNA mediated knockdown of Cdc7 results in apoptosis in multiple cancer cell lines but not in normal cells makes Cdc7 an attractive cancer target. Moreover, inhibition of Cdc7 catalytic activity has been demonstrated to result in apoptotic cell death in multiple cancer cell types and tumour growth inhibition in preclinical cancer models (Montagoli et al., 2008). Furthermore, inhibition of Cdc7 blocks DNA synthesis, prevents the activation of replication origins but does not impede replication fork progression and does not trigger a sustained DNA damage response (Montagoli et al., 2008). Taken together these studies suggest selective inhibition of Cdc7 to be a promising anticancer therapeutic.

There is a need in the art for agents (alternative and/or improved) capable of inhibiting Cdc7.

SUMMARY OF THE INVENTION

In one aspect, the present invention provides a compound as defined herein, and/or a salt or solvate thereof.

In another aspect, the present invention provides a pharmaceutical composition which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in therapy.

In another aspect, the present invention provides a compound as defined herein, or a pharmaceutically acceptable salt or solvate thereof, or a pharmaceutical composition as defined herein, for use in the treatment of a proliferative condition.

In another aspect, the present invention provides a compound as defined herein, or a pharmaceutically acceptable salt or solvate thereof, or a pharmaceutical composition as defined herein, for use in the treatment of cancer.

In another aspect, the present invention provides a compound as defined herein, or a pharmaceutically acceptable salt or solvate thereof, or a pharmaceutical composition as defined herein, for use in the production of a Cdc7 inhibitory effect.

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer.

In another aspect, the present invention provides the use of a compound as defined herein, or a pharmaceutically acceptable salt or solvate thereof, in the manufacture of a medicament for use in the production of a Cdc7 inhibitory effect.

In another aspect, the present invention provides a method of inhibiting Cdc7 in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a proliferative disorder in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a combination comprising a compound, or a pharmaceutically acceptable salt or solvate thereof, as defined herein, with one or more additional therapeutic agents.

Preferred, suitable, and optional features of any one particular aspect of the present invention are also preferred, suitable, and optional features of any other aspect.

DETAILED DESCRIPTION OF THE INVENTION

Definitions

The compounds and intermediates described herein may be named according to either the IUPAC (International Union for Pure and Applied Chemistry) or CAS (Chemical Abstracts Service) nomenclature systems. It should be understood that unless expressly stated to the contrary, the terms "compounds of Formula I", "compounds of Formula Ib", "compounds of Formula Ic" and the more general term "compounds" refer to and include any and all compounds described by and/or with reference to Formula I, Ib and Ic respectively. It should also be understood that these terms encompasses all stereoisomers, i.e. cis and trans isomers, as well as optical isomers, i.e. R and S enantiomers, of such compounds and all salts thereof, in substantially pure form and/or any mixtures of the foregoing in any ratio. This understanding extends to pharmaceutical compositions and methods of treatment that employ or comprise one or more compounds of the Formula I, Ib and Ic, either by themselves or in combination with additional agents.

The various hydrocarbon-containing moieties provided herein may be described using a prefix designating the minimum and maximum number of carbon atoms in the moiety, e.g. "$(C_a-C_b)$". For example, $(C_a-C_b)$alkyl indicates an alkyl moiety having the integer "a" to the integer "b" number of carbon atoms, inclusive. Certain moieties may also be described according to the minimum and maximum number of members with or without specific reference to a particular atom or overall structure. For example, the terms "a to b membered ring" or "having between a to b members" refer to a moiety having the integer "a" to the integer "b" number of atoms, inclusive.

"About" when used herein in conjunction with a measurable value such as, for example, an amount or a period of time and the like, is meant to encompass reasonable variations of the value, for instance, to allow for experimental error in the measurement of said value.

As used herein by themselves or in conjunction with another term or terms, "alkyl" and "alkyl group" refer to a branched or unbranched saturated hydrocarbon chain. Unless specified otherwise, alkyl groups typically contain 1-10 carbon atoms, such as 1-6 carbon atoms or 1-4 carbon atoms or 1-3 carbon atoms, and can be substituted or unsubstituted. Representative examples include, but are not limited to, methyl, ethyl, n-propyl, i-propyl, n-butyl, i-butyl, s-butyl, t-butyl, n-pentyl, n-hexyl, n-heptyl, n-octyl, n-nonyl, n-decyl, isopropyl, tert-butyl, isobutyl, etc.

As used herein by themselves or in conjunction with another term or terms, "alkylene" and "alkylene group" refer to a branched or unbranched saturated hydrocarbon chain. Unless specified otherwise, alkylene groups typically contain 1-10 carbon atoms, such as 1-6 carbon atoms or 1-3 carbon atoms, and can be substituted or unsubstituted. Representative examples include, but are not limited to, methylene (—$CH_2$—), the ethylene isomers (—$CH(CH_3)$— and —$CH_2CH_2$—), the propylene isomers (—$CH(CH_3)CH_2$—, —$CH(CH_2CH=)$—, —$C(CH_3)=$—, and —$CH_2CH_2CH_2$—), etc.

As used herein by themselves or in conjunction with another term or terms, "alkenyl" and "alkenyl group" refer to a branched or unbranched hydrocarbon chain containing at least one double bond. Unless specified otherwise, alkenyl groups typically contain 2-10 carbon atoms, such as 2-6 carbon atoms or 2-4 carbon atoms, and can be substituted or unsubstituted. Representative examples include, but are not limited to, ethenyl, 3-buten-1-yl, 2-ethenylbutyl, and 3-hexen-1-yl.

As used herein by themselves or in conjunction with another term or terms, "alkynyl" and "alkynyl group" refer to a branched or unbranched hydrocarbon chain containing at least one triple bond. Unless specified otherwise, alkynyl groups typically contain 2-10 carbon atoms, such as 2-6 carbon atoms or 2-4 carbon atoms, and can be substituted or unsubstituted. Representative examples include, but are not limited to, ethynyl, 3-butyn-1-yl, propynyl, 2-butyn-1-yl, and 3-pentyn-1-yl.

As used herein by itself or in conjunction with another term or terms, "aromatic" refers to monocyclic and polycyclic ring systems containing 4n+2 pi electrons, where n is an integer. Aromatic should be understood as referring to and including ring systems that contain only carbon atoms (i.e. "aryl") as well as ring systems that contain at least one heteroatom selected from N, O or S (i.e. "heteroaromatic" or "heteroaryl"). An aromatic ring system can be substituted or unsubstituted.

As used herein by itself or in conjunction with another term or terms, "non-aromatic" refers to a monocyclic or polycyclic ring system having at least one double bond that is not part of an extended conjugated pi system. As used herein, non-aromatic refers to and includes ring systems that contain only carbon atoms as well as ring systems that contain at least one heteroatom selected from N, O or S. A non-aromatic ring system can be substituted or unsubstituted.

As used herein by themselves or in conjunction with another term or terms, "aryl" and "aryl group" refer to phenyl and 7-15 membered bicyclic or tricyclic hydrocarbon ring systems, including bridged, spiro, and/or fused ring systems, in which at least one of the rings is aromatic. Aryl groups can be substituted or unsubstituted. Unless specified otherwise, an aryl group may contain 6 ring atoms (i.e., phenyl) or a ring system containing 9 to 15 atoms, such as 9 to 11 ring atoms, or 9 or 10 ring atoms. Representative examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. Suitably an aryl group is phenyl.

As used herein by themselves or in conjunction with another term or terms, "arylene" and "arylene group" refer to a phenylene (—$C_6H_4$—) or to 7 to 15 membered bicyclic or tricyclic hydrocarbon ring systems, including bridged, spiro, and/or fused ring systems, in which at least one of the rings is aromatic. Arylene groups can be substituted or unsubstituted. In some embodiments, an arylene group may contain 6 (i.e., phenylene) ring atoms or be a ring system containing 9 to 15 atoms; such as 9 to 11 ring atoms; or 9 or 10 ring atoms. Arylene groups can be substituted or unsubstituted.

As used herein by themselves or in conjunction with another term or terms, "alkylaryl" and "alkylaryl group" refer to an alkyl group in which a hydrogen atom is replaced by an aryl group, wherein alkyl group and aryl group are as previously defined, such as, for example, benzyl ($C_6H_5CH_2$—). Alkylaryl groups can be substituted or unsubstituted.

As used herein by themselves or in conjunction with another term or terms, "carbocyclic group" and "carbocycle" refer to monocyclic and polycyclic ring systems that contain only carbon atoms in the ring(s), i.e., hydrocarbon ring systems, without regard or reference to aromaticity or degree of unsaturation. Thus, carbocyclic group should be understood as referring to and including ring systems that are fully saturated (such as, for example, a cyclohexyl group), ring systems that are aromatic (such as, for example, a phenyl group), as well as ring systems having fully saturated, aromatic and/or unsaturated portions (such as, for example, cyclohexenyl, 2,3-dihydro-indenyl, and 1,2,3,4-tetrahydronaphthalenyl). The terms carbocyclic and carbocycle further include bridged, fused, and spirocyclic ring systems.

As used herein by themselves or in conjunction with another term or terms, "cycloalkyl" and "cycloalkyl group" refer to a non-aromatic carbocyclic ring system, that may be monocyclic, bicyclic, or tricyclic, saturated or unsaturated, and may be bridged, spiro, and/or fused. A cycloalkyl group may be substituted or unsubstituted. Unless specified otherwise, a cycloalkyl group typically contains from 3 to 12 ring atoms. In some instances a cycloalkyl group may contain 4 to 10 ring atoms (e.g., 4 ring atoms, 5 ring atoms, 6 ring atoms, 7 ring atoms, etc.). Representative examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane.

As used herein by themselves or in conjunction with another term or terms, "alkylcycloalkyl" and "alkylcycloalkyl group" refer to an alkyl group in which a hydrogen atom is replaced by a cycloalkyl group, wherein alkyl group and cycloalkyl group are as previously defined, such as, for example, cyclohexylmethyl ($C_6H_{11}CH_2$—). Alkylcycloalkyl groups can be substituted or unsubstituted.

As used herein by themselves or in conjunction with another term or terms, "haloalkyl" and "haloalkyl group" refer to alkyl groups in which one or more hydrogen atoms are replaced by halogen atoms. Haloalkyl includes both saturated alkyl groups as well as unsaturated alkenyl and alkynyl groups. Representative examples include, but are not limited to, —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —Cl=$CH_2$, —C≡C—$CF_3$, —$CHFCH_2CH_3$ and —$CHFCH_2CF_3$. Haloalkyl groups can be substituted or unsubstituted.

As used herein by themselves or in conjunction with another term or terms, "halo" and "halogen" include fluorine, chlorine, bromine and iodine atoms and substituents.

As used herein by themselves or in conjunction with another term or terms, "heteroaryl" and "heteroaryl group" refer to (a) 5 and 6 membered monocyclic aromatic rings, which contain, in addition to carbon atom(s), at least one heteroatom, such as nitrogen, oxygen or sulfur, and (b) 7 to 15 membered bicyclic and tricyclic rings, which contain, in addition to carbon atom(s), at least one heteroatom, such as nitrogen, oxygen or sulfur, and in which at least one of the rings is aromatic. In some instances, a heteroaryl group can contain two or more heteroatoms, which may be the same or different. Heteroaryl groups can be substituted or unsubstituted, and may be bridged, spiro, and/or fused. In some instances, a heteroaryl group may contain 5, 6, or 8 to 15 ring atoms. In other instances, a heteroaryl group may contain 5 to 10 ring atoms, such as 5, 6, 9, or 10 ring atoms. Representative examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0$^{2,7}$]dodeca- 2(7),3,5-trienyl, 12-oxa-10-aza-tricyclo[6.3.1.0$^{2,7}$]dodeca-2 (7),3,5-trienyl, 12-aza-tricyclo[7.2.1.0$^{2,7}$]dodeca-2(7),3,5-trienyl, 10-aza-tricyclo[6.3.2.0$^{2,7}$]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. Suitably, a heteroaryl is a 5- or 6-membered heteroaryl ring comprising one, two or three heteroatoms selected from N, O or S.

As used herein by themselves or in conjunction with another term or terms, "alkylheteroaryl" and "alkylheteroaryl group" refer to an alkyl group in which a hydrogen atom is replaced by a heteroaryl group, wherein alkyl group and heteroaryl group are as previously defined. Alkylheteroaryl groups can be substituted or unsubstituted.

As used herein by themselves or in conjunction with another term or terms, "heterocyclic group" and "heterocycle" refer to monocyclic and polycyclic ring systems that contain carbon atoms and at least one heteroatom selected from nitrogen, oxygen, sulfur or phosphorus in the ring(s), without regard or reference to aromaticity or degree of unsaturation. Thus, a heterocyclic group should be understood as referring to and including ring systems that are fully saturated (such as, for example, a piperidinyl group), ring systems that are aromatic (such as, for example, a pyrindinyl group), as well as ring systems having fully saturated, aromatic and/or unsaturated portions (such as, for example, 1,2,3,6-tetrahydropyridinyl and 6,8-dihydro-5H-[1,2,4]triazolo[4,3-a]pyrizinyl). The terms heterocyclic and heterocycle further include bridged, fused, and spirocyclic ring systems.

As used herein by themselves or in conjunction with another term or terms, "heterocycloalkyl" and "heterocycloalkyl group" refer to 3 to 15 membered monocyclic, bicyclic, and tricyclic non-aromatic ring systems, which contain, in addition to carbon atom(s), at least one heteroatom, such as nitrogen, oxygen, sulfur or phosphorus. Heterocycloalkyl groups may be fully saturated or contain unsaturated portions and may be bridged, spiro, and/or fused ring systems. In some instances a heterocycloalkyl group may contain at least two or heteroatoms, which may be the same or different. Heterocycloalkyl groups can be substituted or unsubstituted. In some instances a heterocycloalkyl group may contain from 3 to 10 ring atoms or from 3 to 7 ring atoms or from 5 to 7 ring atoms, such as 5 ring atoms, 6 ring atoms, or 7 ring atoms. Representative examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptanyl, 8-oxa-3-aza-bicyclo[3.2.1]octanyl, 3,8-diaza-bicyclo[3.2.1]octanyl, 2,5-diaza-bicyclo[2.2.1]heptanyl, 3,8-diaza-bicyclo[3.2.1]octanyl, 3,9-diaza-bicyclo[4.2.1]nonanyl, 2,6-diaza-bicyclo[3.2.2]nonanyl, [1,4]oxaphosphinanyl-4-oxide, [1,4]azaphosphinanyl-4-oxide, [1,2]oxaphospholanyl-2-oxide, phosphinanyl-1-oxide, [1,3]azaphospholidinynl-3-oxide, [1,3]oxaphospholanyl-3-oxide, 7-oxabicyclo[2.2.1]heptanyl, 6,8-dihydro-5H-[1,2,4]triazolo[4,3-a]pyrazin-7-yl, 6,8-dihydro-5H-imidazo[1,5-a]pyrazin-7-yl, 6,8-dihydro-5H-imidazo[1,2-a]pyrazin-7-yl, 5,6,8,9-tetrahydro-[1,2,4]triazolo[4,3-d][1,4]diazepin-7-yl and 6,8-dihydro-5H-[1,2,4]triazolo[4,3-a]pyrazin-7-yl. Suitably, a heterocyclylalkyl group as defined herein is a monocyclic, bicyclic or spiro heterocyclyl group comprising one, two or three heteroatoms selected from N, O or S.

As used herein by themselves or in conjunction with another term or terms, "heterocycloalkylene" and "heterocycloalkylene group" refer to 3 to 15 membered monocyclic, bicyclic, or tricyclic non-aromatic ring systems, which contain, in addition to carbon atom(s), at least one heteroatom, such as nitrogen, oxygen, sulfur or phosphorus. Heterocycloalkylene groups may be fully saturated or contain unsaturated portions and may be bridged, spiro, and/or fused. Heterocycloalkylene groups can be substituted or unsubstituted. In some instances, a heterocycloalkylene group may contain from 3 to 10 ring atoms; such as from 3 to 7 ring atoms. In other instances a heterocycloalkylene group may contain from 5 to 7 ring atoms, such as 5 ring atoms, 6 ring atoms, or 7 ring atoms.

As used herein by themselves or in conjunction with another term or terms, "alkylheterocycloalkyl" and "alkylheterocycloalkyl group" refer to an alkyl group in which a hydrogen atom is replaced by a heterocycloalkyl group, wherein alkyl group and heterocycloalkyl group are as previously defined, such as, for example, pyrrolidinylmethyl ($C_4H_8NCH_2$—). Alkylheteroycloalkyl groups can be substituted or unsubstituted.

As used herein by itself or in conjunction with another term or terms, "pharmaceutically acceptable" refers to materials that are generally chemically and/or physically compatible with other ingredients (such as, for example, with reference to a formulation), and/or is generally physiologically compatible with the recipient (such as, for example, a subject) thereof.

As used herein by itself or in conjunction with another term or terms, "pharmaceutical composition" refers to a composition that can be used to treat a disease, condition, or disorder in a subject, including a human.

As used herein by itself or in conjunction with another term or terms, "pseudohalogen" refers to —OCN, —SCN, —$CF_3$, and —CN.

As used herein by themselves or in conjunction with another term or terms, "stable" and "chemically stable" refer to a compound that is sufficiently robust to be isolated from a reaction mixture with a useful degree of purity. The present application is directed solely to the preparation of stable compounds. When lists of alternative substituents include members which, owing to valency requirements, chemical stability, or other reasons, cannot be used to substitute a particular group, the list is intended to be read in context to include those members of the list that are suitable for substituting the particular group. For example, when considering the degree of optional substitution of a particular moiety, it should be understood that the number of substituents does not exceed the valency appropriate for that moiety. For example, if $R^1$ is a methyl group (—$CH_3$), it can be optionally substituted by 1 to 3 $R^5$.

As used herein by themselves or in conjunction with another term or terms, "subject(s)" and "patient(s)", refer to mammals, including humans.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s).

As used herein by themselves or in conjunction with another term or terms, "therapeutic" and "therapeutically effective amount" refer to an amount a compound, composition or medicament that (a) inhibits or causes an improvement in a particular disease, condition or disorder; (b) attenuates, ameliorates or eliminates one or more symptoms of a particular disease, condition or disorder; (c) or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c). It should be understood that in, for example, a human or other mammal, a therapeutically effective amount can be determined experimentally in a laboratory or clinical setting, or a therapeutically effective amount may be the amount required by the guidelines of the United States Food and Drug Administration (FDA) or equivalent foreign regulatory body, for the particular disease and subject being treated. It should be appreciated that determination of proper dosage forms, dosage amounts, and routes of administration is within the level of ordinary skill in the pharmaceutical and medical arts.

As used herein whether by themselves or in conjunction with another term or terms, "treating", "treated" and "treatment", refer to and include prophylactic, ameliorative, palliative, and curative uses and results. In some embodiments, the terms "treating", "treated", and "treatment" refer to curative uses and results as well as uses and results that diminish or reduce the severity of a particular condition, characteristic, symptom, disorder, or disease described herein. For example, treatment can include diminishment of several symptoms of a condition or disorder or complete eradication of said condition or disorder. It should be understood that the term "prophylactic" as used herein is not absolute but rather refers to uses and results where the administration of a compound or composition diminishes the likelihood or seriousness of a condition, symptom, or disease state, and/or delays the onset of a condition, symptom, or disease state for a period of time.

As used herein, a "therapeutically active agent", whether used alone or in conjunction with another term or terms, refers to any compound, i.e. a drug, that has been found to be useful in the treatment of a disease, disorder or condition and is not described by Formula I. It should be understood that a therapeutically active agent may not be approved by the FDA or an equivalent foreign regulatory body.

A "therapeutically effective amount" means the amount of a compound that, when administered to a subject or patient for treating a disease, is sufficient to effect such treatment for the disease. The "therapeutically effective amount" will vary depending on the compound, the disease and its severity and the age, weight, etc., of the subject or patient to be treated.

Compounds

In a first aspect, the present invention relates to a compound of Formula I:

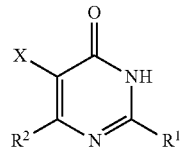

Formula I or a salt or solvate thereof wherein,

X is chosen from halogen, haloC$_1$-C$_6$alkyl, NO$_2$, OCN, SCN, —C(=O)NR$^5$R$^6$, —NHS(O)$_2$R$^6$, and CN;

R$^2$ is a group A-B-C wherein,

A is a bond or is C$_1$-C$_{10}$alkyl;

B is absent or is chosen from S(O)$_p$, NR$^3$, O, C$_2$-C$_{10}$alkenyl, and C$_2$-C$_{10}$alkynyl; and C is a 3 to 15 membered heterocycloalkyl group or a 4 to 11 membered cycloalkyl group either of which is optionally substituted with one or more R$^5$ groups; or R$^1$ is a heteroaryl group of Formula A

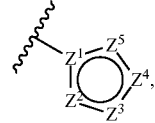

Formula A wherein

Z$^1$ is selected from C and N,

Z$^2$ is selected from CR$^a$, NR$^b$, N, O and S,

Z$^3$ is selected is N and NR$^c$,

Z$^4$ and Z$^5$ are independently selected from O, N, S, NR$^d$ and CR$^e$.

R$^a$ is selected from hydrogen, hydroxyl, halogen, COOR$^3$, C$_1$-C$_6$alkyl, C$_2$-C$_6$alkenyl, C$_2$-C$_6$alkynyl, C$_0$-C$_6$alkylaryl, C$_0$-C$_6$alkylcycloalkyl, C$_0$-C$_6$alkylheterocycloalkyl, C$_0$-C$_6$alkylheteroaryl, C$_0$-C$_6$alkylCN, C$_0$-C$_6$alkylC(=O)C$_0$-C$_6$alkylR$^3$, C$_0$-C$_6$alkylC(=O)C$_0$-C$_6$alkylOR$^3$, C$_0$-C$_6$alkylC(=O)C$_0$-C$_6$alkylNR$^3$R$^4$, haloC$_1$-C$_6$alkyl, NO$_2$, C$_0$-C$_6$alkylNR$^3$R$^4$, C$_0$-C$_6$alkylNR$^3$C$_0$-C$_6$alkylOR$^4$, C$_0$-C$_6$alkylOS(=O)R$^4$, —C$_0$-C$_6$alkylOS(=O)$_2$R$^4$, —C$_0$-C$_6$alkylS(=O)$_p$R$^4$, —OCN, and —SCN, wherein any of the foregoing is optionally substituted with one or more R$^5$ groups;

R$^b$ and R$^c$ are independently selected from hydrogen, C$_1$-C$_6$ alkyl and C$_3$-C$_6$ cycloalkyl;

R$^a$ and R$^c$ are taken together to form a fused 6-membered ring optionally substituted with one or more R$^5$ groups;

R$^d$ is selected from hydrogen, C$_1$-C$_6$ alkyl and C$_3$-C$_6$ cycloalkyl; and R$^e$ is selected from hydrogen, hydroxyl, halogen, OR$^3$, COOR$^3$, C$_1$-C$_6$alkyl, C$_2$-C$_6$alkenyl, C$_2$-C$_6$alkynyl, C$_0$-C$_6$alkylaryl, C$_0$-C$_6$alkylcycloalkyl, C$_0$-C$_6$alkylheterocycloalkyl, C$_0$-C$_6$alkylheteroaryl, C$_0$-C$_6$alkylCN, C$_0$-C$_6$alkylC(=O)C$_0$-C$_6$alkylR$^3$, C$_0$-C$_6$alkylC(=O)C$_0$-C$_6$alkylOR$^3$, C$_0$-C$_6$alkylC(=O)C$_0$-C$_6$alkylNR$^3$R$^4$, haloC$_1$-C$_6$alkyl, NO$_2$, C$_0$-C$_6$alkylNR$^3$R$^4$, C$_0$-C$_6$alkylNR$^3$C$_0$-C$_6$alkylOR$^4$, C$_0$-C$_6$alkylOS(=O)R$^4$, —C$_0$-C$_6$alkylOS(=O)$_2$R$^4$, —C$_0$-C$_6$alkylS(=O)$_p$R$^4$, —OCN, and —SCN; or two adjacent R$^e$ groups, adjacent R$^c$ and R$^e$ or adjacent R$^e$ and R$^d$ groups are taken together to form a fused 6-membered ring optionally substituted with one or more R$^5$ groups;

each $R^3$ and $R^4$ are each independently chosen from H, $C_1$-$C_6$alkyl, $C_2$-$C_6$alkenyl, $C_2$-$C_6$alkynyl, halo$C_1$-$C_6$alkyl, $C_0$-$C_6$alkylaryl, $C_0$-$C_6$alkylcycloalkyl, $C_0$-$C_6$alkylheteroaryl, $C_0$-$C_6$alkylheterocycloalkyl, wherein any of the foregoing, except for H, is optionally substituted with one or more $R^5$; or $R^3$ and $R^4$ are taken together to form a 3 to 7 membered carbocyclic or heterocyclic ring system, wherein said ring system is optionally substituted with one or more $R^5$;

Each $R^5$ is independently chosen from halogen, hydroxyl, $OR^6$, $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkyl$R^6$, —$C_0$-$C_6$alkylC(=O)$C_0$-$C_6$alkyl$OR^6$, —$C_0$-$C_6$alkylC(=O)$C_0$-$C_6$alkylNR$^6$R$^6$, —$C_0$-$C_6$alkylC(=O)$C_0$-$C_6$alkylNR$^6$C(=O)$OR^6$, halo$C_1$-$C_6$alkyl, $NO_2$, —$C_0$-$C_6$alkylNR$^6$R$^6$, —$C_0$-$C_6$alkylNR$^6$$C_0$-$C_6$alkyl$OR^6$, —$C_0$-$C_6$alkylNR$^6$$C_0$-$C_6$alkylC(=O)$R^6$, —$C_0$-$C_6$alkyl$OR^6$, (=O), —$C_0$-$C_6$alkylOC(=O)$C_0$-$C_6$alkyl$R^6$, —$C_0$-$C_6$alkylOC(=O)$C_0$-$C_6$alkylNR$^6$R$^6$, —$C_0$-$C_6$alkylOC(=O)$C_0$-$C_6$alkyl$OR^6$, —$C_0$-$C_6$alkylOS(=O) $R^6$, —$C_0$-$C_6$alkylOS(=O)$_2$$R^6$, —$C_0$-$C_6$alkylOS(=O)$_2$$C_0$-$C_6$alkyl$OR^6$, —$C_0$-$C_6$alkylOS(=O)$_2$$C_0$-$C_6$alkylNR$^6$R$^6$, —$C_0$-$C_6$alkylS(=O)$_p$$R^6$, —$C_0$-$C_6$alkylS(=O)$_2$$C_0$-$C_6$alkylNR$^6$R$^6$, —$C_0$-$C_6$alkylS(=O)$C_0$-$C_6$alkylNR$^6$R$^6$, wherein each of the foregoing is optionally substituted with $R^7$, or together with carbon atoms to which they are attached, two $R^5$ groups are linked to form a fused aryl, heteroaryl, 3 to 6 membered heterocycloalkyl or a 3 to 6 membered cycloalkyl;

each $R^6$ is independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, $C_0$-$C_6$alkylheterocycloalkyl, wherein each of the foregoing is optionally substituted with $R^7$; or two $R^6$ are taken together to form a 3 to 15 membered carbocyclic or heterocyclic ring system, wherein said ring system is optionally substituted with one or more $R^7$;

each $R^7$ is independently chosen from halogen, hydroxyl, $C_1$-$C_6$alkyl, $OC_1$-$C_6$alkyl, and halo$C_1$-$C_6$alkyl; and each p is independently 0, 1 or 2;

with the proviso that the compound of Formula I is not one of the following compounds:

6-cyclopentyl-5-iodo-2-(5-thiazolyl)-4(3H)-pyrimidinone;
6-cyclopentyl-2-(1-ethyl-1H-pyrazol-4-yl)-5-iodo-4(3H)-pyrimidinone;
6-cyclopentyl-5-iodo-2-(1-propyl-1H-pyrazol-4-yl)-4(3H)-pyrimidinone;
5-bromo-6-cyclopentyl-2(1-ethyl-1H-pyrazol-4-yl)-4(3H)-pyrimidinone;
5-bromo-6-cyclopentyl-2(1-propyl-1H-pyrazol-4-yl)-4(3H)-pyrimidinone;
5-bromo-6-cyclopentyl-2(1-isopropyl-1H-pyrazol-4-yl)-4(3H)-pyrimidinone;
6-cyclopentyl-5-iodo-2(1-isopropyl-1H-pyrazol-4-yl)-4(3H)-pyrimidinone;
5-bromo-6-cyclopentyl-2(5-thiazolyl)-4(3H)-pyrimidinone;
5-bromo-6-cyclopentyl-2(3,5-dimethyl-4-isoxazolyl)-4(3H)-pyrimidinone;
5-bromo-6-cyclopentyl-2(1-propyl-1H-imidazol-5-yl)-4(3H)-pyrimidinone;
6-cyclopentyl-5-iodo-2-(1-methyl-1H-pyrazol-3-yl)-4(3H)-pyrimidinone;
5-bromo-6-cyclopentyl-2(1-cyclopropyl-1H-imidazol-5-yl)-4(3H)-pyrimidinone;
5-bromo-6-cyclopentyl-2(1-methyl-1H-pyrazol-3-yl)-4(3H)-pyrimidinone;
5-bromo-6-cyclopentyl-2(1,5-dimethyl-1H-pyrazol-4-yl)-4(3H)-pyrimidinone;
6-cyclopentyl-5-iodo-2(1,3,5-trimethyl-1H-pyrazol-4-yl)-4(3H)-pyrimidinone;
6-cyclopentyl-5-iodo-2-[1 (1-methylethyl)-1H-imidazol-5-yl]-4(3H)-pyrimidinone;
6-cyclopentyl-5-iodo-2-(1-propyl-1H-imidazol-5-yl)-4(3H)-pyrimidinone;
6-cyclopentyl-2-(1-ethyl-1H-imidazol-5-yl)-5-iodo-4(3H)-pyrimidinone;
5-bromo-6-cyclopentyl-2(1-methyl-1H-pyrazol-4-yl)-4(3H)-pyrimidinone;
5-bromo-6-cyclopentyl-2(1-methyl-1H-imidazol-5-yl)-4(3H)-pyrimidinone;
6-cyclopentyl-5-iodo-2-(1-methyl-1H-pyrazol-4-yl)-4(3H)-pyrimidinone;
5-bromo-6-cyclopentyl-2-(1,3-dimethyl-1H-pyrazol-4-yl)-4(3H)-pyrimidinone;
6-cyclopentyl-2-(1,3-dimethyl-1H-pyrazol-4-yl)-5-iodo-4(3H)-pyrimidinone;
6-cyclopentyl-2-(3,5-dimethyl-4-isoxazolyl)-5-iodo-4(3H)-pyrimidinone;
6-cyclopentyl-5-iodo-2-(1-methyl-1H-imidazol-5-yl)-4(3H)-pyrimidinone;
5-bromo-6-cyclopentyl-2-[1 (1-methylethyl)-1H-imidazol-5-yl]-4(3H)-pyrimidinone;
5-bromo-6-cyclopentyl-2-(3-ethyl-1-methyl-1H-pyrazol-4-yl)-4(3H)-pyrimidinone;
5-bromo-6-cyclopentyl-2-(1,3,5-trimethyl-1H-pyrazol-4-yl)-4(3H)-pyrimidinone;
6-cyclopentyl-2-(1,5-dimethyl-1H-pyrazol-4-yl)-5-iodo-4(3H)-pyrimidinone;
5-bromo-6-cyclopentyl-2-(1-ethyl-1H-imidazol-5-yl)-4(3H)-pyrimidinone;
6-cyclopentyl-2-(1-cyclopropyl-1H-imidazol-5-yl)-5-iodo-4(3H)-pyrimidinone;
5-bromo-6-cyclopentyl-2-(1H-1,2,4-triazol-5-yl)-4(3H)-pyrimidinone;
6-cyclopentyl-2-(3-ethyl-1-methyl-1H-pyrazol-4-yl)-5-iodo-4(3H)-pyrimidinone;
6-cyclopentyl-5-iodo-2-(1H-1,2,3-triazol-5-yl)-4(3H)-pyrimidinone;
6-cyclopentyl-5-iodo-2-(1H-1,2,4-triazol-5-yl)-4(3H)-pyrimidinone;
5-bromo-6-cyclopentyl-2(1H-1,2,3-triazol-5-yl)-4(3H)-pyrimidinone;
6-cyclopentyl-5-iodo-2-(1-propyl-1H-pyrazol-5-yl)-4(3H)-pyrimidinone;
5-bromo-6-cyclopentyl-2(1-propyl-1H-pyrazol-5-yl)-4(3H)-pyrimidinone;
5-bromo-6-cyclopentyl-2(1-methyl-1H-pyrazol-5-yl)-4(3H)-pyrimidinone;
6-cyclopentyl-5-iodo-2-(1-methyl-1H-pyrazol-5-yl)-4(3H)-pyrimidinone;
5-bromo-6-cyclopentyl-2-(1-ethyl-1H-pyrazol-5-yl)-4(3H)-pyrimidinone; and
6-cyclopentyl-2-(1-ethyl-1H-pyrazol-5-yl)-5-iodo-4(3H)-pyrimidinone.

Particular embodiments of the invention include, for example, compounds of the formula I, or salts and/or solvates thereof, wherein alternative definitions of each of p, $R_1$, $R_2$, $R_3$, $R_4$, $R_5$, $R_6$, $R_7$ and X are defined in the following numbered paragraphs. Where not described otherwise, substituents have the same meaning as described in the first aspect above.

1) Each p is independently 1 or 2;
2) p is 2;
3) X is chosen from halogen, haloC$_1$-C$_6$alkyl, OCN, SCN, NO$_2$ and CN;
4) X is chosen from halogen, haloC$_1$-C$_2$alkyl, and CN;
5) X is chosen from halogen, CF$_3$, and CN;
6) X is chosen from fluoro, chloro, bromo, iodo and CN.
7) X is a halogen;
8) X is chosen from fluoro or chloro;
9) X is chloro;
10) R$^2$ is a group A-B-C wherein A is a bond;
11) R$^2$ is a group A-B-C wherein B is absent.
12) R$^2$ is a group A-B-C wherein B is selected from S(O)$_p$, NR$^3$ or O.
13) R$^2$ is a group A-B-C wherein C is a 3 to 7 membered heterocycloalkyl or a 4 to 7 membered cycloalkyl either of which is optionally substituted with one or more R$^5$.
14) R$^2$ is a group A-B-C wherein C is selected from a 5 to 7 membered heterocycloalkyl which is optionally substituted with one of more R$^5$ group.
15) R$^2$ is a group A-B-C wherein C is selected from:

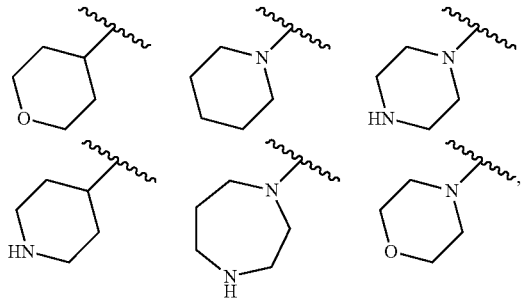

each optionally substituted with one of more R$^5$ group.
16) R$^2$ is a group A-B-C wherein:
A is a bond or is C$_1$-C$_2$alkyl;
B is absent or is chosen from S, NR$^3$ or 0; and
C is a 3 to 12 membered heterocycloalkyl or a 6 to 11 membered cycloalkyl either of which is optionally substituted with one or more R$^5$;
17) R$^2$ is a group A-B-C wherein:
A is a bond;
B is absent; and
C is a 3 to 7 membered heterocycloalkyl or a 4 to 8 membered cycloalkyl either of which is optionally substituted with one or more R$^5$ group.
18) R$^2$ is a 3 to 12 membered heterocycloalkyl or a 6 to 11 membered cycloalkyl either of which is optionally substituted with one or more R$^5$;
19) R$^2$ is a 3 to 12 membered heterocycloalkyl optionally substituted with one or more R$^5$;
20) R$^2$ is a 3 to 8 membered heterocycloalkyl optionally substituted with one or more R$^5$
21) R$^2$ is a 4 to 8 membered heterocycloalkyl optionally substituted with one or more R$^5$
22) R$^2$ is a 5 to 8 membered heterocycloalkyl optionally substituted with one or more R$^5$;
23) R$^2$ is a 6 to 8 membered heterocycloalkyl optionally substituted with one or more R$^5$;
24) R$^2$ is a 6 and 7 membered heterocycloalkyl optionally substituted with one or more R$^5$;
25) R$^2$ is selected from a piperidinyl, piperazinyl, homopiperazinyl, morpholino and a tetrahydropyranyl group, each of which is optionally substituted by one or more R$^5$ group.
26) R$^2$ is selected from:

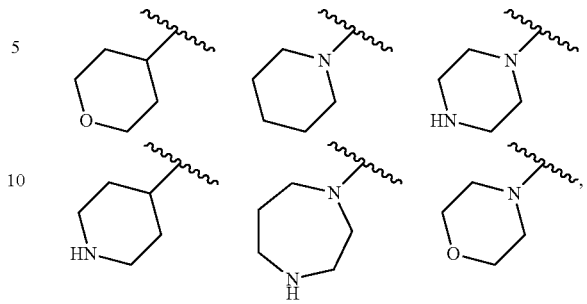

each optionally substituted with one of more R$^5$ group.
27) R$^2$ is selected from piperazinyl, homopiperazinyl and morpholino, each of which is optionally substituted by one or more R$^5$ group.
28) R$^2$ is selected from

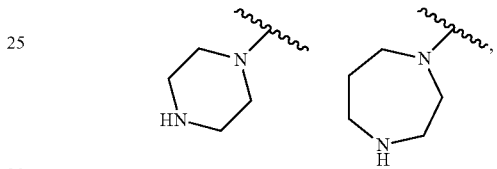

each optionally substituted with one of more R$^5$ group.
29) R$^2$ is selected from

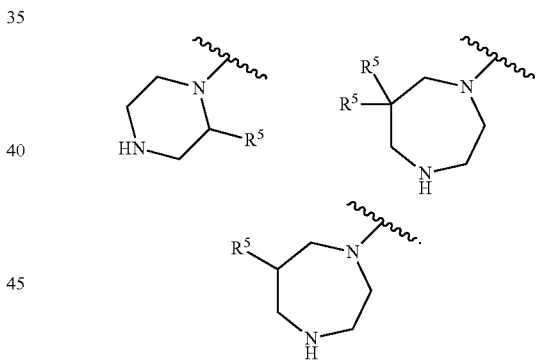

30) Z$^1$ is C.
31) Z$^2$ is CR$^a$.
32) Z$^3$ is N.
33) Z$^5$ is O or S
34) Z$^4$ is NR$^b$ or N
35) Z$^3$ is N and Z$^4$ is NR$^b$.
36) Z$^3$ is N, Z$^4$ is NR$^b$ and Z$^2$ is CR$^a$.
37) Z$^3$ is N, Z$^4$ is NR$^b$ and Z$^5$ is CR$^e$.
38) Z$^3$ is N, Z$^4$ is NH and Z$^2$ is CR$^a$.
39) Z$^3$ is N, Z$^4$ is NH and Z$^5$ is CR$^e$.
40) Z$^1$ is C, Z$^3$ is N, Z$^4$ is NR$^b$ and Z$^2$ is CR$^a$.
41) Z$^1$ is C, Z$^3$ is N, Z$^4$ is NR$^b$, and Z$^5$ is CR$^e$.
42) Z$^3$ is N and Z$^5$ is S or O.
43) Z$^3$ is N, Z$^5$ is S or O and Z$^2$ is CR$^a$.
44) Z$^3$ is N, Z$^5$ is S or O, Z$^1$ is C and Z$^2$ is CR$^a$.

45) R¹ is a heteroaryl group of Formula A1:

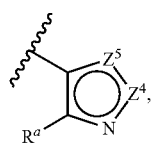

[A1]

46) R¹ is a heteroaryl group of Formula A2:

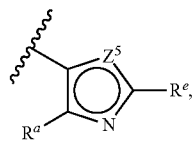

[A2]

47) R¹ is a heteroaryl group of Formula A3:

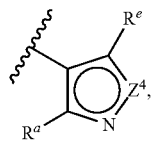

[A3]

48) R¹ is selected from:

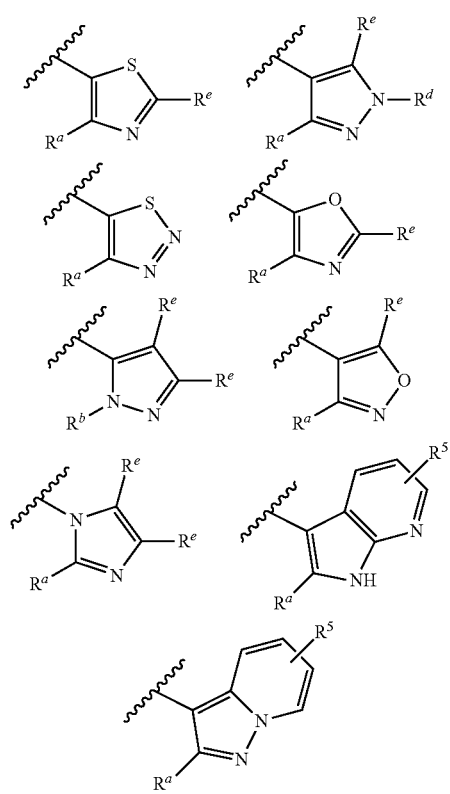

49) R¹ is selected from

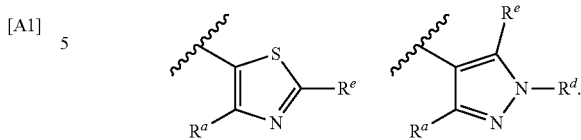

50) R¹ is selected from

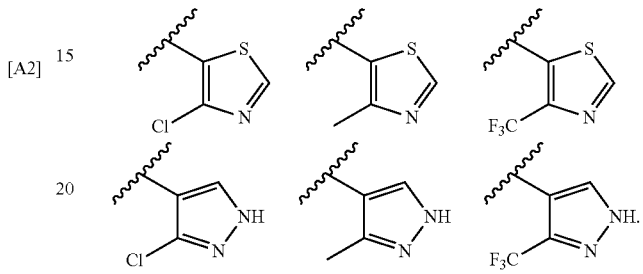

51) R¹ is selected from

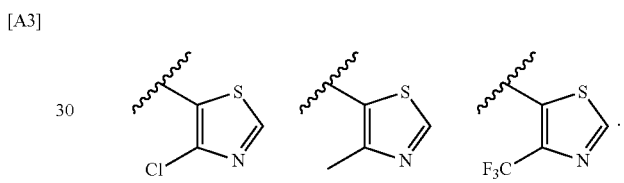

52) R¹ is selected from

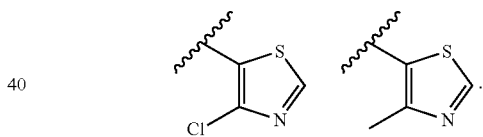

53) R³ and R⁴ are each independently chosen from H, $C_1$-$C_3$alkyl, halo$C_1$-$C_3$alkyl, $C_0$-$C_6$alkylaryl, $C_0$-$C_6$alkylcycloalkyl, $C_0$-$C_6$alkylheteroaryl, or $C_0$-$C_6$alkylheterocycloalkyl;

54) R³ and R⁴ are each independently chosen from H, $C_1$-$C_3$alkyl, halo$C_1$-$C_3$alkyl, aryl, cycloalkyl, heteroaryl, or heterocycloalkyl;

55) R³ and R⁴ are each independently chosen from H, $C_1$-$C_3$alkyl or halo$C_1$-$C_3$alkyl;

56) R³ and R⁴ are each independently chosen from H, or $C_1$-$C_3$alkyl;

57) Each R⁵ is halogen, hydroxyl, OR⁶, $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, —$C_0$-$C_6$alkylC(=O)$C_0$-$C_6$alkylR⁶, —$C_0$-$C_6$alkylC(=O)$C_0$-$C_6$alkylOR⁶, —$C_0$-$C_6$alkylC(=O)$C_0$-$C_6$alkylNR⁶R⁶, —$C_0$-$C_6$alkylC(=O)$C_0$-$C_6$alkylNR⁶C(=O)OR⁶, halo$C_1$-$C_6$alkyl and NO₂, wherein each of the foregoing is optionally substituted with R⁷, or together with carbon atoms to which they are attached, two R⁵ groups are linked to form a fused aryl, heteroaryl, 3 to 6 membered heterocycloalkyl or a 3 to 6 membered cycloalkyl;

58) Each $R^5$ is halogen, hydroxyl, $OR^6$, $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, halo$C_1$-$C_6$alkyl and $NO_2$, wherein each of the foregoing is optionally substituted with $R^7$, or
together with carbon atoms to which they are attached, two $R^5$ groups are linked to form a fused aryl, heteroaryl, 3 to 6 membered heterocycloalkyl or a 3 to 6 membered cycloalkyl;

59) Each $R^5$ is halogen, hydroxyl, $OR^6$, $C_1$-$C_{10}$alkyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, halo$C_1$-$C_6$alkyl and $NO_2$, wherein each of the foregoing is optionally substituted with $R^7$, or
together with carbon atoms to which they are attached, two $R^5$ groups are linked to form a fused aryl, heteroaryl, 3 to 6 membered heterocycloalkyl or a 3 to 6 membered cycloalkyl;

60) Each $R^5$ is halogen, hydroxyl, $OR^6$, $C_1$-$C_6$alkyl, $C_0$-$C_6$alkylaryl, $C_0$-$C_6$alkylcycloalkyl, $C_0$-$C_6$alkylheterocycloalkyl, $C_0$-$C_6$alkylheteroaryl, —$C_0$-$C_6$alkylCN, halo$C_1$-$C_6$alkyl and $NO_2$, wherein each of the foregoing is optionally substituted with $R^7$.

61) Each $R^5$ is selected from halogen, hydroxyl, $OR^6$, $C_1$-$C_{10}$alkyl, —$C_0$-$C_6$alkylC(=O)$C_0$-$C_6$alkyl$R^6$, —$C_0$-$C_6$alkylC(=O)$C_0$-$C_6$alkyl$OR^6$, halo$C_1$-$C_6$alkyl, —$C_0$-$C_6$alkyl$OR^6$ and (=O), wherein each of the foregoing is optionally substituted with $R^7$.

62) Each $R^5$ is selected from halogen, hydroxyl, $C_1$-$C_3$alkyl, halo$C_1$-$C_6$alkyl and (=O).

63) Each $R^5$ is selected from $C_1$-$C_4$alkyl, halo$C_1$-$C_3$alkyl or halogen;

64) Each $R^5$ is selected from fluoro, chloro, methyl, trifluoromethyl and difluoromethyl.

65) Each $R^6$ is independently chosen from H, $C_1$-$C_{10}$alkyl, halo$C_1$-$C_6$alkyl, $C_0$-$C_2$alkylaryl, $C_0$-$C_2$alkylcycloalkyl, $C_0$-$C_2$alkylheteroaryl, $C_0$-$C_2$alkylheterocycloalkyl, wherein any of the foregoing except for H is optionally substituted with one or more $R^7$; or
Two $R^6$ may be taken together to form a 3 to 6 membered carbocyclic or heterocyclic ring system, wherein said ring system is optionally substituted with one or more $R^7$;

66) Each $R^6$ is independently chosen from H, $C_1$-$C_6$alkyl, halo$C_1$-$C_4$alkyl, $C_0$-$C_2$alkylaryl, $C_0$-$C_2$alkyl-5- or 6-membered cycloalkyl, $C_0$-$C_2$alkyl-5- or 6-membered heteroaryl, $C_0$-$C_2$alkyl-5- or 6-membered heterocycloalkyl, wherein any of the foregoing except for H is optionally substituted with one or more $R^7$;

67) Each $R^6$ is independently chosen from H, $C_1$-$C_4$alkyl, halo$C_1$-$C_2$alkyl, $C_0$-$C_2$alkylaryl, $C_0$-$C_2$alkyl-5- or 6-membered cycloalkyl, $C_0$-$C_2$alkyl-5- or 6-membered heteroaryl, $C_0$-$C_2$alkyl-5- or 6-membered heterocycloalkyl, wherein any of the foregoing except for H is optionally substituted with one or more $R^7$;

68) Each $R^6$ is independently chosen from halogen and $C_1$-$C_4$alkyl.

69) Each $R^7$ is independently chosen from halogen, hydroxyl and $C_1$-$C_6$alkyl.

70) Each $R^7$ is independently chosen from halogen and $C_1$-$C_4$alkyl.

In one embodiment, X is as defined in any one of paragraphs (5), $R^1$ is as defined in any one of paragraphs (45) to (52).

In one embodiment, X is as defined in any one of paragraphs (7), $R^1$ is as defined in any one of paragraphs (45) to (52).

In one embodiment, X is as defined in any one of paragraphs (9), $R^1$ is as defined in any one of paragraphs (45) to (52).

In one embodiment, X is as defined in any one of paragraphs (5), $R^1$ is as defined in any one of paragraphs (45) to (52) and $R^2$ is as defined in paragraph (24).

In one embodiment, X is as defined in any one of paragraphs (7), $R^1$ is as defined in any one of paragraphs (45) to (52) and $R^2$ is as defined in paragraph (24).

In one embodiment, X is as defined in any one of paragraphs (9), $R^1$ is as defined in any one of paragraphs (45) to (52) and $R^2$ is as defined in paragraph (24).

In one embodiment, X is as defined in any one of paragraphs (5), $R^1$ is as defined in any one of paragraphs (45) to (52) and $R^2$ is as defined in paragraph (26).

In one embodiment, X is as defined in any one of paragraphs (7), $R^1$ is as defined in any one of paragraphs (45) to (52) and $R^2$ is as defined in paragraph (26).

In one embodiment, X is as defined in any one of paragraphs (9), $R^1$ is as defined in any one of paragraphs (45) to (52) and $R^2$ is as defined in paragraph (26).

In one embodiment, X is as defined in any one of paragraphs (5), $R^1$ is as defined in any one of paragraphs (45) to (52) and $R^2$ is as defined in paragraph (28).

In one embodiment, X is as defined in any one of paragraphs (7), $R^1$ is as defined in any one of paragraphs (45) to (52) and $R^2$ is as defined in paragraph (28).

In one embodiment, X is as defined in any one of paragraphs (9), $R^1$ is as defined in any one of paragraphs (45) to (52) and $R^2$ is as defined in paragraph (28).

In one embodiment, X is as defined in any one of paragraphs (5), $R^2$ is as defined in any one of paragraphs (10) to (29).

In one embodiment, X is as defined in any one of paragraphs (7), $R^2$ is as defined in any one of paragraphs (10) to (29).

In one embodiment, X is as defined in any one of paragraphs (9), $R^2$ is as defined in any one of paragraphs (10) to (29).

In one embodiment, X is as defined in any one of paragraphs (5), $R^2$ is as defined in any one of paragraphs (10) to (29) and $R^1$ is as defined in any one of paragraphs (46) and (47).

In one embodiment, X is as defined in any one of paragraphs (7), $R^2$ is as defined in any one of paragraphs (10) to (29) and $R^1$ is as defined in any one of paragraphs (46) and (47).

In one embodiment, X is as defined in any one of paragraphs (9), $R^2$ is as defined in any one of paragraphs (10) to (29) and $R^1$ is as defined in any one of paragraphs (46) and (47).

In one embodiment, X is as defined in any one of paragraphs (5), $R^2$ is as defined in any one of paragraphs (10) to (29) and $R^1$ is as defined in paragraph (48).

In one embodiment, X is as defined in any one of paragraphs (7), $R^2$ is as defined in any one of paragraphs (10) to (29) and $R^1$ is as defined in paragraph (48).

In one embodiment, X is as defined in any one of paragraphs (9), $R^2$ is as defined in any one of paragraphs (10) to (29) and $R^1$ is as defined in paragraph (48).

In one embodiment, X is as defined in any one of paragraphs (5), $R^2$ is as defined in any one of paragraphs (10) to (29) and $R^1$ is as defined in paragraph (52).

In one embodiment, X is as defined in any one of paragraphs (7), $R^2$ is as defined in any one of paragraphs (10) to (29) and $R^1$ is as defined in paragraph (52).

In one embodiment, X is as defined in any one of paragraphs (9), $R^2$ is as defined in any one of paragraphs (10) to (29) and $R^1$ is as defined in paragraph (52).

In one embodiment, the compound of the present invention is according to any one of paragraphs (31), (36), (38), (40), (43) to (49) wherein $R^a$ is selected from hydrogen, hydroxyl, halogen, COOR$^3$, $C_1$-$C_6$alkyl, $C_0$-$C_6$alkylaryl, $C_0$-$C_6$alkylcycloalkyl, $C_0$-$C_6$alkylheterocycloalkyl, $C_0$-$C_6$alkylheteroaryl, $C_0$-$C_6$alkylCN, haloC$_1$-$C_6$alkyl, NO$_2$, $C_0$-$C_6$alkylNR$^3$R$^4$, —OCN, and —SCN, wherein any of the foregoing is optionally substituted with one or more R$^5$ groups.

In one embodiment, the compound of the present invention is according to any one of paragraphs (31), (36), (38), (40), (43) to (49) wherein $R^a$ is selected from hydrogen, hydroxyl, halogen, $C_1$-$C_3$alkyl, —OCN, —SCN, —CN and haloC$_1$-$C_3$alkyl.

In one embodiment, the compound of the present invention is according to any one of paragraphs (31), (36), (38), (40), (43) to (49) wherein $R^a$ is selected from hydrogen, hydroxyl, fluoro, chloro, methyl, ethyl, trifluoromethyl, NO$_2$, CN, OCN, SCN and difluoromethyl.

In one embodiment, the compound of the present invention is according to any one of paragraphs (31), (36), (38), (40), (43) to (49) wherein $R^a$ is selected from hydrogen, hydroxyl, fluoro, chloro, methyl, ethyl, trifluoromethyl, and difluoromethyl.

In one embodiment, the compound of the present invention is according to any one of paragraphs (31), (36), (38), (40), (43) to (49) wherein $R^a$ is selected from chloro and methyl.

In one embodiment, the compound of the present invention is according to any one of paragraphs (37), (39), (41), (46) to (49) wherein $R^e$ is selected from hydrogen, hydroxyl, halogen, COOR$^3$, $C_1$-$C_6$alkyl, $C_0$-$C_6$alkylaryl, $C_0$-$C_6$alkylcycloalkyl, $C_0$-$C_6$alkylheterocycloalkyl, $C_0$-$C_6$alkylheteroaryl, $C_0$-$C_6$alkylCN, haloC$_1$-$C_6$alkyl, NO$_2$, $C_0$-$C_6$alkylNR$^3$R$^4$, —OCN, and —SCN, wherein any of the foregoing is optionally substituted with one or more R$^5$ groups.

In one embodiment, the compound of the present invention is according to any one of paragraphs (37), (39), (41), (46) to (49) wherein $R^e$ is selected from hydrogen, hydroxyl, halogen, $C_1$-$C_3$alkyl, —OCN, —SCN, —CN and haloC$_1$-$C_3$alkyl.

In one embodiment, the compound of the present invention is according to any one of paragraphs (37), (39), (41), (46) to (49) wherein $R^e$ is selected from hydrogen, hydroxyl, fluoro, chloro, methyl, ethyl, trifluoromethyl, NO$_2$, CN, OCN, SCN and difluoromethyl.

In one embodiment, the compound of the present invention is according to any one of paragraphs (37), (39), (41), (46) to (49) wherein $R^e$ is selected from hydrogen, hydroxyl, fluoro, chloro, methyl, ethyl, trifluoromethyl, and difluoromethyl.

In one embodiment, the compound of the present invention is according to any one of paragraphs (37), (39), (41), (46) to (49) wherein $R^e$ is selected from chloro and methyl.

In one embodiment, the compound of the present invention is according to any one of paragraphs (34) to (37), (40) and (41) wherein $R^b$ is selected from hydrogen or methyl.

In one embodiment, the compound of the invention is according to any one of paragraphs (13) to (29) and (48) wherein each $R^5$ is independently selected from halogen, hydroxyl, OR$^6$, $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —C$_0$-C$_6$alkylCN, —C$_0$-C$_6$alkylC(=O)C$_0$-C$_6$alkylR$^6$, —C$_0$-C$_6$alkylC(=O)C$_0$-C$_6$alkylOR$^6$, —C$_0$-C$_6$alkylC(=O)C$_0$-C$_6$alkylNR$^6$R$^6$, —C$_0$-C$_6$alkylC(=O)C$_0$-C$_6$alkylNR$^6$C(=O)OR$^6$, haloC$_1$-C$_6$alkyl and NO$_2$, wherein each of the foregoing is optionally substituted with R$^7$, or together with carbon atoms to which they are attached, two R$^5$ groups are linked to form a fused aryl, heteroaryl, 3 to 6 membered heterocycloalkyl or a 3 to 6 membered cycloalkyl;

In one embodiment, the compound of the invention is according to any one of paragraphs (13) to (29) and (48) wherein each R$^5$ is halogen, hydroxyl, OR$^6$, $C_1$-$C_{10}$alkyl, $C_2$-$C_{10}$alkenyl, $C_2$-$C_{10}$alkynyl, $C_0$-$C_6$alkylaryl, $C_0$-$C_6$alkylcycloalkyl, $C_0$-$C_6$alkylheterocycloalkyl, $C_0$-$C_6$alkylheteroaryl, —C$_0$-C$_6$alkylCN, haloC$_1$-C$_6$alkyl and NO$_2$, wherein each of the foregoing is optionally substituted with R$^7$, or together with carbon atoms to which they are attached, two R$^5$ groups are linked to form a fused aryl, heteroaryl, 3 to 6 membered heterocycloalkyl or a 3 to 6 membered cycloalkyl;

In one embodiment, the compound of the invention is according to any one of paragraphs (13) to (29) and (48) wherein each R$^5$ is halogen, hydroxyl, OR$^6$, $C_1$-$C_{10}$alkyl, $C_0$-$C_6$alkylaryl, $C_0$-$C_6$alkylcycloalkyl, $C_0$-$C_6$alkylheterocycloalkyl, $C_0$-$C_6$alkylheteroaryl, —C$_0$-C$_6$alkylCN, haloC$_1$-C$_6$alkyl and NO$_2$, wherein each of the foregoing is optionally substituted with R$^7$, or together with carbon atoms to which they are attached, two R$^5$ groups are linked to form a fused aryl, heteroaryl, 3 to 6 membered heterocycloalkyl or a 3 to 6 membered cycloalkyl;

In one embodiment, the compound of the invention is according to any one of paragraphs (13) to (29) and (48) wherein each R$^5$ is halogen, hydroxyl, OR$^6$, $C_1$-$C_6$alkyl, $C_0$-$C_6$alkylaryl, $C_0$-$C_6$alkylcycloalkyl, $C_0$-$C_6$alkylheterocycloalkyl, $C_0$-$C_6$alkylheteroaryl, —C$_0$-C$_6$alkylCN, haloC$_1$-C$_6$alkyl and NO$_2$, wherein each of the foregoing is optionally substituted with R$^7$.

In one embodiment, the compound of the invention is according to any one of paragraphs (13) to (29) and (48) wherein each R$^5$ is selected from halogen, hydroxyl, OR$^6$, $C_1$-$C_{10}$alkyl, —C$_0$-C$_6$alkylC(=O)C$_0$-C$_6$alkylR$^6$, —C$_0$-C$_6$alkylC(=O)C$_0$-C$_6$alkylOR$^6$, haloC$_1$-C$_6$alkyl, —C$_0$-C$_6$alkylOR$^6$ and (=O), wherein each of the foregoing is optionally substituted with R$^7$.

In one embodiment, the compound of the invention is according to any one of paragraphs (13) to (29) and (48) wherein each R$^5$ is selected from halogen, hydroxyl, $C_1$-$C_3$alkyl, haloC$_1$-C$_6$alkyl and (=O).

In one embodiment, the compound of the invention is according to any one of paragraphs (13) to (29) and (48) wherein each R$^5$ is selected from $C_1$-$C_4$alkyl, haloC$_1$-C$_3$alkyl or halogen.

In one embodiment, the compound of the invention is according to any one of paragraphs (13) to (29) and (48) wherein each R$^5$ is selected from fluoro, chloro, methyl, trifluoromethyl and difluoromethyl.

In another embodiment, the present invention relates to a subgenus of Formula I, Formula Ib:

Formula Ib

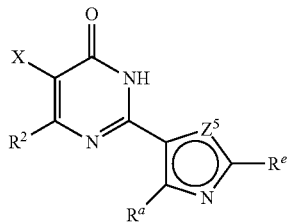

or a salt or solvate thereof wherein,

X is chosen from halogen, haloC$_1$-C$_6$alkyl and CN;

R$^2$ is selected from:

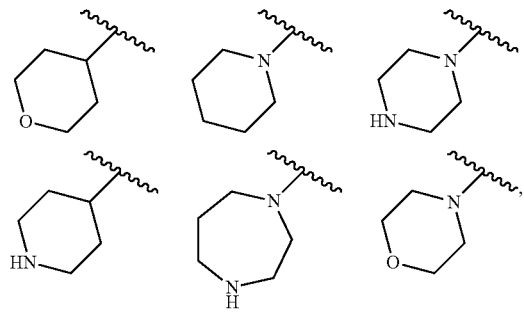

each optionally substituted with one of more R$^5$ group;

R$^5$ is selected from halogen, hydroxyl, C$_1$-C$_3$alkyl, haloC$_1$-C$_6$alkyl and (=O);

Z$^5$ is selected from O, N and S; and

R$^e$ and R$^a$ are independently selected from hydrogen, hydroxyl, halogen, C$_1$-C$_3$alkyl, —OCN, —SCN, —CN and haloC$_1$-C$_3$alkyl.

Particular embodiments of the invention include, for example, compounds of the formula Ib, or salts and/or solvates thereof, wherein alternative definitions of each of X, R$^2$, R$^a$, R$^e$ and Z$^5$ are defined in the following numbered paragraphs. Where not described otherwise, substituents have the same meaning as described for formula Ib above.

1) X is chosen from halogen, haloC$_1$-C$_2$alkyl, and CN;
2) X is chosen from halogen, CF$_3$, and CN;
3) X is chosen from fluoro, chloro, bromo, iodo and CN.
4) X is a halogen;
5) X is chosen from fluoro or chloro;
6) X is chloro;
7) R$^2$ is selected from

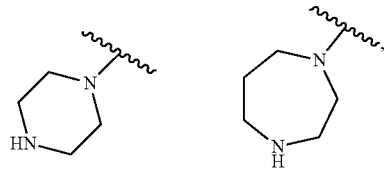

each optionally substituted with one of more R$^5$ group.

8) R$^2$ is selected from

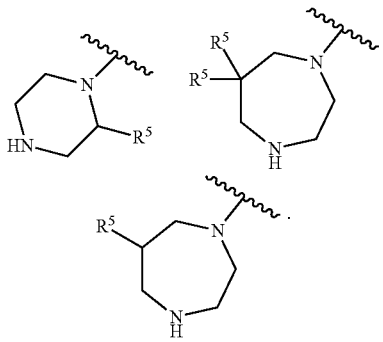

9) Z$^5$ is O or S
10) Z$^5$ is S
11) R$^a$ and R$^e$ are independently selected from hydrogen, hydroxyl, fluoro, chloro, methyl, ethyl, trifluoromethyl, and difluoromethyl.
12) R$^a$ and R$^e$ are independently selected from hydrogen, chloro and methyl.

In one embodiment, the compound of the invention is a compound of formula Ib according to any one of paragraphs (1) to (12) above wherein R$^e$ is hydrogen.

In one embodiment, the compound of the invention is a compound of formula Ib according to any one of paragraphs (1) to (12) above wherein R$^a$ is selected from chloro and methyl.

In one embodiment, the compound of the invention is a compound of formula Ib according to any one of paragraphs (7) and (8) above wherein R$^5$ is selected from fluoro, chloro, methyl, trifluoromethyl and difluoromethyl.

In another embodiment, the present invention relates to a subgenus of Formula I, Formula Ic:

Formula Ic

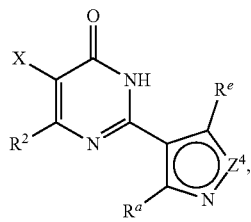

or a salt or solvate thereof wherein,

X is chosen from halogen, haloC$_1$-C$_6$alkyl and CN;

R$^2$ is selected from:

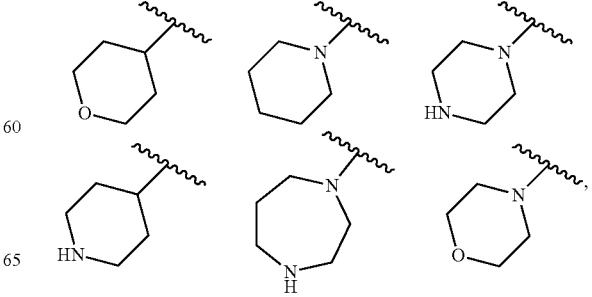

each optionally substituted with one of more R⁵ group;
R⁵ is selected from halogen, hydroxyl, $C_1$-$C_3$alkyl, halo$C_1$-$C_6$alkyl and (=O);
$Z^4$ is selected from $CR^e$, $NR^d$, O and S; and
$R^e$ and $R^a$ are independently selected from hydrogen, hydroxyl, halogen, $C_1$-$C_3$alkyl, —OCN, —SCN, —CN and halo$C_1$-$C_3$alkyl.

Particular embodiments of the invention include, for example, compounds of the formula Ic, or salts and/or solvates thereof, wherein alternative definitions of each of X, $R^2$, $R^a$, $R^e$ and $Z^5$ are defined in the following numbered paragraphs. Where not described otherwise, substituents have the same meaning as described for formula Ic above.
1) X is chosen from halogen, halo$C_1$-$C_2$alkyl, and CN;
2) X is chosen from halogen, $CF_3$, and CN;
3) X is chosen from fluoro, chloro, bromo, iodo and CN.
4) X is a halogen;
5) X is chosen from fluoro or chloro;
6) X is chloro;
7) $R^2$ is selected from

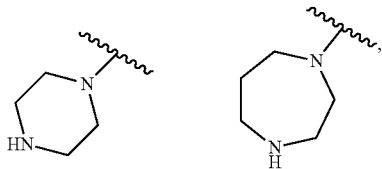

each optionally substituted with one of more R⁵ group.
8) $R^2$ is selected from

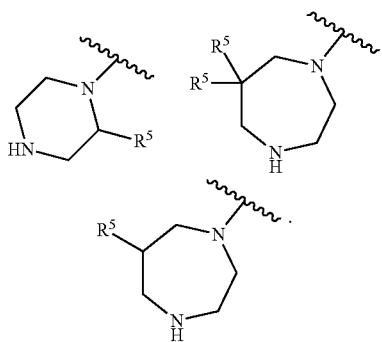

9) $Z^4$ is O, S or $NR^d$
10) $Z^4$ is $NR^d$
11) $R^d$ is methyl or hydrogen
12) $Z^4$ is NH
13) $R^a$ and $R^e$ are independently selected from hydrogen, hydroxyl, fluoro, chloro, methyl, ethyl, trifluoromethyl, and difluoromethyl.
14) $R^a$ and $R^e$ are independently selected from hydrogen, chloro, $CF_3$ and methyl.

In one embodiment, the compound of the invention is a compound of formula Ic according to any one of paragraphs (1) to (14) above wherein $R^e$ is methyl, ethyl, $CF_3$, chloro.

In one embodiment, the compound of the invention is a compound of formula Ic according to any one of paragraphs (1) to (14) above wherein $R^a$ is selected from hydrogen, fluoro, chloro, methyl, trifluoromethyl and difluoromethyl.

In one embodiment, the compound of the invention is a compound of formula Ic according to any one of paragraphs (1) to (14) above wherein $R^a$ is hydrogen and $R^e$ is selected from chloro, methyl, ethyl and trifluoromethyl.

In one embodiment, the compound of the invention is a compound of formula Ic according to any one of paragraphs (7) and (8) above wherein R⁵ is selected from fluoro, chloro, methyl, trifluoromethyl and difluoromethyl.

In one embodiment, the present invention relates to a compound selected from:
tert-butyl 4-[5-chloro-2-(4-methylthiazol-5-yl)-6-oxo-1H-pyrimidin-4-yl]piperidine-1-carboxylate;
5-chloro-2-(4-methylthiazol-5-yl)-4-(4-piperidyl)-1H-pyrimidin-6-one;
5-chloro-4-[1-(2,2-difluorocyclopropanecarbonyl)-4-piperidyl]-2-(4-methylthiazol-5-yl)-1H-pyrimidin-6-one;
5-chloro-4-[1-(4-methylthiazole-5-carbonyl)-4-piperidyl]-2-(4-methylthiazol-5-yl)-1H-pyrimidin-6-one;
5-chloro-2-(4-methylthiazol-5-yl)-4-[1-(thiazole-4-carbonyl)-4-piperidyl]-1H-pyrimidin-6-one;
5-chloro-4-[1-(3-methyl-1H-pyrazole-5-carbonyl)-4-piperidyl]-2-(4-methylthiazol-5-yl)-1H-pyrimidin-6-one;
5-chloro-4-[1-(1,5-dimethylpyrazole-3-carbonyl)-4-piperidyl]-2-(4-methylthiazol-5-yl)-1H-pyrimidin-6-one;
5-chloro-4-[1-(2,5-dimethylpyrazole-3-carbonyl)-4-piperidyl]-2-(4-methylthiazol-5-yl)-1H-pyrimidin-6-one;
5-chloro-4-[1-(5-methylisoxazole-3-carbonyl)-4-piperidyl]-2-(4-methylthiazol-5-yl)-1H-pyrimidin-6-one;
5-chloro-2-(4-methylthiazol-5-yl)-4-[1-(pyridazine-4-carbonyl)-4-piperidyl]-1H-pyrimidin-6-one;
5-chloro-4-(1-isobutyl-4-piperidyl)-2-(4-methylthiazol-5-yl)-1H-pyrimidin-6-one;
5-chloro-2-(4-methylthiazol-5-yl)-4-tetrahydropyran-4-yl-1H-pyrimidin-6-one;
5-chloro-2-(5-ethyl-1H-pyrazol-4-yl)-4-tetrahydropyran-4-yl-1H-pyrimidin-6-one;
5-chloro-4-tetrahydropyran-4-yl-2-thiazol-5-yl-1H-pyrimidin-6-one;
5-chloro-2-(4-methylthiadiazol-5-yl)-4-tetrahydropyran-4-yl-1H-pyrimidin-6-one;
5-chloro-2-(4-methyloxazol-5-yl)-4-tetrahydropyran-4-yl-1H-pyrimidin-6-one;
5-fluoro-2-(4-methylthiazol-5-yl)-4-tetrahydropyran-4-yl-1H-pyrimidin-6-one;
5-bromo-2-(4-methylthiazol-5-yl)-4-tetrahydropyran-4-yl-1H-pyrimidin-6-one;
5-iodo-2-(4-methylthiazol-5-yl)-4-tetrahydropyran-4-yl-1H-pyrimidin-6-one;
2-(4-methylthiazol-5-yl)-6-oxo-4-tetrahydropyran-4-yl-1H-pyrimidine-5-carbonitrile;
5-chloro-2-(2-hydroxy-4-methyl-thiazol-5-yl)-4-tetrahydropyran-4-yl-1H-pyrimidin-6-one;
5-chloro-4-(4-hydroxy-1-piperidyl)-2-(4-methylthiazol-5-yl)-1H-pyrimidin-6-one;
5-chloro-4-(4-methyl-1-piperidyl)-2-(4-methylthiazol-5-yl)-1H-pyrimidin-6-one;
5-chloro-2-(4-methylthiazol-5-yl)-4-[3-(trifluoromethyl)piperazin-1-yl]-1H-pyrimidin-6-one;
5-chloro-4-[(3-methylpiperazin-1-yl]-2-(4-methylthiazol-5-yl)-1H-pyrimidin-6-one;
5-chloro-4-[(3R)-3-methylpiperazin-1-yl]-2-(4-methylthiazol-5-yl)-1H-pyrimidin-6-one;
5-chloro-4-[4-(hydroxymethyl)-1-piperidyl]-2-(4-methylthiazol-5-yl)-1H-pyrimidin-6-one;
4-[5-chloro-2-(4-methylthiazol-5-yl)-6-oxo-1H-pyrimidin-4-yl]-1,4-diazepan-2-one;
5-chloro-4-(3,3-difluoro-1-piperidyl)-2-(4-methylthiazol-5-yl)-1H-pyrimidin-6-one;

5-chloro-4-[3-(hydroxymethyl)-1-piperidyl]-2-(4-methylthiazol-5-yl)-1H-pyrimidin-6-one;
5-chloro-4-[(3S)-3-methylpiperazin-1-yl]-2-(4-methylthiazol-5-yl)-1H-pyrimidin-6-one;
5-chloro-2-(4-methylthiazol-5-yl)-4-piperazin-1-yl-1H-pyrimidin-6-one;
5-chloro-2-(4-ethylthiazol-5-yl)-4-tetrahydropyran-4-yl-1H-pyrimidin-6-one;
5-chloro-2-(3-methyl-1H-pyrazol-4-yl)-4-tetrahydropyran-4-yl-1H-pyrimidin-6-one;
5-chloro-2-(4-methylthiazol-5-yl)-4-[3-(trifluoromethyl)piperazin-1-yl]-1H-pyrimidin-6-one;
5-chloro-2-(4-methylthiazol-5-yl)-4-[(3R)-3-(trifluoromethyl)piperazin-1-yl]-1H-pyrimidin-6-one;
5-chloro-2-(4-chlorothiazol-5-yl)-4-tetrahydropyran-4-yl-1H-pyrimidin-6-one;
5-chloro-4-tetrahydropyran-4-yl-2-[4-(trifluoromethyl)thiazol-5-yl]-1H-pyrimidin-6-one;
5-chloro-4-[3-isopropylpiperazin-1-yl]-2-(4-methylthiazol-5-yl)-1H-pyrimidin-6-one;
5-chloro-4-[(3S)-3-isopropylpiperazin-1-yl]-2-(4-methylthiazol-5-yl)-1H-pyrimidin-6-one;
5-chloro-4-tetrahydropyran-4-yl-2-[5-(trifluoromethyl)-1H-pyrazol-4-yl]-1H-pyrimidin-6-one;
5-chloro-2-(2-methylpyrazol-3-yl)-4-tetrahydropyran-4-yl-1H-pyrimidin-6-one;
5-chloro-2-(5-methyl-1H-pyrazol-4-yl)-4-morpholino-1H-pyrimidin-6-one;
5-chloro-4-morpholino-2-[5-(trifluoromethyl)-1H-pyrazol-4-yl]-1H-pyrimidin-6-one;
5-chloro-4-[2-methylpiperazin-1-yl]-2-(5-methyl-1H-pyrazol-4-yl)-1H-pyrimidin-6-one;
5-chloro-4-[(2R)-2-methylpiperazin-1-yl]-2-(5-methyl-1H-pyrazol-4-yl)-1H-pyrimidin-6-one;
5-chloro-4-[3-methylmorpholin-4-yl]-2-(1H-pyrrolo[2,3-b]pyridin-3-yl)-1H-pyrimidin-6-one;
5-chloro-4-[(3R)-3-methylmorpholin-4-yl]-2-(1H-pyrrolo[2,3-b]pyridin-3-yl)-1H-pyrimidin-6-one;
5-chloro-4-[3-methylmorpholin-4-yl]-2-[5-(trifluoromethyl)-1H-pyrazol-4-yl]-1H-pyrimidin-6-one;
5-chloro-4-[(3R)-3-methylmorpholin-4-yl]-2-[5-(trifluoromethyl)-1H-pyrazol-4-yl]-1H-pyrimidin-6-one;
5-chloro-4-[2-methylpiperazin-1-yl]-2-[5-(trifluoromethyl)-1H-pyrazol-4-yl]-1H-pyrimidin-6-one;
5-chloro-4-[(2R)-2-methylpiperazin-1-yl]-2-[5-(trifluoromethyl)-1H-pyrazol-4-yl]-1H-pyrimidin-6-one;
5-chloro-4-[3-methylmorpholin-4-yl]-2-pyrazolo[1,5-a]pyridin-3-yl-1H-pyrimidin-6-one;
5-chloro-4-[(3R)-3-methylmorpholin-4-yl]-2-pyrazolo[1,5-a]pyridin-3-yl-1H-pyrimidin-6-one;
5-chloro-4-[2-methylpiperazin-1-yl]-2-(1H-pyrrolo[2,3-b]pyridin-3-yl)-1H-pyrimidin-6-one;
5-chloro-4-[(2R)-2-methylpiperazin-1-yl]-2-(1H-pyrrolo[2,3-b]pyridin-3-yl)-1H-pyrimidin-6-one;
5-chloro-4-(6,6-difluoro-1,4-diazepan-1-yl)-2-[5-(trifluoromethyl)-1H-pyrazol-4-yl]-1H-pyrimidin-6-one;
5-chloro-2-(5-chloro-1H-pyrazol-4-yl)-4-[(2R)-2-methylpiperazin-1-yl]-1H-pyrimidin-6-one;
5-chloro-4-(6,6-difluoro-1,4-diazepan-1-yl)-2-(1H-pyrrolo[2,3-b]pyridin-3-yl)-1H-pyrimidin-6-one;
5-chloro-4-(2,2-dimethylpiperazin-1-yl)-2-[5-(trifluoromethyl)-1H-pyrazol-4-yl]-1H-pyrimidin-6-one;
5-chloro-4-[2-methylpiperazin-1-yl]-2-(4-methylthiazol-5-yl)-1H-pyrimidin-6-one;
5-chloro-4-[(2R)-2-methylpiperazin-1-yl]-2-(4-methylthiazol-5-yl)-1H-pyrimidin-6-one;
5-chloro-2-(3-methylisoxazol-4-yl)-4-[(2R)-2-methylpiperazin-1-yl]-1H-pyrimidin-6-one;
5-chloro-4-[3-methylmorpholin-4-yl]-2-(4-methylthiazol-5-yl)-1H-pyrimidin-6-one;
5-chloro-4-[(3R)-3-methylmorpholin-4-yl]-2-(4-methylthiazol-5-yl)-1H-pyrimidin-6-one;
5-chloro-4-(6,6-difluoro-1,4-diazepan-1-yl)-2-(4-methylthiazol-5-yl)-1H-pyrimidin-6-one;
5-chloro-2-(5-chloro-1H-pyrazol-4-yl)-4-[3-methylmorpholin-4-yl]-1H-pyrimidin-6-one;
5-chloro-2-(5-chloro-1H-pyrazol-4-yl)-4-[(3R)-3-methylmorpholin-4-yl]-1H-pyrimidin-6-one;
5-chloro-2-(4-methylthiazol-5-yl)-4-[2-(trifluoromethyl)piperazin-1-yl]-1H-pyrimidin-6-one;
5-chloro-4-[2-(difluoromethyl)piperazin-1-yl]-2-(4-methylthiazol-5-yl)-1H-pyrimidin-6-one;
5-chloro-4-(6-fluoro-1,4-diazepan-1-yl)-2-(4-methylthiazol-5-yl)-1H-pyrimidin-6-one;
5-chloro-2-(4-chlorothiazol-5-yl)-4-[2-methylpiperazin-1-yl]-1H-pyrimidin-6-one;
5-chloro-2-(4-chlorothiazol-5-yl)-4-[(2R)-2-methylpiperazin-1-yl]-1H-pyrimidin-6-one;
5-chloro-4-[2-methylpiperazin-1-yl]-2-(2-methylpyrazol-3-yl)-1H-pyrimidin-6-one;
5-chloro-4-[(2R)-2-methylpiperazin-1-yl]-2-(2-methylpyrazol-3-yl)-1H-pyrimidin-6-one;
5-chloro-2-(4-chlorothiazol-5-yl)-4-[3-methylmorpholin-4-yl]-1H-pyrimidin-6-one;
5-chloro-2-(4-chlorothiazol-5-yl)-4-[(3R)-3-methylmorpholin-4-yl]-1H-pyrimidin-6-one;
5-chloro-2-(4-chlorothiazol-5-yl)-4-(6,6-difluoro-1,4-diazepan-1-yl)-1H-pyrimidin-6-one;
5-chloro-2-(2-methylimidazol-1-yl)-4-[3-methylmorpholin-4-yl]-1H-pyrimidin-6-one;
5-chloro-2-(2-methylimidazol-1-yl)-4-[(3R)-3-methylmorpholin-4-yl]-1H-pyrimidin-6-one;
5-chloro-2-(5-chloro-1H-pyrazol-4-yl)-4-(6,6-difluoro-1,4-diazepan-1-yl)-1H-pyrimidin-6-one;
5-chloro-4-(6,6-difluoro-1,4-diazepan-1-yl)-2-[4-(trifluoromethyl)thiazol-5-yl]-1H-pyrimidin-6-one;
5-chloro-2-(4-chlorothiazol-5-yl)-4-[2-(difluoromethyl)piperazin-1-yl]-1H-pyrimidin-6-one;
5-chloro-2-(4-chlorothiazol-5-yl)-4-[2-(trifluoromethyl)piperazin-1-yl]-1H-pyrimidin-6-one;
5-chloro-2-(4-chlorothiazol-5-yl)-4-(6-fluoro-1,4-diazepan-1-yl)-1H-pyrimidin-6-one;
5-chloro-2-(4-chlorothiazol-5-yl)-4-[2-(difluoromethyl)piperazin-1-yl]-1H-pyrimidin-6-one;
5-chloro-2-(4-chlorothiazol-5-yl)-4-[(2S)-2-(difluoromethyl)piperazin-1-yl]-1H-pyrimidin-6-one;
5-chloro-2-(4-chlorothiazol-5-yl)-4-[(2R)—R-(difluoromethyl)piperazin-1-yl]-1H-pyrimidin-6-one;
5-chloro-2-(4-chlorothiazol-5-yl)-4-[6-fluoro-1,4-diazepan-1-yl]-1H-pyrimidin-6-one;
5-chloro-2-(4-chlorothiazol-5-yl)-4-[(6S)-6-fluoro-1,4-diazepan-1-yl]-1H-pyrimidin-6-one;
5-chloro-2-(4-chlorothiazol-5-yl)-4-[(6R)-6-fluoro-1,4-diazepan-1-yl]-1H-pyrimidin-6-one, or a salt or solvate thereof.

In another embodiment, the present invention relates to a compound selected from 5-chloro-2-(4-chlorothiazol-5-yl)-4-[2-methylpiperazin-1-yl]-1H-pyrimidin-6-one;
5-chloro-2-(4-chlorothiazol-5-yl)-4-[(2R)-2-methylpiperazin-1-yl]-1H-pyrimidin-6-one;
5-chloro-2-(4-chlorothiazol-5-yl)-4-[3-methylmorpholin-4-yl]-1H-pyrimidin-6-one;

5-chloro-2-(4-chlorothiazol-5-yl)-4-[(3R)-3-methylmorpholin-4-yl]-1H-pyrimidin-6-one;
5-chloro-2-(4-chlorothiazol-5-yl)-4-(6,6-difluoro-1,4-diazepan-1-yl)-1H-pyrimidin-6-one;
5-chloro-2-(4-chlorothiazol-5-yl)-4-[2-(difluoromethyl)piperazin-1-yl]-1H-pyrimidin-6-one;
5-chloro-2-(4-chlorothiazol-5-yl)-4-[2-(trifluoromethyl)piperazin-1-yl]-1H-pyrimidin-6-one;
5-chloro-2-(4-chlorothiazol-5-yl)-4-(6-fluoro-1,4-diazepan-1-yl)-1H-pyrimidin-6-one;
5-chloro-2-(4-chlorothiazol-5-yl)-4-[2-(difluoromethyl)piperazin-1-yl]-1H-pyrimidin-6-one;
5-chloro-2-(4-chlorothiazol-5-yl)-4-[(2S)-2-(difluoromethyl)piperazin-1-yl]-1H-pyrimidin-6-one;
5-chloro-2-(4-chlorothiazol-5-yl)-4-[(2R)— R-(difluoromethyl)piperazin-1-yl]-1H-pyrimidin-6-one;
5-chloro-2-(4-chlorothiazol-5-yl)-4-[6-fluoro-1,4-diazepan-1-yl]-1H-pyrimidin-6-one;
5-chloro-2-(4-chlorothiazol-5-yl)-4-[(6R)-6-fluoro-1,4-diazepan-1-yl]-1H-pyrimidin-6-one;
5-chloro-2-(4-chlorothiazol-5-yl)-4-[(6S)-6-fluoro-1,4-diazepan-1-yl]-1H-pyrimidin-6-one,
or a salt or solvate thereof.

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Salts and Solvates

The compounds (including final products and intermediates) described herein may be isolated and used per se or may be isolated in the form of a salt, suitably pharmaceutically acceptable salts. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more.

Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved by the FDA or equivalent foreign regulatory body for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In one embodiment, the compounds of formula are isolated as pharmaceutically acceptable salts.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of the formula I may exist in solvated as well as unsolvated forms such as, for example, hydrated forms. It is to be understood that the invention encompasses all such solvated forms that possess antiproliferative activity.

Polymorphs

It is also to be understood that certain compounds of the formula I may exhibit polymorphism, and that the invention encompasses all such forms that possess antiproliferative activity.

N-oxides

Compounds of the formula I containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

Tautomers

Compounds of the formula I may exist in a number of different tautomeric forms and references to compounds of the formula I include all such forms. For the avoidance of doubt, where a compound can exist in one of several tautomeric forms, and only one is specifically described or shown, all others are nevertheless embraced by formula I. Examples of tautomeric forms include keto-, enol-, and enolate-forms, as in, for example, the following tautomeric pairs: keto/enol (illustrated below), pyrimidone/hydroxypyrimidine, imine/enamine, amide/imino alcohol, amidine/amidine, nitroso/oxime, thioketone/enethiol, and nitro/aci-nitro.

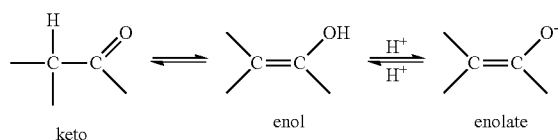

keto      enol      enolate

Isomers

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

Certain compounds of Formula I may have one or more asymmetric centers and therefore can exist in a number of stereoisomeric configurations. Consequently, such compounds can be synthesized and/or isolated as mixtures of enantiomers and/or as individual (pure) enantiomers, and, in the case of two or more asymmetric centers, single diastereomers and/or mixtures of diastereomers. It should be understood that the present application includes all such enantiomers and diastereomers and mixtures thereof in all ratios.

Isotopes

The compounds of the present invention are described herein using structural formulas that do not specifically recite the mass numbers or the isotope ratios of the constituent atoms. As such it is intended that the present application includes compounds in which the constituent atoms are present in any ratio of isotope forms. For example, carbon atoms may be present in any ratio of $^{12}C$, $^{13}C$, and $^{14}C$; hydrogen atoms may be present in any ratio of $^{1}H$, $^{2}H$, and $^{3}H$; etc. Preferably, the constituent atoms in the compounds of the present invention are present in their naturally occurring ratios of isotope forms.

Prodrugs and Metabolites

The compounds of formula I may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula I and in-vivo cleavable amide derivatives that may be formed at a carboxy group or an amino group in a compound of the formula I.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents: — a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-4}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the person skilled in the art. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as inhibitors of Cdc7.

The present invention therefore provides a method of inhibiting Cdc7 enzyme activity in vitro or in vivo, said method comprising contacting a cell with an effective amount of a compound, or a pharmaceutically acceptable salt, hydrate or solvate thereof, as defined herein.

The present invention also provides a method of treating a disease or disorder in which Cdc7 activity is implicated in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of inhibiting cell proliferation, in vitro or in vivo, said method comprising contacting a cell with an effective amount of a compound, or a pharmaceutically acceptable salt, hydrate or solvate thereof, as defined herein.

The present invention provides a method of treating a proliferative disorder in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of treating cancer in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a compound, or a pharmaceutically acceptable salt, hydrate or solvate thereof, or a pharmaceutical composition as defined herein for use in therapy.

The present invention provides a compound, or a pharmaceutically acceptable salt, hydrate or solvate thereof, or a pharmaceutical composition as defined herein for use in the treatment of a proliferative condition.

The present invention provides a compound, or a pharmaceutically acceptable salt, hydrate or solvate thereof, or a pharmaceutical composition as defined herein for use in the treatment of cancer. In a particular embodiment, the cancer is human cancer.

The present invention provides a compound, or a pharmaceutically acceptable salt, hydrate or solvate thereof, as defined herein for use in the inhibition of Cdc7 enzyme activity.

The present invention provides a compound, or a pharmaceutically acceptable salt, hydrate or solvate thereof, as defined herein for use in the treatment of a disease or disorder in which Cdc7 activity is implicated.

The present invention provides a use of a compound, or a pharmaceutically acceptable salt, hydrate or solvate thereof, as defined herein in the manufacture of a medicament for the treatment of a proliferative condition.

The present invention provides a use of a compound, or a pharmaceutically acceptable salt, hydrate or solvate thereof, as defined herein in the manufacture of a medicament for the treatment of cancer. Suitably, the medicament is for use in the treatment of human cancers.

The present invention provides a use of a compound, or a pharmaceutically acceptable salt, hydrate or solvate thereof, as defined herein in the manufacture of a medicament for the inhibition of Cdc7 enzyme activity.

The present invention provides a use of a compound, or a pharmaceutically acceptable salt, hydrate or solvate thereof, as defined herein in the manufacture of a medicament for the treatment of a disease or disorder in which Cdc7 activity is implicated.

The term "proliferative disorder" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers (by virtue of their inhibition of Cdc7 enzyme activity).

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

In a particular embodiment of the invention, the proliferative condition to be treated is cancer. For example, lung cancer, colon cancer, breast cancer, ovarian cancer, prostate cancer, liver cancer, pancreatic cancer, brain cancer and skin cancer.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents: —

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, $C_{225}$] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination. In one embodiment, a combination refers to a combination product.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

EXAMPLES

Chemistry

The following examples are provided solely to illustrate the present invention and are not intended to limit the scope of the invention, as described herein.

The compounds of the invention may be prepared using synthetic techniques that are known in the art (as illustrated by the examples herein).

For convenience, the following common abbreviations are used herein:
Boc for tert-butyloxycarbonyl
DAST for diethylaminosulfur trifluoride
DBU for 1,8-diazabicyclo(5.4.0)undec-7-ene
DCM for dichloromethane
DEA for diethanolamine
DIPEA for N,N-diisopropylethylamine, Hünig's base
DMA for N,N-dimethylacetamide
DMF for N,N-dimethylformamide
DMSO for dimethylsulfoxide.
h for hours
HBTU for O-(benzotriazol-1-yl)-N,N,N',N'-tetramethyluronium hexafluorophosphate
HPLC for High Pressure Liquid Chromatography.
IPA for isopropyl alcohol
LCMS for Liquid Chromatography-Mass Spectrometry.
MI for Molecular Ion
Min for minutes
MW for microwave
NBS for N-bromosuccinamide
NCS for N-chlorosuccinamide
NIS for N-iodosuccinamide
NMM for N-methylmorpholine
NMP for 1-methyl-2-pyrrolidinone
NMR for Nuclear Magnetic Resonance.
p-TSA for para-toluenesulfonic acid
Pd(dppf)$C_2$ for [1,1'-bis(diphenylphosphino)ferrocene]dichloropalladium(II)
Pd(dba)$_2$ for bis(dibenzylideneacetone)palladium
RT for Retention Time.
SCX-2 for a silica-based sorbent with a chemically bonded propylsulfonic acid functional group
SFC for supercritical fluid chromatography
TBME for tert-butylmethyl ether
TFA for trifluoroacetic acid
THF for tetrahydrofuran
THP for tetrahydropyran General Methods: NMR Proton NMR spectra were recorded using a Bruker AMX-300 NMR machine at 300 MHz, a Bruker AMX-400 NMR machine at 400 MHz or a Bruker Avance 500 machine at 500 MHz. Shifts were reported in ppm values relative to an internal standard of tetramethylsilane (TMS) or residual protic solvent. The following abbreviations were used to describe the splitting patterns: s (singlet), d (doublet), t (triplet), q (quartet), m (multiplet), dd (double-doublet), dt (double-triplet), br (broad).

General Methods: LCMS Methods

Method: 1 LCMS1

Method 1LCMS1 employed Waters 515 pumps, a Waters 2525 mixer with valves directing to the different columns and a Waters 2487 diode array detector. The detection was performed at 254 nm. The mass spectrometer was a Waters micromass ZQ which detected masses between 100 and 700 g/mol. The column used was a SunFire, 5 micron pore size, C18 column of dimensions 50×4.60 mm. The injection volume was 10 µL at a maximum concentration of 1 mg/mL. The flow rate was 1.5 mL/min and the mobile phases of water and methanol contained 0.1% formic acid. The elution was started at 85% water:15% methanol ramping up to 15% water:85% methanol over 4.5 minutes, these conditions were held for 1 minute before the eluent level was returned to the starting conditions of 85% water:15% methanol over 6 seconds. These conditions were held for 1.4 minutes to allow equilibration of the column before the next sample was injected. The run lasted 7 minutes in total.

Method: 1 LCMS12

Method 1LCMS12 employed Waters 515 pumps, a Waters 2525 mixer with valves directing to the different columns and a Waters 2998 diode array detector. The detection was performed between 210 nm and 400 nm. The mass spectrometer was a Waters micromass ZQ which detected masses between 100 and 700 g/mol. The column used was a SunFire, 5 micron pore size, C18 column of dimensions 50×4.60 mm. The injection volume was 10 µL at a maximum concentration of 1 mg/mL. The flow rate was 1.5 mL/min and the mobile phases of water and acetonitrile contained 0.1% formic acid. The elution was started at 95% water:5% acetonitrile ramping up to 5% water:95% acetonitrile over 5 minutes, these conditions were held for 0.5 min before the eluent level was returned to the starting conditions of 95% water:5% acetonitrile over 6 seconds. These conditions were held for 1.4 minutes to allow equilibration of the column before the next sample was injected. The run lasted 7 minutes in total.

Method: 1 LCMS13

Method 1LCMS13 employed Waters 515 pumps, a Waters 2525 mixer with valves directing to the different columns and a Waters 2998 diode array detector. The detection was performed between 210 nm and 400 nm. The mass spectrometer was a Waters micromass ZQ which detected masses between 100 and 700 g/mol. The column used was a SunFire, 5 micron pore size, C18 column of dimensions 50×4.60 mm. The injection volume was 10 µL at a maximum concentration of 1 mg/mL. The flow rate was 1.5 mL/min and the mobile phases of water and acetonitrile contained 0.1% formic acid. The elution was started at 95% water:5% acetonitrile ramping up to 5% water:95% acetonitrile over 2.5 minutes, these conditions were held for 3 min before the eluent level was returned to the starting conditions of 95% water:5% acetonitrile over 18 seconds. These conditions were held for 1.2 minutes to allow equilibration of the column before the next sample was injected. The run lasted 7 minutes in total.

Method: 2LCMS1

Method 2LCMS1 employed Waters 515 pumps, a Waters 2545 mixer with valves directing to the different columns and a Waters 2996 diode array detector. The detection was performed between 210 nm and 650 nm. The mass spectrometer was a Waters 3100 which detected masses between 100 and 700 g/mol. The column used was an XBridge, 5 micron pore size, C18, 50×4.60 mm. The injection volume was 10 μL at a maximum concentration of 1 mg/mL. The flow rate was 1.5 mL/min and the mobile phases of water pH 10 (35% ammonia solution (aq) 0.3 mL/L) and methanol (35% ammonia solution (aq) 0.3 mL/L). The elution was started at 85% water:15% methanol ramping up to 15% water:85% methanol over 4.5 minutes. These conditions were held for 1 minute before the eluent level was returned to the starting conditions of 85% water:15% methanol over 6 seconds. These conditions were held for 1.4 minutes to allow equilibration of the column before the next sample was injected. The run lasted 7 minutes in total.

Method: 2LCMS5

Method 2LCMS5 employed Waters 515 pumps, a Waters 2545 mixer with valves directing to the different columns and a Waters 2996 diode array detector. The detection was performed between 210 nm and 650 nm. The mass spectrometer was a Waters 3100 which detected masses between 100 and 700 g/mol. The column used was an XBridge, 5 micron pore size, C18, 50×4.60 mm. The injection volume was 10 μL at a maximum concentration of 1 mg/mL. The flow rate was 1.5 mL/min and the mobile phases of water pH 10 (35% ammonia solution (aq) 0.3 mL/L) and acetonitrile (35% ammonia solution (aq) 0.3 mL/L). The elution was started at 95% water:5% acetonitrile ramping up to 5% water:95% acetonitrile over 5 minutes. These conditions were held for 0.5 minutes before the eluent level was returned to the starting conditions of 95% water:5% acetonitrile over 18 seconds. These conditions were held for 1.2 minutes to allow equilibration of the column before the next sample was injected. The run lasted 7 minutes in total.

Method: 4LCMS1

Method 4LCMS1 employed an Alliance e2695 liquid handler and SFO with a Waters 2998 diode array detector. The detection was done at 254 nm and an array between 210-600 nm. The mass spectrometer used was an Acquity SQ which detected masses between 100 and 700 g/mol. The column used was a SunFire, 5 micron pore size, C18 column of dimensions 50×4.60 mm. The injection volume was 10 μL at a maximum concentration of 1 mg/mL. The flow rate was 1.5 mL/min and the mobile phases of water and acetonitrile contained 0.1% formic acid. The elution was started at 95% water:5% acetonitrile ramping up to 5% water:95% acetonitrile over 5 minutes, these conditions were held for 0.5 min before the eluent level was returned to the starting conditions of 95% water:5% acetonitrile over 6 seconds. These conditions were held for 1.4 minutes to allow equilibration of the column before the next sample was injected. The run lasted 7 minutes in total.

Method: 4LCMS3

Method 4LCMS3 employed an Alliance e2695 liquid handler and SFO with a Waters 2998 diode array detector. The detection was done at 254 nm and an array between 210-600 nm. The mass spectrometer used was an Acquity SQ which detected masses between 100 and 700 g/mol. The column used was a SunFire, 5 micron pore size, C18 column of dimensions 50×4.60 mm. The injection volume was 10 μL at a maximum concentration of 1 mg/mL. The flow rate was 1.5 mL/min and the mobile phases of water and acetonitrile contained 0.1% formic acid. The elution was started at 95% water:5% acetonitrile ramping up to 5% water:95% acetonitrile over 2.25 minutes, these conditions were held for 2.8 min before the eluent level was returned to the starting conditions of 95% water:5% acetonitrile over 6 seconds. These conditions were held for 0.8 minutes to allow equilibration of the column before the next sample was injected. The run lasted 3.7 minutes in total.

Method: 4LCMS6

Method 4LCMS6 employed an Alliance e2695 liquid handler and SFO with a Waters 2998 diode array detector. The detection was done at 254 nm and an array between 210-600 nm. The mass spectrometer used was an Acquity SQ which detected masses between 100 and 700 g/mol. The column used was a Waters Cortecs, 2.7 micron pore size, C18 column of dimensions 50×4.60 mm used at a temperature of 45° C. The injection volume was 10 μL at a maximum concentration of 1 mg/mL. The flow rate was 2.2 mL/min and the mobile phases of water and acetonitrile contained 0.1% formic acid. The elution was started at 95% water:5% acetonitrile ramping up to 5% water:95% acetonitrile over 2.2 minutes, these conditions were held for 2.5 min before the eluent level was returned to the starting conditions of 95% water:5% acetonitrile over 6 seconds. These conditions were held for 0.6 minutes to allow equilibration of the column before the next sample was injected. The run lasted 3.2 minutes in total.

Method: 5LCMS1

Method 5LCMS1 employed Waters 515 pumps, a Waters 2525 mixer with valves directing to the different columns and a Waters 2998 diode array detector. The detection was performed at 254 nm and an array between 210-600 nm. The mass spectrometer used was a Waters 3100 which detected masses between 100 and 700 g/mol. The column used was a SunFire, 5 micron pore size, C18 column of dimensions 50×4.60 mm. The injection volume was 10 μL at a maximum concentration of 1 mg/mL. The flow rate was 1.5 mL/min and the mobile phases of water and acetonitrile contained 0.1% formic acid. The elution was started at 95% water:5% acetonitrile ramping up to 5% water:95% acetonitrile over 5 minutes, these conditions were held for 0.5 min before the eluent level was returned to the starting conditions of 95% water:5% acetonitrile over 6 seconds. These conditions were held for 1.4 minutes to allow equilibration of the column before the next sample was injected. The run lasted 7 minutes in total.

Synthesis

Several methods for the chemical synthesis of the present application are described herein. These and/or other well-known methods may be modified and/or adapted in various ways in order to facilitate the synthesis of additional compounds within the scope of the present application and claims. Such alternative methods and modifications should be understood as being within the spirit and scope of this application and claims. Accordingly, it should be understood that the methods set forth in the following descriptions, schemes and examples are intended for illustrative purposes and are not to be construed as limiting the scope of the disclosure.

In one approach (General Scheme 1), compounds of formula [F1-3] are prepared by the reaction of a 3-substituted β-ketopropyl ester compound of formula [F1-1] in a condensation reaction utilising a suitably substituted heterocyclic carboximidamide derivative of general formula [F1-2] in a polar solvent such as methanol or THF in the presence of a base such as sodium methoxide or DBU. The reaction is suitably conducted at ambient temperature or at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. Derivatives of general formula [F1-5] are prepared by the reaction of compounds of formula [F1-3] with a halogenating agent such as NCS or NBS in a polar solvent such as DMF or THF and a base such as Et$_3$N or DIPEA at ambient temperature. After reaction work up, typically by a liquid-liquid extraction, the reaction product was used crude in the next step or purified by flash column chromatography, reverse phase preparative HPLC or re-crystallisation.

Alternatively, compounds of formula [F1-5] are prepared by the reaction of a 2,3-disubstituted β-ketopropyl ester compound of formula [F1-4] in a condensation reaction utilising a suitably substituted heterocyclic carboximidamide derivative of general formula [F1-2] in a polar solvent such as methanol or THF in the presence of a base such as sodium methoxide or DBU. The reaction is suitably conducted at ambient temperature or at high temperature either by heating thermally or using a microwave reactor. After reaction work up, typically by a liquid-liquid extraction, the reaction product was used crude in the next step or purified by flash column chromatography, reverse phase preparative HPLC or re-crystallisation.

In cases where the substituent R$^2$ contained an amine protected by a standard amine protecting group such as tert-butyloxycarbonyl (Boc), compounds of formula [F1-5] can be deprotected by a suitable deprotection reaction, for example reaction with an acid such as TFA in a suitable solvent such as DCM at ambient temperature. After reaction work up, typically by a liquid-liquid extraction or purification by acidic ion exchange catch-release the crude product can be purified by flash column chromatography, reverse phase preparative HPLC or re-crystallisation.

General Scheme 1

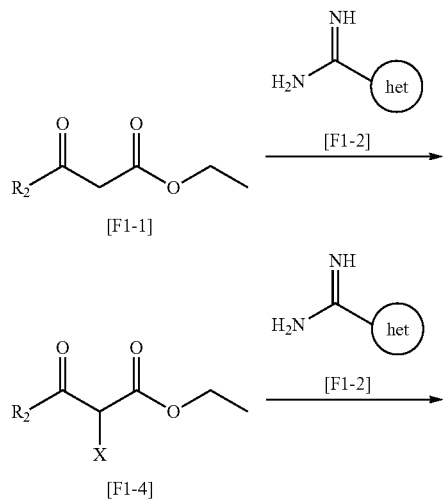

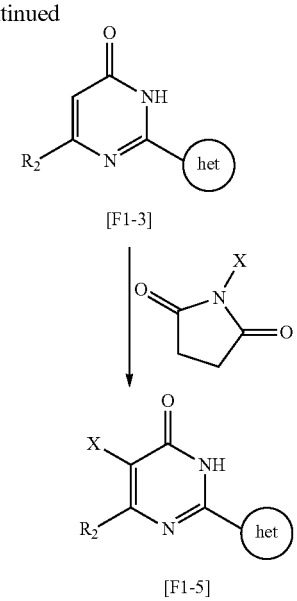

Synthesis of 4-methylthiazole-5-carboxamidine hydrochloride (1-001)

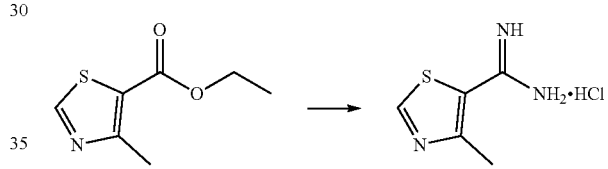

Ammonium chloride (7.81 g, 146 mmol) was suspended in toluene (50 mL) under nitrogen and cooled to 0° C. Trimethylaluminium solution (2.0 M in toluene, 62.5 mL, 125 mmol) was added dropwise to the reaction mixture keeping the temperature below 10° C. Once the addition was completed, the reaction mixture was allowed to warm to room temperature and stirred for 1 hour. The reaction was then heated to reflux for 18 h before cooling to room temperature. Ethyl 4-methyl-1,3-thiazole-5-carboxylate (2.50 g, 14.6 mmol) was added and the reaction heated to reflux for 7 hours. The reaction mixture was cooled to room temperature and another batch of ethyl 4-methyl-1,3-thiazole-5-carboxylate (2.50 g, 14.6 mmol) was added. The reaction mixture was heated to reflux for 18 h then cooled to room temperature and another batch of ethyl 4-methyl-1,3-thiazole-5-carboxylate (2.50 g, 14.6 mmol) was added. The reaction was heated to reflux for a further 24 h then cooled to room temperature. The reaction mixture was added slowly to MeOH (100 mL) under vigorous stirring (exotherm observed). The obtained thick precipitate was filtered onto a glass fibre filtration sheet under a nitrogen flow. The pad was washed with MeOH and the combined filtrate was concentrated under vacuum. The residue was sonicated for 15 min in DCM (50 mL), then stirred vigorously to break up the crystals. The suspension was filtered through a sintered funnel to give an off-white solid. The collected solid was dried in a vacuum oven at 50° C. for 1 h to afford the title compound (4.0 g, 51%). LCMS: MI 143, Method (1LCMS1); $^1$H NMR (500 MHz, DMSO-d$_6$) δ 9.51 (br s, 3H), 9.30 (s, 1H), 7.70 (br s, 3H), 2.54 (s, 3H).

Synthesis of tert-butyl 4-[5-chloro-2-(4-methylthiazol-5-yl)-6-oxo-1H-pyrimidin-4-yl]piperidine-1-carboxylate (1-002)

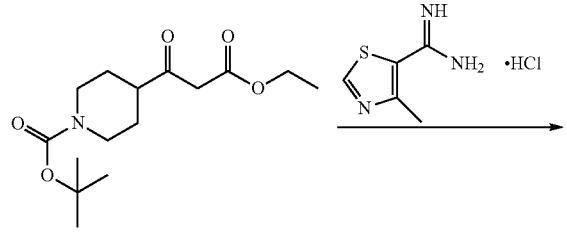

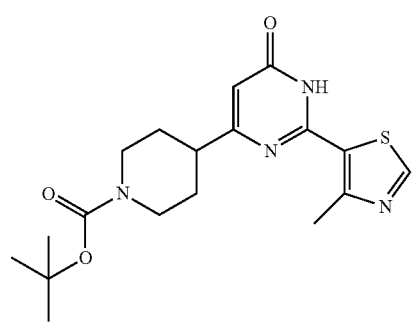

4-Methylthiazole-5-carboxamidine hydrochloride (1-001) (2.00 g, 14.2 mmol) was dissolved in MeOH (50 mL) and tert-butyl-4-(3-ethoxy-3-oxopropanoyl)tetrahydro-1(2H)-pyridinecarboxylate (4.24 g, 14.2 mmol) was added, followed by DBU (8.47 mL, 56.7 mmol). The reaction mixture was heated to reflux for 24 h. The reaction mixture was then concentrated under vacuum and the residue suspended in EtOAc (20 mL) then sonicated. The precipitate obtained was collected by vacuum filtration. The solid collected was partitioned between DCM and 1 N HCl solution (aq). The organic phase was separated, dried (MgSO$_4$), filtered and concentrated under vacuum to give the title compound (2.59 g, 49%). $^1$H NMR (300 MHz, CDCl$_3$) δ 11.93 (br s, 1H), 8.83 (s, 1H), 6.21 (s, 1H), 4.23 (br s, 2H), 2.89-2.72 (m, 5H), 2.68-2.55 (m, 1H), 1.90 (d, J=12.9 Hz, 2H), 1.65 (qd, J=12.4, 4.3 Hz, 2H), 1.47 (s, 9H).

Synthesis of tert-butyl 4-[5-chloro-2-(4-methylthiazol-5-yl)-6-oxo-1H-pyrimidin-4-yl]piperidine-1-carboxylate (1)

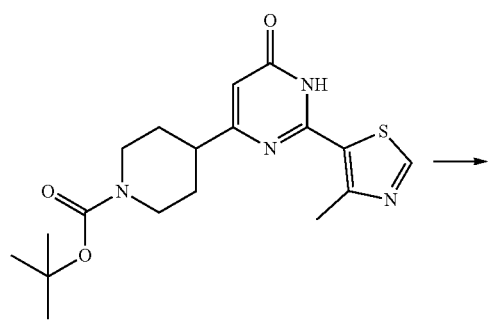

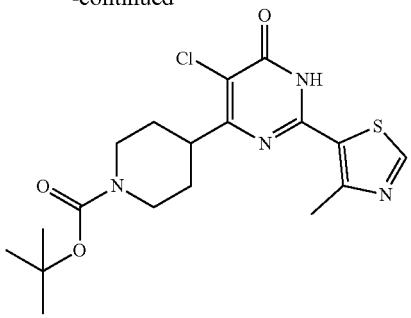

tert-Butyl 4-[5-chloro-2-(4-methylthiazol-5-yl)-6-oxo-1H-pyrimidin-4-yl]piperidine-1-carboxylate (1-002) (2.00 g, 5.31 mmol) in glacial acetic acid (50 mL) was treated with NCS (0.850 g, 6.37 mmol) and heated to reflux for 5 h. The reaction mixture was allowed to cool to room temperature then added to ice (50 mL). The resulting mixture was extracted with DCM. The aqueous phase was further extracted with DCM. The combined organic phases were dried (MgSO$_4$), filtered and concentrated under vacuum. The residue was dissolved in a minimum volume of DCM and was purified by column chromatography on silica gel, eluting with MeOH in DCM (0 to 5%). Fractions of interest were combined and concentrated under vacuum to give the title compound (0.194 g, 9%). LCMS: RT 3.58 min, MI 411, Method (1LCMS1); $^1$H NMR (300 MHz, CDCl$_3$) δ 12.11 (s, 1H), 8.86 (s, 1H), 4.25 (s, 2H), 3.38-3.15 (m, 1H), 3.00-2.58 (m, 5H), 1.98-1.61 (m, 4H), 1.48 (s, 9H).

Synthesis of 5-chloro-2-(4-methylthiazol-5-yl)-4-(4-piperidyl)-1H-pyrimidin-6-one (2)

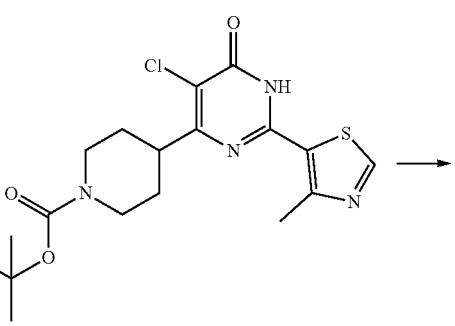

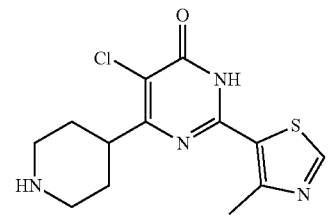

tert-Butyl 4-[5-chloro-2-(4-methylthiazol-5-yl)-6-oxo-1H-pyrimidin-4-yl]piperidine-1-carboxylate (1) (0.634 g, 1.544 mmol) was taken into DCM (20 mL) and HCl in dioxane (4 M, 0.385 mL) was added. The reaction mixture was stirred at room temperature for 18 h, followed by 45° C. for 18 h. The reaction mixture was allowed to cool to room temperature then concentrated under a flow of nitrogen. The residue was partitioned between DCM and saturated aqueous NaHCO₃ solution. The DCM phase was washed with brine, dried (MgSO₄), filtered and concentrated under vacuum to give the title compound (0.437 g, 91%). LCMS: RT 2.16 min, MI 311, Method (1LCMS1); ¹H NMR (300 MHz, DMSO-d₆) δ 9.13 (s, 1H), 3.36 (d, J=11.6 Hz, 3H), 3.05 (s, 2H), 2.72 (s, 3H), 1.94 (d, J=26.0 Hz, 4H).

Synthesis of 2-(4-methylthiazol-5-yl)-4-tetrahydropyran-4-yl-1H-pyrimidin-6-one (1-003)

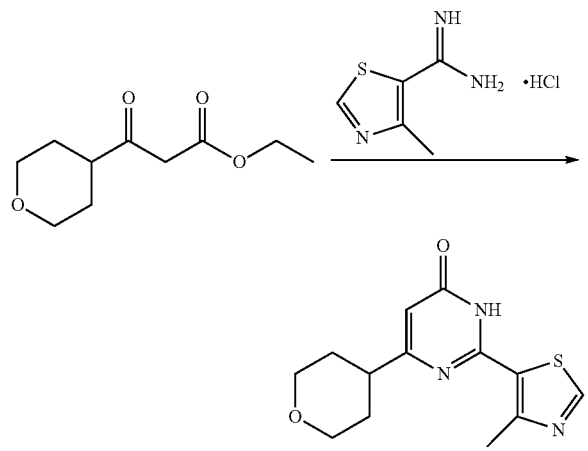

In a 50 mL round bottom flask equipped with a condenser, under nitrogen, was added 4-methylthiazole-5-carboxamidine; hydrochloride (1-001) (0.502 g, 2.82 mmol) in MeOH (10 mL). This was treated with 3-oxo-3-tetrahydropyran-4-yl propionic acid ethyl ester (0.568 g, 2.82 mmol) followed by DBU (1.69 mL, 11.3 mmol) and the reaction mixture stirred at 65° C. for 18 h. The reaction mixture was then concentrated under vacuum. The residue was dissolved in a minimum volume of DCM and purified by flash column chromatography on silica gel, eluting with MeOH in DCM (0 to 5%). The appropriate fractions were concentrated under vacuum and the residue was suspended in EtOAc and then sonicated for 5 min. The suspension was collected by vacuum filtration onto a sintered funnel to give the title compound (0.486 g, 62%). LCMS: RT 3.52 min, MI 278, Method (1LCMS1). ¹H NMR (300 MHz, DMSO-d₆) δ 12.11 (br s, 1H), 9.04 (s, 1H), 6.37 (s, 1H), 3.93 (d, J=10.7 Hz, 2H), 3.49-3.34 (m, 2H), 2.87-2.70 (m, 4H), 1.83-1.62 (m, 4H).

Synthesis of 5-bromo-2-(4-methylthiazol-5-yl)-4-tetrahydropyran-4-yl-1H-pyrimidin-6-one (3)

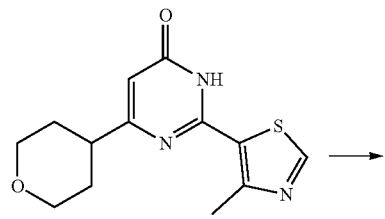

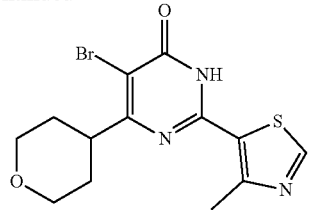

2-(4-Methylthiazol-5-yl)-4-tetrahydropyran-4-yl-1H-pyrimidin-6-one (1-003) (27.7 mg, 0.100 mmol) was suspended in DCM (1 mL). NBS (200 mg, 0.110 mmol) was added, followed by Et₃N (0.100 mL, 0.719 mmol) and the reaction allowed to stir overnight at room temperature. The mixture was concentrated under reduced pressure and the residue purified by preparative HPLC to give the title compound (23 mg, 65%). LCMS: RT 3.11 min, MI 357, Method (1LCMS1); ¹H NMR (300 MHz, CDCl₃) δ 8.88 (S, 1H), 4.10 (dd, J=11.4, 3.8 Hz, 2H), 3.57 (t, J=11.5 Hz, 2H), 3.37 (td, J=9.8, 8.0, 6.0 Hz, 1H), 2.87 (s, 3H), 2.03 (qd, J=12.5, 4.3 Hz, 2H), 1.71 (d, J=12.6 Hz, 2H).

Synthesis of 2-fluoro-3-oxo-3-(tetrahydro-pyran-4-yl)-propionic acid ethyl ester (1-004)

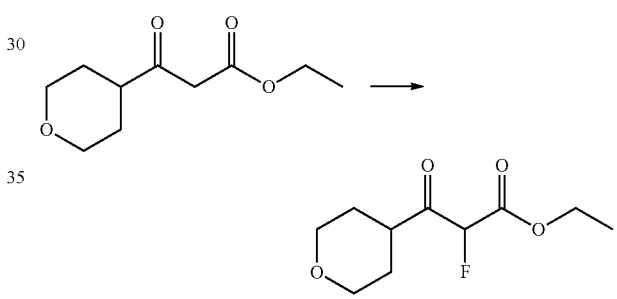

3-Oxo-3-tetrahydropyran-4-yl propionic acid ethyl ester (1.00 g, 5.00 mmol) and Selectfluor (1.95 g, 5.00 mmol) were combined in acetonitrile (10 mL). The reaction was allowed to stir at room temperature for 2 days. The solvent was evaporated under reduced pressure and DCM (20 mL) was added to the residue. A solid precipitated out which was removed by filtration. The filtrate was concentrated under reduced pressure and the resultant oil was purified by column chromatography (eluting with 0% DCM to 20% MeOH in DCM) to give the title compound (0.85 g, 78%). ¹H NMR (300 MHz, CDCl₃) δ 5.29 (d, J=49.3 Hz, 1H), 4.43-4.24 (m, 2H), 4.08-3.90 (m, 2H), 3.56-3.33 (m, 2H), 3.21-3.01 (m, 1H), 1.90-1.55 (m, 4H), 1.39-1.16 (m, 3H).

Synthesis of thiazole-5-carboxamidine (1-005)

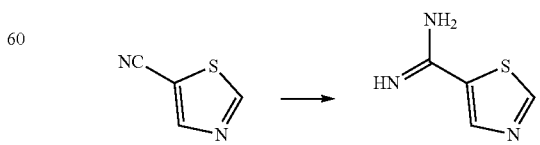

Thiazole-5-carbonitrile (0.69 g, 6.30 mmol) was dissolved in methanol (15 mL) and treated with sodium methoxide (0.033 g, 0.63 mmol) and then treated with ammonium chloride (0.33 g, 6.30 mmol). The reaction mixture was allowed to stir at room temperature for 3 days and then the solvent was evaporated under reduced pressure to a pale yellow solid. Methanol (2 mL) was added followed by diethyl ether (20 mL). The resulting white precipitate was filtered off and washed with diethyl ether (5 mL). The solid was dried under reduced pressure to yield the title compound (0.38 g, 47%) as a white solid. LCMS: RT 0.53 min, MI 128, Method (4LCMS1).

Synthesis of 2-methyl-2H-pyrazole-3-carboxamidine (1-006)

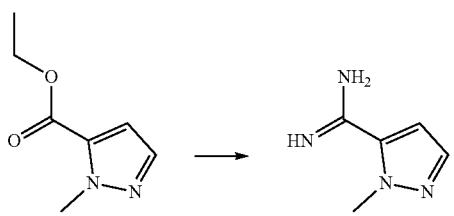

Ammonium chloride (1.87 g, 35.0 mmol) was suspended in dry toluene (50 mL) and azeotroped to dryness. The residue was placed under nitrogen and dissolved in toluene (30 mL). The suspension was cooled to 0° C. The reaction mixture was treated dropwise with trimethylaluminium (2 M in toluene, 17.5 mL, 35.0 mmol), keeping the temperature below 10° C. The reaction mixture was left to warm to room temperature and allowed to stir for three hours. 2-Methyl-2H-pyrazole-3-carboxylic acid ethyl ester (1.07 g, 7.00 mmol) was added to the reaction mixture and then heated at 80° C. for 15 hours. The reaction mixture was quenched by the careful addition of methanol (40 mL) at 0° C. The reaction mixture was left to stir at room temperature for 30 min and the thick white cloudy suspension was filtered through celite to remove the excess aluminium residues. The filtrates were evaporated under reduced pressure to give a white solid which was taken up in a minimum amount of methanol (10 mL). Diethyl ether was added (50 mL) to precipitate the excess aluminium residues which were then filtered off. The filtrates were concentrated under reduced pressure to provide the title compound (0.58 g, 67%) as a yellow solid. LCMS: RT 0.56 min, MI 125, Method (5LCMS1); $^1$H NMR (400 MHz, DMSO-d$_6$) δ 9.41 (d, 3H), 7.65 (d, 1H), 6.86 (d, 1H), 3.99 (s, 3H).

Synthesis of 4-methyl-oxazole-5-carboxamidine (1-007)

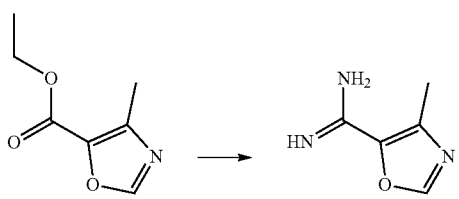

Ammonium chloride was suspended in toluene and azeotroped on a rotary evaporator. The ammonium chloride (1.59 g, 30.0 mmol) was weighed into a 3-neck round bottom flask under a nitrogen atmosphere. Toluene (15 mL) was added and the suspension was cooled to 0° C. The reaction mixture was treated dropwise with trimethylaluminium 2 M in toluene (15 mL, 30.0 mmol). The reaction mixture was left to warm to room temperature and stirred for 3 hours. 4-Methyl-oxazole-5-carboxylic acid ethyl ester (0.465 g, 3.00 mmol) was added and the reaction mixture was heated at 80° C. overnight. The reaction was cooled and quenched by slow addition of methanol (30 mL). A white solid precipitated which was then filtered off through celite, washing with more methanol. The methanol was then evaporated until approximately 5 mL was left. This was then treated with diethyl ether (20 mL) and filtered again. The filtrate was then evaporated to yield the title compound (0.34 g, 89%). $^1$H NMR (400 MHz, DMSO-d$_6$) δ 9.52 (s, 2H), 9.35 (s, 2H), 8.78 (s, 1H), 2.41 (s, 3H).

Synthesis of 4-ethyl-thiazole-5-carboxamidine (1-008)

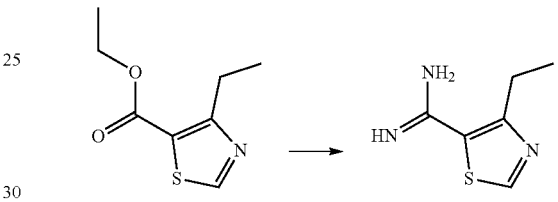

Ammonium chloride was suspended in toluene and azeotroped on a rotary evaporator. The ammonium chloride (0.53 g, 10.0 mmol) was weighed into a 3-neck round bottom flask under a nitrogen atmosphere. Toluene (5 mL) was added and the suspension was cooled to 0° C. The reaction mixture was treated dropwise with trimethylaluminium 2 M in hexane (5 mL, 10.0 mmol). The reaction mixture was left to warm to room temperature and stirred for 3 hours. Then 4-ethyl-thiazole-5-carboxylic acid ethyl ester (0.185 g, 1.00 mmol) was added and the reaction mixture was heated at 80° C. overnight. The reaction was cooled and quenched by slow addition of methanol (30 mL). A white solid precipitated which was then filtered off through celite, washing with more methanol. The methanol was then evaporated until approximately 1 mL was left. This was then treated with diethyl ether (5 mL) and filtered again. The residual solvent was then evaporated to give the title compound (0.13 g, 81%) LCMS: RT solvent front, Method (4LCMS1).

Synthesis of 4-trifluoromethyl-thiazole-5-carboxamidine (1-009)

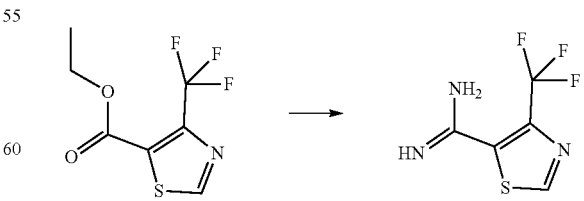

Ammonium chloride was suspended in toluene and azeotroped on a rotary evaporator. The ammonium chloride (6.42 g, 120.0 mmol) was weighed into a 3-neck round bottom flask under a nitrogen atmosphere. Toluene (60 mL) was added and the suspension was cooled to 0° C. The reaction mixture was treated dropwise with trimethylaluminium 2 M in toluene (60 mL, 120.0 mmol). The reaction mixture was left to warm to room temperature and stirred for 3 hours. Then 4-trifluoromethyl-thiazole-5-carboxylic acid ethyl ester (2.70 g, 12.0 mmol) was added and the reaction mixture was heated at 80° C. overnight. The reaction was cooled and quenched by slow addition of methanol (30 mL). A white solid precipitated which was then filtered off through celite, washing with more methanol. The methanol was then evaporated until approximately 10 mL was left. This was then treated with diethyl ether (50 mL) and filtered again. The residual solvent was evaporated to give the title compound (2.0 g, 85%). LCMS: RT solvent front, Method (4LCMS1).

Synthesis of 4-chloro-thiazole-5-carboxylic acid methyl ester (1-010)

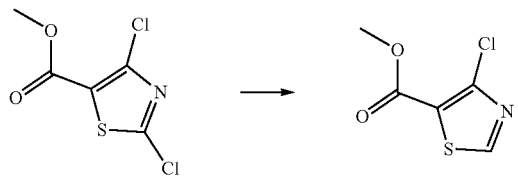

A solution of methyl 2,4-dichlorothiazole-5-carboxylate (1.06 g, 5.00 mmol) in AcOH (15 mL) was heated to reflux and zinc dust (1.00 g, 15.0 mmol) was added. The mixture was stirred at reflux for 2 h. The mixture was allowed to cool to room temperature before the addition of 2 M aqueous NaOH solution (90 mL), water (50 mL) and a saturated aqueous solution of NaHCO$_3$ (60 mL) (a pH of approximately 7 was achieved). The mixture was extracted with DCM (2×200 mL) and the combined organics dried and concentrated under reduced pressure. The residue was purified by flash chromatography on silica gel (eluting with 0-10% EtOAc in cyclohexane) to afford the title compound (0.507 mg, 57%) as a white solid. LCMS: RT 3.40 min, MI 178, Method (4LCMS1).

Synthesis of 4-chloro-thiazole-5-carboxamidine (1-011)

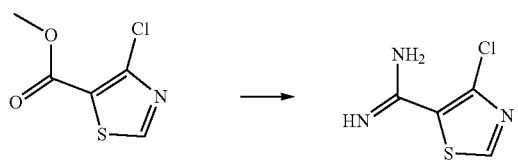

Ammonium chloride was suspended in toluene and azeotroped. Ammonium chloride (1.65 g, 30.9 mmol) was placed under nitrogen and dissolved in toluene (15 mL). The suspension was cooled to 0° C. The reaction mixture was treated dropwise with trimethylaluminium 2 M in toluene (16 mL, 30.9 mmol), carefully monitoring the temperature to −5 to 0° C. The reaction mixture was left to warm to room temperature and allowed to stir for 2.5 hours. 4-Chloro-thiazole-5-carboxylic acid methyl ester (1-010) (0.549 g, 3.09 mmol) in toluene (10 mL) was added and the mixture heated to 80° C. overnight under nitrogen. The mixture was cooled to 0° C. and quenched with the slow addition of MeOH (30 mL). The resultant white precipitate was filtered through celite and washed with MeOH (70 mL). The filtrate was evaporated under reduced pressure. The residue was triturated in methanol (10 mL) and the supernatant liquid collected by pipette. This was repeated 3 times. The combined supernatant liquids were concentrated under reduced pressure. A mixture of MeOH:Et$_2$O (1:2 ratio, 50 mL) was then added, the mixture filtered and the filtrate concentrated under reduced pressure to give the title compound (0.386 g, 77%) as a yellow solid. LCMS: RT 0.6 min, MI 162, Method (4LCMS1).

Synthesis of 2-(4-chlorothiazol-5-yl)-4-tetrahydropyran-4-yl-1H-pyrimidin-6-one (1-012)

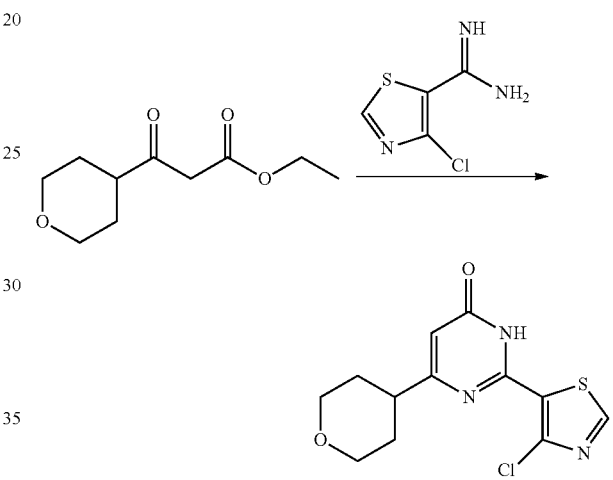

4-Chloro-thiazole-5-carboxamidine (1-011) (0.385 g, 2.380 mmol) was dissolved in MeOH (25 mL) and 3-oxo-3-(tetrahydro-pyran-4-yl)-propionic acid ethyl ester (0.524 g, 2.620 mmol) then DBU (0.71 mL, 4.760 mmol) added. The mixture was heated to reflux for 2 h. The reaction was concentrated under reduced pressure and the residue purified by flash chromatography on silica gel (eluting with 30% EtOAc/cyclohexane, then 10% MeOH/DCM) to give the title compound (0.177 g, 25%) as an orange solid. LCMS: RT 2.88 min, MI 298, Method (4LCMS1).

Synthesis of 5-chloro-2-(4-chlorothiazol-5-yl)-4-tetrahydropyran-4-yl-1H-pyrimidin-6-one (4)

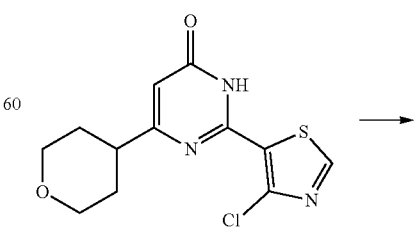

-continued

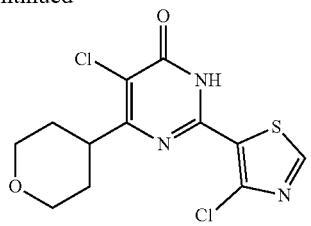

To a solution of 2-(4-chlorothiazol-5-yl)-4-tetrahydropyran-4-yl-1H-pyrimidin-6-one (1-012) (0.176 g, 0.590 mmol) in MeCN (6 mL) was added N-chlorosuccinamide (0.083 g, 0.620 mmol) and triethylamine (0.164 mL, 1.180 mmol) and the mixture allowed to stir at room temperature under nitrogen for 4 h. Further NCS (30 mg) was added and the mixture allowed to stir at room temperature overnight. The reaction was concentrated under reduced pressure, the residue dissolved in DCM (50 mL) and washed with a saturated solution of disodium citrate (50 mL). The aqueous layer was extracted with further DCM (50 mL). The combined organics were dried and concentrated under reduced pressure to afford an orange solid. This was purified by preparative HPLC to give the title compound (0.120 g, 60%). LCMS: RT 3.52 min, MI 332, Method (4LCMS1); $^1$H NMR (400 MHz, DMSO-$d_6$) δ 9.25 (s, 1H), 3.96 (ddd, J=11.4, 4.5, 1.7 Hz, 2H), 3.46 (td, J=11.9, 2.0 Hz, 2H), 1.86 (ddt, J=16.7, 12.0, 6.0 Hz, 2H), 1.76-1.47 (m, 3H).

Synthesis of 2-chloro-4-methyl-thiazole-5-carboxamidine (1-013)

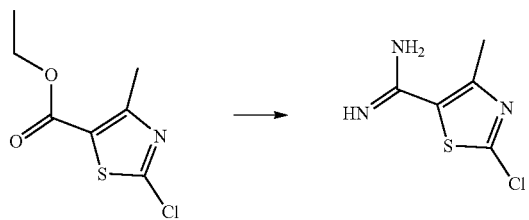

Ammonium chloride was suspended in toluene and azeotroped on a rotary evaporator. The ammonium chloride (4.81 g, 90.0 mmol) was weighed into a 3-neck round bottom flask under a nitrogen atmosphere. Toluene (45 mL) was added and the suspension was cooled to 0° C. The reaction mixture was treated dropwise with trimethylaluminium 2 M in hexane (45 mL, 90.0 mmol). The reaction mixture was left to warm to room temperature and stirred for 3 hours. Then 2-chloro-4-methyl-thiazole-5-carboxylic acid methyl ester (1.85 g, 9.00 mmol) was added and the reaction mixture was heated at 80° C. overnight. The reaction was cooled and quenched by slow addition of methanol (30 mL). A white solid precipitated which was then filtered off through celite, washing with more methanol. The methanol was then evaporated until approximately 1 mL was left. This was then treated with diethyl ether (5 mL) and filtered again. The solvent was then evaporated to give the title compound (1.4 g, 89%). LCMS: MI 176, Method (4LCMS1).

Synthesis of 2-(2-chloro-4-methyl-thiazol-5-yl)-4-tetrahydropyran-4-yl-1H-pyrimidin-6-one (1-014)

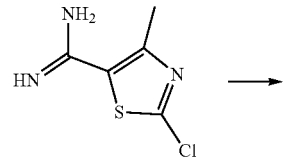

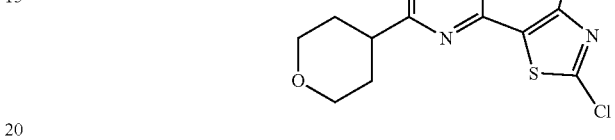

2-Chloro-4-methyl-thiazole-5-carboxamidine (1-013) (0.79 g, 4.50 mmol) was dissolved in IPA (50 mL) and treated with 3-oxo-3-(tetrahydro-pyran-4-yl)-propionic acid ethyl ester (0.837 g, 4.50 mmol) and DBU (1.77 mL, 13.5 mmol), this was stirred at room temperature under nitrogen overnight. The reaction mixture was then evaporated and the resulting oil re-dissolved in DCM and washed with saturated sodium citrate to yield the title compound (1.05 g, 75%) as an orange solid. LCMS: RT 3.74 min, MI 312, Method (4LCMS1).

Synthesis of 5-chloro-2-(2-chloro-4-methyl-thiazol-5-yl)-4-tetrahydropyran-4-yl-1H-pyrimidin-6-one (1-015)

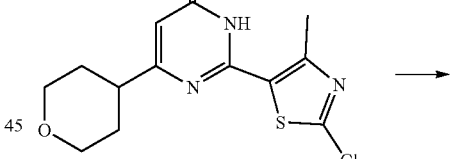

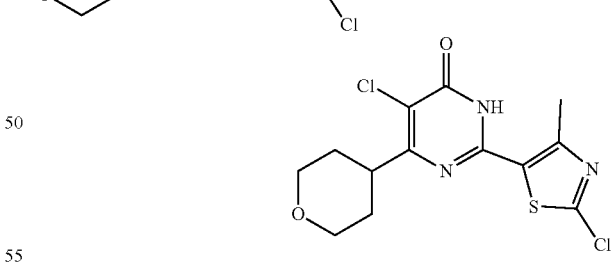

2-(2-chloro-4-methyl-thiazol-5-yl)-4-tetrahydropyran-4-yl-1H-pyrimidin-6-one (1-014) (0.624 g, 2.00 mmol) was dissolved in DCM (10 mL) and treated with NCS (0.60 g, 4.50 mmol) followed by triethylamine (0.60 mL, 4.50 mmol) and left to stir for 30 minutes. The reaction mixture was then washed with saturated sodium citrate and then evaporated. This was then purified by flash chromatography on silica gel (eluting with 0-100% ethyl acetate in hexane), and then fractions containing the product were evaporated to give the title compound (0.60 g, 87%). LCMS: RT 4.29 min, MI 346, Method (4LCMS1).

Synthesis of 5-chloro-2-(2-hydroxy-4-methyl-thiazol-5-yl)-4-tetrahydropyran-4-yl-1H-pyrimidin-6-one (5)

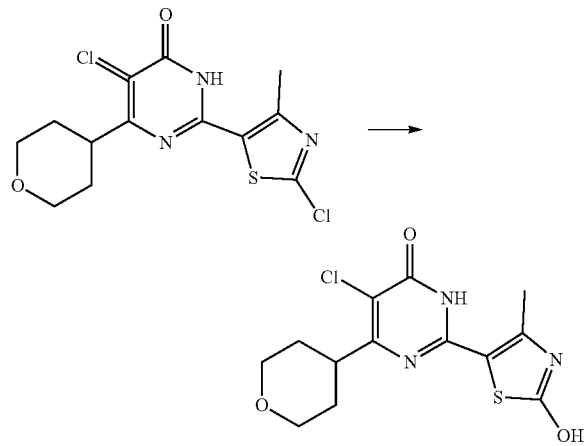

5-chloro-2-(2-chloro-4-methyl-thiazol-5-yl)-4-tetrahydropyran-4-yl-1H-pyrimidin-6-one (1-015) (0.172 g, 0.500 mmol) was dissolved in THF (5 mL) and treated with aqueous sodium hydroxide (5 mL) and heated in the microwave to 100° C. for 1 hour. This was then acidified to pH 5 and extracted with DCM. The product remained in the aqueous layer which was then evaporated under reduced pressure and the residue re-dissolved in DMSO then filtered. This was then purified by preparative HPLC. The fractions containing the product were then combined and evaporated to give the title compound (0.03 g, 19%) LCMS: RT 3.08 min, MI 328, Method (4LCMS1); $^1$H NMR (400 MHz, DMSO-$d_6$) δ 12.88 (s, 1H), 11.70 (s, 1H), 3.97 (dd, J=11.3, 3.4 Hz, 2H), 3.47 (t, J=11.0 Hz, 2H), 3.35 (s, 3H), 3.30 (dt, J=7.9, 3.8 Hz, 1H), 1.81 (qd, J=12.7, 12.2, 4.4 Hz, 2H), 1.64 (d, J=11.2 Hz, 2H).

The following compounds were synthesised according to the general synthesis shown in scheme [1]:

| No | General formula of Starting Material | Product [F1-5] | Characterisation |
|---|---|---|---|
| 6 | F1-1 | | RT 4.42 min, MI 312/314, Method (1LCMS1); $^1$H NMR (300 MHz, DMSO-$d_6$) δ 13.17 (br s, 1H), 9.11 (s, 1H), 3.99-3.89 (m, 2H), 3.45 (td, J = 11.9, 2.1 Hz, 2H), 3.39-3.25 (m, 1H), 2.73 (s, 3H), 1.82 (qd, J = 12.4, 4.4 Hz, 2H), 1.69-1.57 (m, 2H). |
| 7 | F1-1 | | RT 3.27 min, MI 404, Method (1LCMS1); $^1$H NMR (300 MHz, CDCl$_3$) δ 8.87 (s, 1H), 4.10 (dd, J = 11.2, 4.0 Hz, 2H), 3.57 (t, J = 11.2 Hz, 2H), 3.50-3.34 (m, 1H), 2.86 (s, 3H), 2.04 (qd, J = 12.7, 4.8 Hz, 2H), 1.70 (d, J = 13.2 Hz, 2H). |
| 8 | F1-4 | | RT 2.97 min, MI 296, Method (1LCMS1); $^1$H NMR (300 MHz, CDCl$_3$) δ 8.87 (s, 1H), 4.20-3.95 (m, 2H), 3.57 (t, J = 11.9 Hz, 2H), 3.38-3.12 (m, 1H), 2.84 (s, 3H), 2.17-1.90 (m, 2H), 1.67 (d, J = 13.6 Hz, 2H). |
| 9 | F1-1 | | RT 3.14 min, MI 297/299, Method (4LCMS1); $^1$H NMR (400 MHz, DMSO-$d_6$) δ 13.57 (s, 1H), 9.32 (s, 1H), 8.81 (s, 1H), 3.96 (d, J = 8.3 Hz, 2H), 3.46 (t, J = 11.0 Hz, 2H), 3.30-3.22 (m, 1H), 1.83 (d, J = 8.5 Hz, 2H), 1.60 (d, J = 11.5 Hz, 2H). |

-continued

| No | General formula of Starting Material | Product [F1-5] | Characterisation |
|---|---|---|---|
| 10 | F1-1 | (structure: 5-chloro-2-(1-methyl-1H-pyrazol-5-yl)-6-(tetrahydro-2H-pyran-4-yl)pyrimidin-4(3H)-one) | RT 3.09 min, MI 294/296, Method (5LCMS1); $^1$H NMR (400 MHz, DMSO-d$_6$) δ 13.21(br s, 1H), 7.57 (d, 1H), 7.19 (d, 1H), 4.20 (s, 3H), 4.04-3.90 (m, 2H), 3.47 (td, 2H), 3.32-3.26 (m, 1H, partially obscured by water), 1.97-1.77 (m, 2H), 1.72-1.58 (m, 2H). |
| 11 | F1-1 | (structure: 5-chloro-2-(4-methyl-1,2,3-thiadiazol-5-yl)-6-(tetrahydro-2H-pyran-4-yl)pyrimidin-4(3H)-one) | RT 3.69 min, MI 313, Method (4LCMS1); $^1$H NMR (400 MHz, DMSO-d$_6$) δ 13.67 (s, 1H), 3.98 (ddd, J = 11.4, 4.5, 1.7 Hz, 2H), 3.49 (td, J = 11.9, 2.1 Hz, 2H), 3.44-3.36 (m, 1H), 3.01 (s, 3H), 1.94-1.75 (m, 2H), 1.69 (ddd, J = 12.7, 4.0, 1.9 Hz, 2H). |
| 12 | F1-1 | (structure: 5-chloro-2-(4-methyloxazol-5-yl)-6-(tetrahydro-2H-pyran-4-yl)pyrimidin-4(3H)-one) | RT 3.04 min, MI 296, Method (4LCMS1); $^1$H NMR (400 MHz, DMSO-d$_6$) δ 13.30 (s, 1H), 8.59 (s, 1H), 3.96 (dd, J = 11.5, 4.1 Hz, 2H), 3.51-3.42 (m, 2H), 3.33-3.25 (m, 1H), 2.55 (s, 3H), 1.84 (qd, J = 12.5, 4.5 Hz, 2H), 1.64 (d, J = 11.5 Hz, 2H). |
| 13 | F1-1 | (structure: 5-chloro-2-(4-ethylthiazol-5-yl)-6-(tetrahydro-2H-pyran-4-yl)pyrimidin-4(3H)-one) | RT 3.44 min, MI 326, Method (4LCMS1); $^1$H NMR (400 MHz, CDCl$_3$) δ 8.88 (s, 1H), 4.11 (dd, J = 11.2, 3.6 Hz, 2H), 3.58 (td, J = 12.3, 1.9 Hz, 2H), 3.41 (tt, J = 11.7, 3.7 Hz, 1H), 3.23 (q, J = 7.5 Hz, 2H), 2.04 (qd, J = 12.4, 4.4 Hz, 2H), 1.76-1.64 (m, 2H), 1.40 (t, J = 7.5 Hz, 3H). |
| 14 | F1-1 | (structure: 5-chloro-2-(4-(trifluoromethyl)thiazol-5-yl)-6-(tetrahydro-2H-pyran-4-yl)pyrimidin-4(3H)-one) | RT 3.81 min, MI 365, Method (4LCMS1). $^1$H NMR (400 MHz, DMSO-d$_6$) δ 13.67 (s, 1H), 9.35 (s, 1H), 3.94 (dd, J = 11.3, 3.4 Hz, 2H), 3.45 (td, J = 12.2, 1.7 Hz, 2H), 3.41-3.26 (m, 1H), 1.81 (qd, J = 12.6, 4.4 Hz, 2H), 1.66-1.51 (m, 2H). |

Synthesis of 5-ethyl-1-(tetrahydro-pyran-2-yl)-1H-pyrazole-4-carboxylic acid methyl ester (1-016)

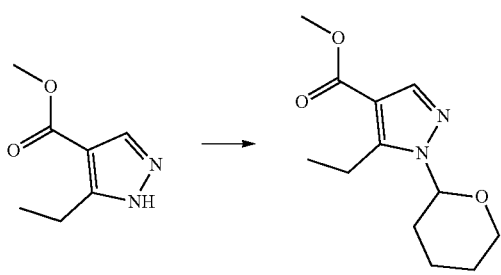 [SMILES: CCc1[nH]ncc1C(=O)OC ; CCc1c(C(=O)OC)cnn1C1CCCCO1]

5-Ethyl-1H-pyrazole-4-carbonitrile (0.150 g, 1.00 mmol) was weighed into a round bottom flask and dissolved in THF (5 mL). To the solution was added 3,4-dihydro-2H-pyran (0.120 g, 1.50 mmol), molecular sieves and p-toluenesulfonic acid monohydrate (90.02 g, 0.100 mmol). The reaction mixture was heated at reflux for 1 hour and then cooled to room temperature. The solvent was removed under reduced pressure and DCM (20 mL) was added and water (20 mL). The organics were collected, dried with MgSO$_4$, filtered and evaporated to yield the title compound (90.21 g, 87%) as a white solid. LCMS: RT 4.13 min, MI 239, Method (4LCMS1); $^1$H NMR (400 MHz, CDCl$_3$) δ 8.04 (s, 1H), 5.36-5.19 (m, 1H), 4.08 (d, J=10.4 Hz, 1H), 3.81 (s, 3H), 3.76-3.60 (m, 1H), 2.90 (q, J=7.5 Hz, 2H), 2.15-1.95 (m, 3H), 1.85-1.45 (m, 3H), 1.25 (t, 3H).

Synthesis of 5-ethyl-1-(tetrahydro-pyran-2-yl)-1H-pyrazole-4-carboxamidine (1-017)

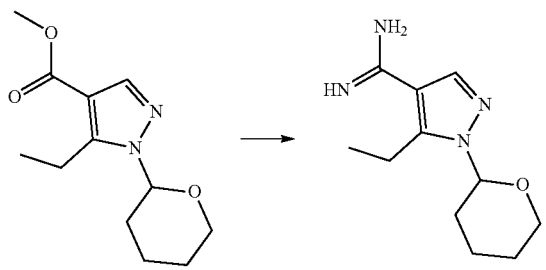 [SMILES: CCc1c(C(=O)OC)cnn1C1CCCCO1 ; CCc1c(C(=N)N)cnn1C1CCCCO1]

Ammonium chloride (0.48 g, 9.00 mmol) was suspended in toluene and azeotroped on a rotary evaporator and then transferred into a 3 neck round bottom flask and placed under a nitrogen atmosphere. Toluene (5 mL) was added and the suspension was cooled to 0° C. The reaction mixture was treated dropwise with trimethylaluminium 2 M in toluene (4.5 mL, 9.00 mmol). The reaction mixture was left to warm to room temperature and stirred for 3 hours. Then 5-ethyl-1-(tetrahydro-pyran-2-yl)-1H-pyrazole-4-carboxylic acid methyl ester (1-016) (0.21 g, 0.90 mmol) was added in toluene (2 mL) and the reaction mixture was heated at 80° C. for 15 hours. The reaction mixture was cooled to 0° C. and treated cautiously with methanol (5 mL). The reaction mixture was left to stir for 30 minutes and then filtered through celite washing with methanol. The filtrates were evaporated under reduced pressure to yield a white solid. This was taken up in the minimum amount of methanol and treated with diethyl ether (10 mL) to precipitate a white solid which was filtered off and discarded. The process was repeated again on the filtrates and evaporation under reduced pressure yielded the title compound (0.11 g, 55%) as a pale yellow gum. LCMS: RT 1.60 min, MI 223, Method (4LCMS1).

Synthesis of 2-(5-ethyl-1-tetrahydropyran-2-yl-pyrazol-4-yl)-4-tetrahydropyran-4-yl-1H-pyrimidin-6-one (1-018)

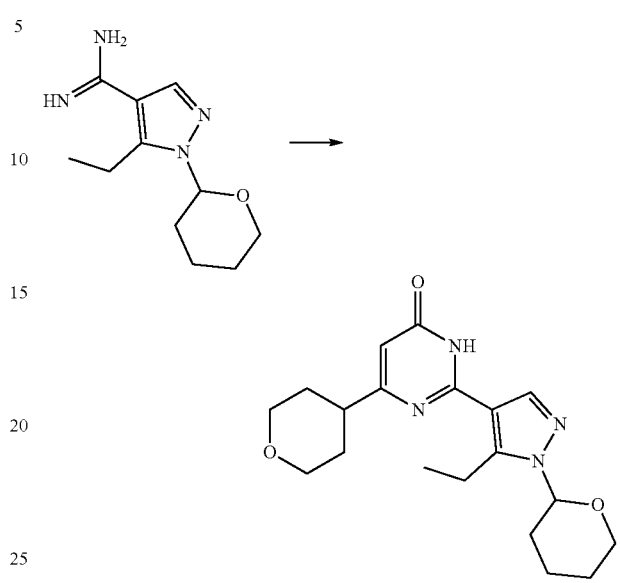

5-Ethyl-1-(tetrahydro-pyran-2-yl)-1H-pyrazole-4-carboxamidine (1-017) (0.11 g, 0.50 mmol) was dissolved in methanol (5 mL) and treated with 3-oxo-3-(tetrahydro-pyran-4-yl)-propionic acid ethyl ester (0.069 g, 0.50 mmol) and DBU (0.15 mL, 1.00 mmol). The reaction mixture was heated at reflux for 4 hours and then allowed to cool to room temperature and concentrated under reduced pressure. The residue was purified by flash column chromatography (eluting with 95:5 DCM:MeOH) to yield the title compound (0.14 g, 77%) as a white solid. LCMS: RT 3.38 min, MI 359/360, Method (4LCMS1).

Synthesis of 5-chloro-2-(5-ethyl-1-tetrahydropyran-2-yl-pyrazol-4-yl)-4-tetrahydropyran-4-yl-1H-pyrimidin-6-one (1-019)

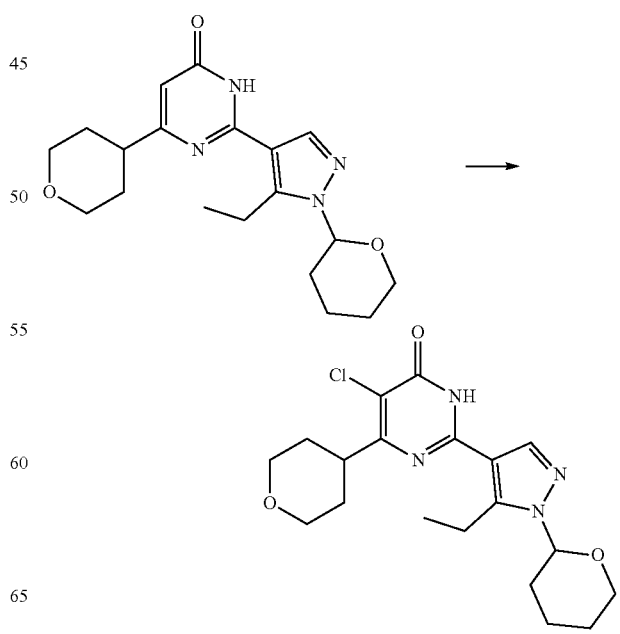

2-(5-ethyl-1-tetrahydropyran-2-yl-pyrazol-4-yl)-4-tetrahydropyran-4-yl-1H-pyrimidin-6-one (1-018) (0.14 g, 0.40 mmol) was dissolved in dichloromethane (2 mL) and triethylamine (0.14 mL, 1.00 mmol) and treated with N-chlorosuccinamide (0.13 g, 1.00 mmol). The reaction mixture was allowed to stir at room temperature for 15 hours. Saturated aqueous NH₄Cl solution was added (10 mL) and the organics were separated. The organics were dried with MgSO₄, filtered and evaporated to yield an orange solid. This was purified by flash column chromatography (eluting with DCM then 95:5 DCM:MeOH) to give the title compound (0.15 g, 93%) as a pale yellow solid. LCMS: RT 4.02 min, MI 393/395, Method (4LCMS1).

Synthesis of 5-chloro-2-(5-ethyl-1H-pyrazol-4-yl)-4-tetrahydropyran-4-yl-1H-pyrimidin-6-one (15)

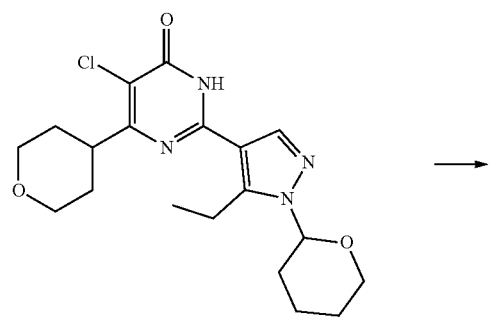

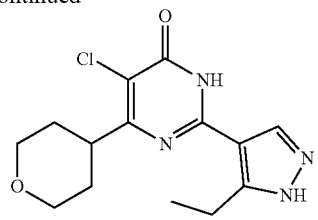

5-chloro-2-(5-ethyl-1-tetrahydropyran-2-yl-pyrazol-4-yl)-4-tetrahydropyran-4-yl-1H-pyrimidin-6-one (1-019) (0.15 g, 0.40 mmol) was suspended in methanol (15 mL) and treated with p-TSA (0.010 g, 0.004 mmol). The reaction mixture was allowed to stir at room temperature for 2 days. Further methanol (10 mL) was added to dissolve the solid and further p-TSA (5 mg, 0.002 mmol) added. The resultant solution was left to stir for 3 days at room temperature. The solvent was removed under reduced pressure and the residue was dissolved in DCM (20 mL) and washed with aqueous NH₄Cl solution (20 mL). The organics were passed through a phase separation cartridge and evaporated under reduced pressure. The residue was purified by mass directed LCMS. The fractions were evaporated to yield the title compound (0.016 g, 13%) as an off white solid. LCMS: RT 3.11 min, MI 309/311, Method (4LCMS1); ¹H NMR (400 MHz, DMSO-d₆) δ 12.77 (s, 1H), 8.36 (s, 1H), 3.95 (dd, J=11.2, 3.7 Hz, 2H), 3.55-3.39 (m, 2H), 3.29 (dd, J=25.7, 14.0 Hz, 1H), 3.03 (q, J=7.4 Hz, 2H), 1.84 (dt, J=12.3, 8.3 Hz, 2H), 1.61 (d, J=10.9 Hz, 2H), 1.22 (t, J=7.5 Hz, 3H).

The following compounds were synthesised using a similar procedure to that of compound (15) above, using an appropriately substituted THP-protected pyrazole:

| No | Product [F1-5] | Characterisation |
|---|---|---|
| 16 | (structure) | RT 2.92 min, MI 295 Method (4LCMS1) |
| 17 | (structure) | RT 3.48 min, MI 348, Method (4LCMS1); ¹H NMR (400 MHz, DMSO-d₆) δ 14.07 (s, 1H), 13.11 (s, 1H), 8.70 (s, 1H), 4.03-3.81 (m, 2H), 3.49-3.38 (m, 2H), 3.26 (ddt, J = 11.6, 7.3, 3.6 Hz, 1H), 1.86 (qd, J = 12.6, 4.4 Hz, 2H), 1.59-1.46 (m, 2H). |

Synthesis of 2-(4-methylthiazol-5-yl)-6-oxo-4-tetrahydropyran-4-yl-1H-pyrimidine-5-carbonitrile (18)

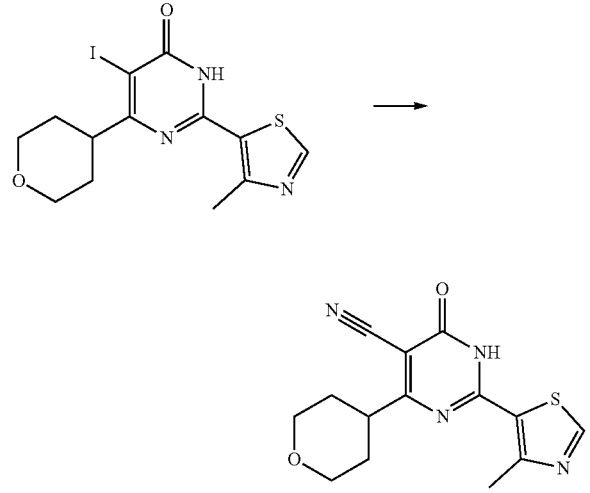

5-Iodo-2-(4-methylthiazol-5-yl)-4-tetrahydropyran-4-yl-1H-pyrimidin-6-one (7) (0.081 g, 0.200 mmol), $Zn(CN)_2$ (0.047 g, 0.400 mmol), $Pd(PPh_3)_4$ (0.070 g, 0.060 mmol) and CuI (0.020 g, 0.100 mmol) were combined in dry DMF (1 mL). The mixture was flushed with nitrogen, sealed and heated in the microwave for 30 min at 130° C. The suspension was diluted with MeOH and the resulting suspension was filtered through celite. The filtrate was concentrated under vacuum. The residue was purified by reverse phase mass directed HPLC to give the title compound (2 mg, 3%). LCMS: RT 4.50 min, MI 303, Method (1LCMS1).

Synthesis of 5-chloro-4-[1-(2,2-difluorocyclopropanecarbonyl)-4-piperidyl]-2-(4-methylthiazol-5-yl)-1H-pyrimidin-6-one (19)

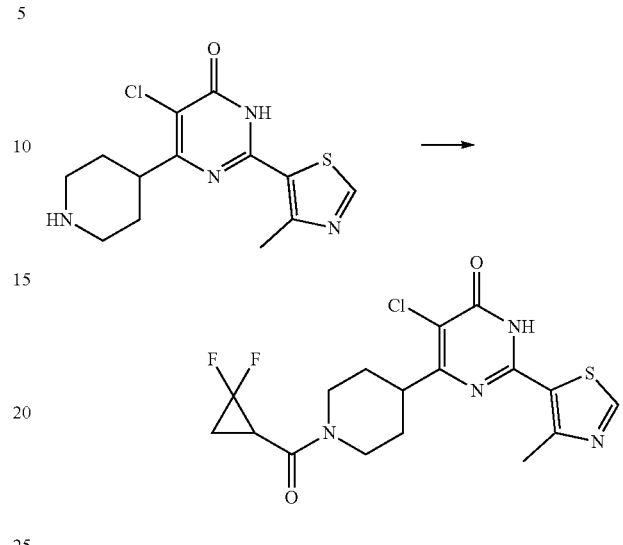

To a solution of 2,2-difluorocyclopropanecarboxylic acid (13.4 mg, 0.110 mmol) in dry DMF (1 mL) was added DIPEA (87 μL, 0.250 mmol) followed by HBTU (57 mg, 0.150 mmol). The reaction mixture was placed under nitrogen, sealed then shaken for 15 minutes. A suspension of 5-chloro-2-(4-methylthiazol-5-yl)-4-(4-piperidyl)-1H-pyrimidin-6-one (2) (35 mg, 0.100 mmol) in DMF (1 mL) and DIPEA (87 μL, 0.250 mmol) was added to the reaction mixture and the mixture was shaken for 1 h. After this time, the mixture was purified by preparative HPLC to afford the title compound. LCMS: RT 4.47 min, MI 415.1/417.1, Method (1LCMS1); $^1$H NMR (500 MHz, DMSO-$d_6$) δ 13.17 (s, 1H), 9.09 (s, 1H), 4.47 (d, J=13.1 Hz, 1H), 4.25-4.08 (m, 1H), 3.47-3.09 (m, 3H), 2.87-2.74 (m, 1H), 2.73-2.64 (m, 3H), 2.00-1.45 (m, 6H).

The following compounds were synthesised using a similar procedure to that of compound (19) above:

| No | Product | Characterisation |
|---|---|---|
| 20 | | RT 4.12 min, MI 436, Method (1LCMS1); $^1$H NMR (500 MHz, DMSO-$d_6$) δ 13.19 (s, 1H), 9.11 (s, 1H), 9.09 (s, 1H), 3.47-2.90 (m, 5H), 2.71 (s, 3H), 2.38 (s, 3H), 1.90-1.62 (m, 4H). |
| 21 | | RT 4.05 min, MI 422, Method (1LCMS1); $^1$H NMR (500 MHz, DMSO-$d_6$) δ 13.17 (s, 1H), 9.16 (d, J = 2.0 Hz, 1H), 9.10 (s, 1H), 8.14 (d, J = 2.0 Hz, 1H), 4.60 (s, 1H), 4.24 (d, 1H), 3.40 (d, 1H), 3.28-3.17 (m, 1H), 3.00-2.88 (m, 1H), 2.69 (s, 3H), 1.96-1.66 (m, 4H). |

| No | Product | Characterisation |
|---|---|---|
| 22 | | RT 4.12 min, MI 419, Method (1LCMS1); $^1$H NMR (300 MHz, DMSO-d$_6$) δ 13.15 (br s, 1H), 12.82 (br s, 1H), 9.09 (s, 1H), 6.27 (s, 1H), 4.81 (br s, 1H), 4.60 (d, J = 12.7 Hz, 1H), 3.49-3.07 (m, 2H), 2.96-2.78 (m, 1H), 2.68 (s, 3H), 2.23 (s, 3H), 1.90-1.57 (m, 4H). |
| 23 | | RT 4.28 min, MI 433, Method (1LCMS1); $^1$H NMR (500 MHz, DMSO-d$_6$) δ 13.17 (s, 1H), 9.10 (s, 1H), 6.32 (s, 1H), 4.81 (d, J = 13.3 Hz, 1H), 4.60 (d, J = 12.9 Hz, 1H), 3.75 (s, 3H), 3.46-3.33 (m, 1H), 3.21 (t, J = 12.6 Hz, 1H), 2.85 (t, J = 12.9 Hz, 1H), 2.69 (s, 3H), 2.26 (s, 3H), 1.89-1.61 (m, 4H). |
| 24 | | RT 4.38 min, MI 433, Method (1LCMS1); $^1$H NMR (300 MHz, DMSO-d$_6$) δ 13.19 (s, 1H), 9.11 (s, 1H), 6.20 (s, 1H), 4.57 (d, 1H), 3.95 (d, J = 13.1 Hz, 1H), 3.74 (s, 3H), 3.49-3.18 (m, 2H), 3.05-2.86 (m, 1H), 2.70 (s, 3H), 2.14 (s, 3H), 1.95-1.60 (m, 4H). |
| 25 | | RT 4.51 min, MI 420, Method (1LCMS1). |
| 26 | | RT 3.43 min, MI 417, Method (1LCMS1) |

Synthesis of 5-chloro-4-(1-isobutyl-4-piperidyl)-2-(4-methylthiazol-5-yl)-1H-pyrimidin-6-one (27)

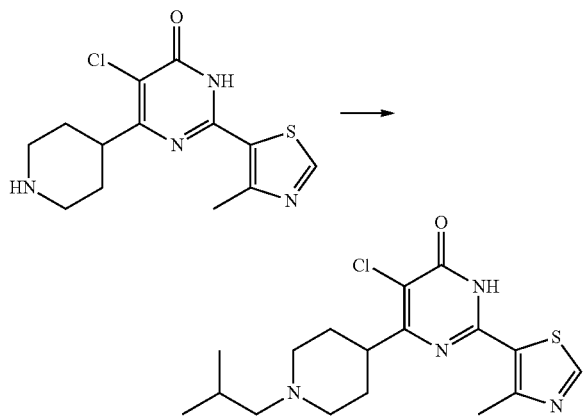

To a solution of 5-chloro-2-(4-methylthiazol-5-yl)-4-(4-piperidyl)-1H-pyrimidin-6-one (2) (0.104 g, 0.300 mmol) in glacial acetic acid (10 mL) was added isobutyraldehyde (0.435 mL, 4.800 mmol) and the mixture was left to stir at room temperature for 4 h. Sodium triacetoxyborohydride (0.318 g, 1.50 mmol) was added and stirring continued for 18 h. After this time the reaction mixture was concentrated under vacuum and the residue was partitioned between DCM and a saturated aqueous solution of NaHCO$_3$. The DCM phase was dried (Na$_2$CO$_3$), filtered and concentrated under vacuum. The residue was purified by reverse phase column chromatography to give the title compound (0.020 g, 18%). LCMS: RT 1.89 min, MI 367, Method (1LCMS1); $^1$H NMR (300 MHz, DMSO-d$_6$+2 eq d-TFA) δ 13.56 (br s, 2H), 9.13 (s, 1H), 3.59 (d, J=12.2 Hz, 2H), 3.42-3.25 (m, 1H), 3.17-3.00 (m, 2H), 2.93 (d, J=7.2 Hz, 2H), 2.72 (s, 3H), 2.22-2.03 (m, 3H), 2.00-1.85 (m, 2H), 0.96 (d, J=6.6 Hz, 6H).

General Scheme 2

In one approach (General Scheme 2), compounds of general formula [F2-3] were prepared by the reaction of an α-halo-malonate derivative of general formula [F2-1] in a condensation reaction utilising a suitably substituted heterocyclic carboximidamide derivative of general formula [F2-2] in a polar solvent such as methanol or THF in the presence of a base such as sodium methoxide, potassium tert-butoxide or DBU. The reaction is suitably conducted at ambient temperature or at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. Derivatives of general formula [F2-4] were prepared by the reaction of a 5-halo-2-heterocyclyl-1H-pyrimidine-4,6-dione derivative of general formula [F2-3] with a halogenating agent such as phosphorous oxychloride at high temperature. After reaction work up, typically by the addition of water followed by the addition of a base such as aqueous sodium hydroxide, the crude reaction mixture was purified by liquid-liquid extraction, and the reaction product was used crude in the next step or purified by flash column chromatography, reverse phase preparative HPLC or re-crystallisation. Derivatives of general formula [F2-5] were prepared by a hydrolysis reaction of a 4,5,6-halo-2-heterocyclyl-pyrimidine derivative of general formula [F2-4] with a mineral acid such as HCl or H$_2$SO$_4$ or an aqueous base such as NaOH at high temperature. After reaction work up, typically by a liquid-liquid extraction, the reaction product was used crude in the next step or purified by flash column chromatography, reverse phase preparative HPLC or re-crystallisation. Compounds of general formula [F2-7] were prepared by reaction of 5,6-dichloro-2-heterocyclyl-3H-pyrimidin-4-one derivatives of general formula [F2-5] in a nucleophilic aromatic substitution type reaction utilising a suitable amine of general formula [F2-6], and a base such as Et$_3$N or NaH, or a mineral acid such as HCl, in a polar solvent such as ethanol, butanol, dioxane, DMA or DMF at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. In cases where the heterocycle (het) or substituent R' or R" contained an amine protected by a standard amine protecting group such as a tert-butyloxycarbonyl (Boc), compounds of formula [F2-7] can be prepared by a suitable deprotection reaction, for example reaction with an acid such as TFA in a suitable solvent such as DCM at ambient temperature. After reaction work up, typically by a liquid-liquid extraction or purification by acidic ion exchange catch-release the crude product was purified by flash column chromatography, reverse phase preparative HPLC or re-crystallisation.

General Scheme 2

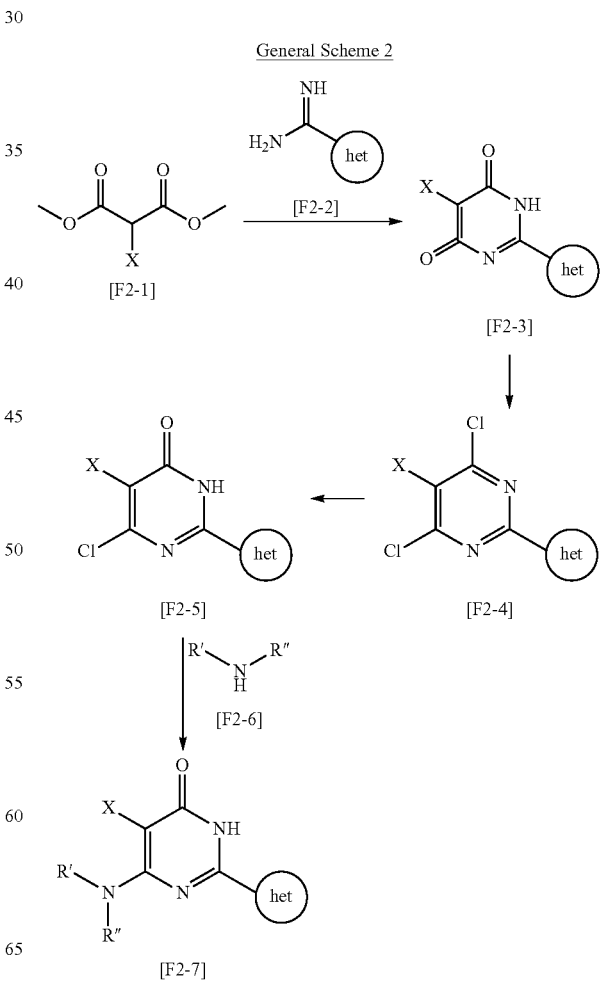

Synthesis of 5-chloro-2-(4-methylthiazol-5-yl)-1H-pyrimidine-4,6-dione (2-001)

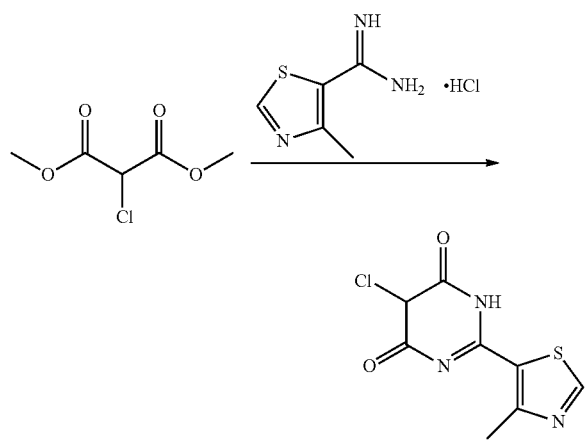

To a solution of 4-methylthiazole-5-carboxamidine hydrochloride (1-001) (1.936 g, 10.90 mmol) in MeOH (50 mL) under nitrogen was added dimethyl chloromalonate (1.53 mL, 11.99 mmol) followed by DBU (6.50 mL, 43.60 mmol) (exotherm observed). The reaction mixture was then stirred at room temperature for 24 h under nitrogen before concentrating under vacuum. The oily residue was treated by the addition of 1 M aqueous HCl until pH 2 was reached. The cream suspension was diluted with water (30 mL) then filtered through a sintered funnel and washed with 0.5 M aqueous HCl (30 mL). The collected cream paste was taken into MeOH then sonicated for 40 min. The suspension was collected by vacuum filtration then allowed to dry by vacuum suction overnight to give the title compound (2.25 g, 85%) as a beige solid. LCMS: RT 2.70 min, MI 243, Method (1LCMS1).

Synthesis of 4-methyl-5-(4,5,6-trichloropyrimidin-2-yl)thiazole (2-002)

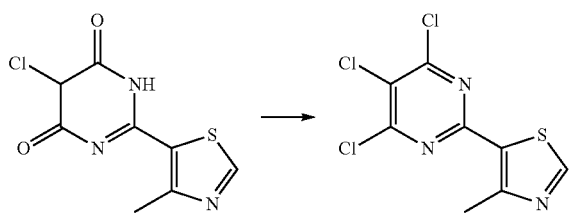

In a 50 mL round bottom flask under nitrogen, 5-chloro-2-(4-methylthiazol-5-yl)-1H-pyrimidine-4,6-dione (2-001) (2.25 g, 9.23 mmol) was added to $POCl_3$ (25 mL) and the reaction mixture was heated to 120° C. for 16 h before cooling to room temperature. The reaction mixture was then carefully added to ice under vigorous stirring. The obtained suspension was filtered through a sintered funnel. The filtrate was extracted with DCM (×3) then neutralised and extracted with further DCM (×3). The combined organic phases were concentrated under vacuum to give the title compound (1.40 g, 54%) as a beige powder. LCMS: RT 6.37 min, MI 282, Method (1LCMS1).

Synthesis of 4,5-dichloro-2-(4-methylthiazol-5-yl)-1H-pyrimidin-6-one (2-003)

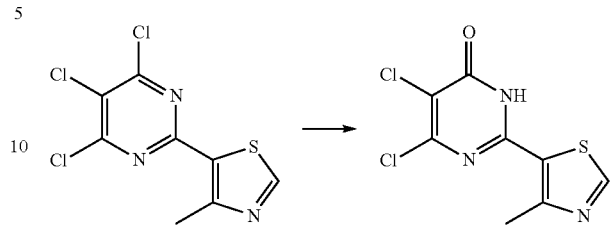

In a 25 mL round bottom flask equipped with an air condenser, 4-methyl-5-(4,5,6-trichloropyrimidin-2-yl)thiazole (2-002) (1.40 g, 5.00 mmol) was added to concentrated HCl (25 mL) and the reaction mixture was refluxed for 4 days. The reaction mixture was then cooled to room temperature and the suspension was filtered through a sintered funnel. The collected solid was washed with water then dried by vacuum filtration to give the title compound (1.18 g, 90%) as a beige powder. LCMS: RT 5.65 min, MI 262, Method (1 LCMS1).

Synthesis of 5-chloro-2-(4-methylthiazol-5-yl)-4-[(3R)-3-(trifluoromethyl)piperazin-1-yl]-1H-pyrimidin-6-one (28)

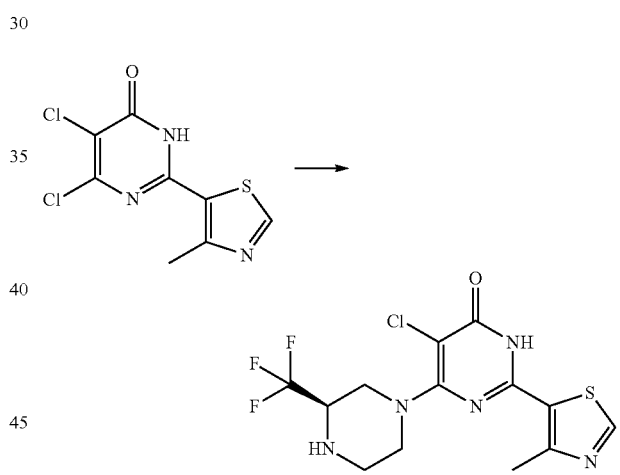

To a solution of 4,5-dichloro-2-(4-methylthiazol-5-yl)-1H-pyrimidin-6-one (2-003) (0.100 g, 0.382 mmol) in EtOH (2.5 mL) was added (2R)-2-(trifluoromethyl)piperazine (0.145 g, 0.763 mmol) followed by $Et_3N$ (0.212 mL, 1.526 mmol). The mixture was heated in the microwave at 150° C. for 45 min. The dark brown reaction mixture was allowed to cool to room temperature then sonicated for 15 min. The suspension was concentrated under vacuum, the residue taken into DMSO (2 mL) and heated until dissolution then allowed to crystallise. The suspension was filtered through a sintered funnel. The filtrate was purified by preparative HPLC to give the title compound (0.095 g, 66%) as an off-white powder. LCMS: RT 3.51 min, MI 378.3/380.3, Method (1LCMS1); $^1$H NMR (300 MHz, DMSO-$d_6$) δ 9.07 (s, 1H), 4.18 (d, J=12.7 Hz, 1H), 3.98 (d, J=13.0 Hz, 1H), 3.61-3.46 (m, 1H), 3.24-3.06 (m, 2H), 3.00-2.92 (m, 1H), 2.82-2.63 (m, 4H).

The following compounds were synthesised according to the general synthesis shown in scheme [2]:

| No | Product [F2-7] | Characterisation |
|---|---|---|
| 29 | | RT 3.72 min, MI 327/329, Method (1LCMS1); $^1$H NMR (300 MHz, DMSO-d$_6$) δ 12.41 (s, 1H), 9.06 (s, 1H), 4.75 (d, J = 4.1 Hz, 1H), 3.94 (dt, J = 13.2, 4.2 Hz, 2H), 3.78-3.63 (m, 1H), 3.21 (ddd, J = 13.0, 9.7, 2.9 Hz, 2H), 2.71 (s, 3H), 1.88-1.76 (m, 2H), 1.45 (dtd, J = 12.7, 9.2, 3.6 Hz, 2H). |
| 30 | | RT 5.72 min, MI 325/329, Method (1LCMS1); $^1$H NMR (300 MHz, DMSO-d$_6$) δ 9.03 (s, 1H), 4.16 (d, J = 13.0 Hz, 2H), 2.90 (t, J = 11.7 Hz, 2H), 2.71 (s, 3H), 1.78-1.47 (m, 3H), 1.33-1.07 (m, 2H), 0.91 (d, J = 6.3 Hz, 3H). |
| 31 | | RT 3.55 min, MI 380/382, Method (1LCMS1); $^1$H NMR (300 MHz, DMSO-d$_6$) δ 9.07 (s, 1H), 4.18 (d, J = 11.4 Hz, 1H), 3.98 (d, J = 13.0 Hz, 1H), 3.62-3.44 (m, 1H), 3.23-3.06 (m, 2H), 3.02-2.90 (m, 1H), 2.80-2.66 (m, 4H). |
| 32 | | RT 1.57 min, MI 326/328, Method (1LCMS1); $^1$H NMR (300 MHz, DMSO-d$_6$) δ 16.12 (br s, 2H), 9.12 (s, 1H), 4.17 (t, J = 13.3 Hz, 2H), 3.48-3.25 (m, 3H), 3.21-3.04 (m, 2H), 2.71 (s, 3H), 1.23 (d, J = 6.5 Hz, 3H). |
| 33 | | RT 4.04 min, MI 341/343, Method (1LCMS1); $^1$H NMR (500 MHz, methanol-d$_4$) δ 9.57 (s, 1H), 4.45 (d, J = 13.1 Hz, 2H), 3.46 (d, J = 6.2 Hz, 2H), 3.03 (t, J = 12.7 Hz, 2H), 2.88 (s, 3H), 1.90-1.72 (m, 3H), 1.43-1.31 (m, 2H). |
| 34 | | RT 3.04 min, MI 340.0/341.9, Method (1LCMS1); $^1$H NMR (300 MHz, DMSO-d$_6$) δ 12.19 (br s, 1H), 9.05 (s, 1H), 7.59 (t, J = 4.7 Hz, 1H), 4.30 (s, 2H), 3.79 (t, J = 5.8 Hz, 2H), 3.23-3.06 (m, 2H), 2.69 (s, 3H), 2.05-1.87 (m, 2H). |
| 35 | | RT 4.82 min, MI 347.0/348.9, Method (1LCMS1); $^1$H NMR (300 MHz, DMSO-d$_6$) δ 8.93 (s, 1H), 3.72 (t, J = 11.9 Hz, 2H), 3.50-3.36 (m, 2H), 2.72 (s, 3H), 2.17-1.95 (m, 2H), 1.91-1.74 (m, 2H). |

-continued

| No | Product [F2-7] | Characterisation |
|---|---|---|
| 36 | (structure) | RT 4.29 min, MI 341.0/343.0, Method (1LCMS1); $^1$H NMR (300 MHz, DMSO-$d_6$) δ 12.37 (s, 1H), 9.06 (s, 1H), 4.59-4.48 (m, 1H), 4.26 (d, J = 12.3 Hz, 1H), 4.11 (d, J = 12.9 Hz, 1H), 3.39-3.18 (m, 2H), 2.95 (t, J = 11.0 Hz, 1H), 2.80-2.65 (m, 4H), 1.80-1.61 (m, 3H), 1.61-1.41 (m, 1H), 1.30-1.08 (m, 1H). |
| 37 | (structure) ·HCl | RT 1.41 min, MI 326.1/328.0, Method (1LCMS1); $^1$H NMR (300 MHz, DMSO-$d_6$) δ 15.03 (br s, 2H), 9.11 (s, 1H), 4.17 (t, J = 13.4 Hz, 2H), 3.49-3.22 (m, 3H), 3.22-3.02 (m, 2H), 2.70 (s, 3H), 1.23 (d, J = 6.5 Hz, 3H). |
| 38 | (structure) ·HCl | RT 1.04 min, MI 312.0/314.0, Method (2LCMS1) |
| 39 | (structure) ·HCl | RT 2.11 min, M: 354.1/356.1, Method (1LCMS1); |

General Scheme 3

In one approach (General Scheme 3), compounds of general formula [F3-3] were prepared by the reaction of a 4,6-dichloro-5-halo-2-iodo-pyrimidine derivative of general formula [F3-1] in a nucleophilic aromatic substitution type reaction utilising a suitable amine of general formula [F3-2], and a base such as Et$_3$N or N,N-diisopropylethylamine in a polar solvent such as ethanol, 1,4-dioxane, DMA or DMF at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. 4-Chloro-5-halo-2-heterocyclyl-pyrimidine derivatives of general formula [F3-5] were prepared by a Suzuki-type coupling reaction with a suitable boronic acid or boronate ester of general formula [F3-4] utilising a suitable catalyst such as bis(triphenylphosphine)palladium(II) dichloride, tetrakis(triphenylphosphine)palladium, or 1,1'-bis(diphenylphosphino)ferrocene]dichloropalladium(II), and a base such as sodium carbonate, potassium carbonate or cesium carbonate, in a polar solvent mixture such as 1,4-dioxane/water at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. 5-Halo-(2-heterocyclyl)-3H-pyrimidin-4-one derivatives of general formula [F3-6] were prepared by a hydrolysis reaction of 4-chloro-5-halo-2-(heterocyclyl)-pyrimidine derivatives of general formula [F3-5] with an aqueous base such as NaOH or KOH at high temperature either by heating thermally or using a microwave reactor. After reaction work up, typically by a liquid-liquid extraction or purification by acidic ion exchange catch-release the crude product was purified by flash column chromatography, reverse phase preparative HPLC or re-crystallisation. In cases where the heterocycle (het) or substituent R' or R" contained an amine protected by a standard amine protecting group such as tert-butyloxycarbonyl (Boc), compounds of formula [F3-6] are prepared by a suitable deprotection reaction, for example reaction with an acid such as TFA or HCl in a suitable solvent such as DCM at ambient temperature. After reaction work up, typically by a liquid-liquid extraction or purification by acidic ion exchange catch-release the crude product was purified by flash column chromatography, reverse phase preparative HPLC or re-crystallisation.

General Scheme 3

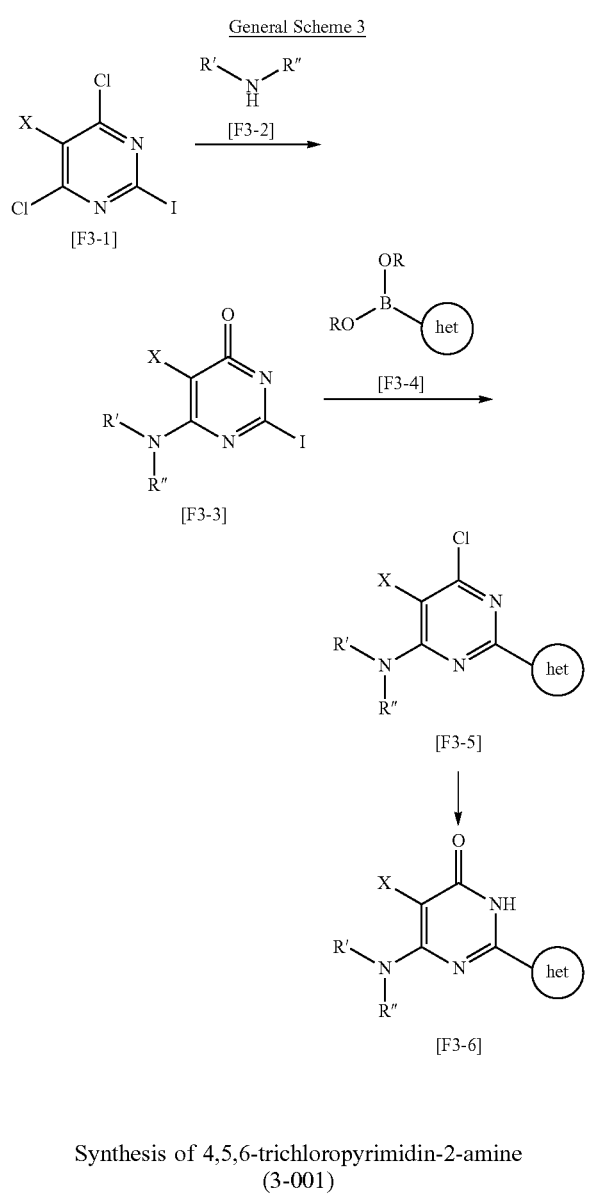

Synthesis of 4,5,6-trichloropyrimidin-2-amine (3-001)

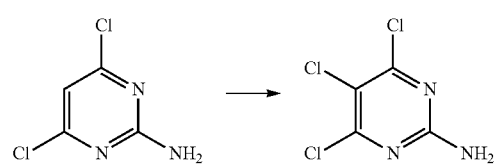 [SMILES: Nc1nc(Cl)cc(Cl)n1 ; Nc1nc(Cl)c(Cl)c(Cl)n1]

A suspension of 2-amino-4,6-dichloropyrimidine (2.0 g, 12.20 mmol) in chloroform (30 mL) was prepared and N-chlorosuccinimide (1.71 g, 12.81 mmol) was added portionwise. The reaction mixture was refluxed for 2 h. The reaction mixture was cooled to room temperature, diluted with a saturated solution of NaHCO₃ then extracted with DCM and ethyl acetate. A precipitate formed which was removed by filtration. The combined organic extracts were dried and concentrated under reduced pressure. The crude residue was purified by flash chromatography on silica gel, eluting with 0-40% EtOAc in cyclohexane. The appropriate fractions were combined and concentrated to give the title compound (2.1 g, 86.8% yield). LCMS: RT 4.03 min, MI 199.8, Method (4LCMS1)

Synthesis of 4,5,6-trichloro-2-iodo-pyrimidine (3-002)

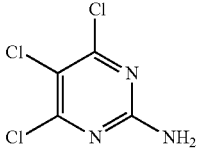

4,5,6-Trichloropyrimidin-2-amine (3-001) (5.0 g, 25.20 mmol) and di-iodomethane (20.3 mL, 251.96 mmol) were suspended in MeCN (25 mL). This was then treated with the dropwise addition tert-butyl nitrite (15.04 mL, 125.98 mmol). The reaction turned pale green and a gas was given off. The reaction mixture was heated to 80° C. for 2 hours before allowing to cool to room temperature and treating with saturated sodium bicarbonate solution (gas evolved). The reaction was then extracted into DCM (2×50 mL), the organics dried and concentrated under reduced pressure. The crude product was purified by flash chromatography on silica gel, eluting with cyclohexane containing 0-5% EtOAc. The appropriate fractions were combined and concentrated to give the title compound (4.13 g, 53% yield) as a white solid. LCMS: RT 4.98 min, MI 310, Method (4LCMS1).

Synthesis of tert-butyl 4-(5,6-dichloro-2-iodo-pyrimidin-4-yl)-6,6-difluoro-1,4-diazepane-1-carboxylate (3-003)

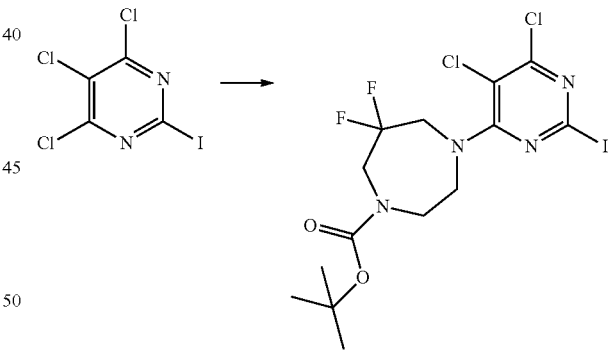

To a solution of 4,5,6-trichloro-2-iodo-pyrimidine (3-002) (0.50 g, 1.62 mmol) in 1,4-dioxane (5 mL) and N,N-diisopropylethylamine (0.56 mL, 3.23 mmol) was added tert-butyl 6,6-difluoro-1,4-diazepane-1-carboxylate (0.42 g, 1.778 mmol) as a solution in 1,4-dioxane (5 mL) and the reaction was allowed to stir at room temperature overnight. The reaction was concentrated and the residue was purified by column chromatography eluting with an EtOAc/hexane gradient (10-30% EtOAc). Fractions containing the product were combined and concentrated under reduced pressure to give the title compound (500 mg, 60.8% yield) as a colourless oil. LCMS: RT 5.70 min, MI 508/510, Method (4LCMS1). ¹H NMR (400 MHz, DMSO-d₆) δ 4.68-4.01 (m, 2H), 4.08-3.49 (m, 6H), 1.41 (s, 9H).

Synthesis of 4-iodo-1-[(4-methoxyphenyl)methyl]pyrazole (3-004)

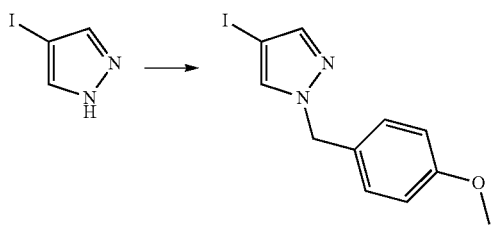

4-Iodopyrazole (10.0 g, 51.55 mmol) was dissolved in 1,4-dioxane (40 mL) and to this was added potassium carbonate (7.12 g, 51.55 mmol) followed by 4-methoxybenzyl chloride (6.99 mL, 51.55 mmol) and the reaction was stirred at reflux overnight. Upon cooling, the reaction mixture was concentrated and the residue was partitioned between ethyl acetate and water. The organic phase was washed with brine, dried over sodium sulphate, filtered and evaporated to give a yellow oil. This was purified by column chromatography eluting with an ethyl acetate/hexane gradient, 0-30% ethyl acetate. Fractions containing product were combined and evaporated to give the title compound (9.20 g, 57%) as a straw coloured oil which crystallized on standing. $^1$H NMR (400 MHz, DMSO-$d_6$) δ 7.98 (d, J=0.7 Hz, 1H), 7.52 (d, J=0.7 Hz, 1H), 7.28-7.17 (m, 2H), 6.98-6.85 (m, 2H), 5.24 (s, 2H), 3.73 (s, 3H).

Synthesis of 5-chloro-4-iodo-1-[(4-methoxyphenyl)methyl]pyrazole (3-005)

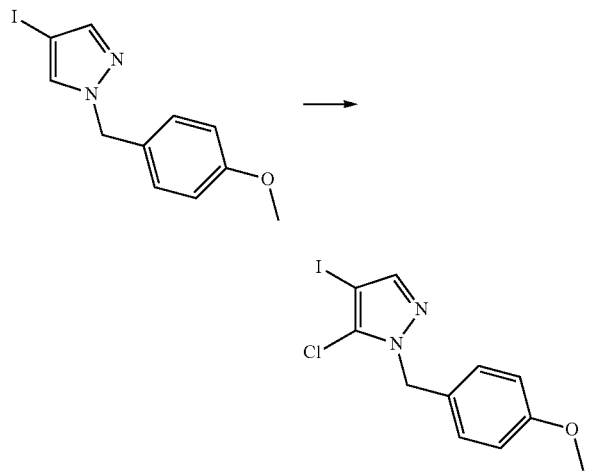

A stirred solution of diisopropylamine (3.01 mL, 21.49 mmol) in THF (10 mL) was prepared under nitrogen and cooled to −78° C. n-Butyllithium (2.5 M) in hexanes (8.28 mL, 20.69 mmol) was added and the reaction mixture warmed to 0° C. and stirred at this temperature for ten minutes. The reaction mixture was then cooled back to −78° C. This solution was added dropwise to a −78° C. solution of 4-iodo-1-[(4-methoxyphenyl)methyl]pyrazole (3-004) (5.00 g, 15.92 mmol) in tetrahydrofuran (10 mL) over two minutes. After five minutes, hexachloroethane (4.52 g, 19.10 mmol) diluted in the minimum amount of THF was added and stirring was continued at −78° C. for 1 h. The solution was then allowed to warm to room temperature. Saturated aqueous ammonium chloride was added and the mixture was extracted with ethyl acetate (2×50 mL). The organic layers were combined, dried over sodium sulphate, filtered and evaporated. The resulting residue was purified by flash chromatography on silica gel eluting with tert-butylmethyl ether/petroleum ether gradient, 0-20% TBME. Fractions containing product were combined and evaporated to give the title compound (4.40 g, 79%) as a yellow solid. $^1$H NMR (400 MHz, DMSO-$d_6$) δ 7.71 (s, 1H), 7.16 (d, J=8.6 Hz, 2H), 6.91 (d, J=8.7 Hz, 2H), 5.35 (s, 2H), 3.73 (s, 3H).

Synthesis of 5-chloro-1-[(4-methoxyphenyl)methyl]-4-(4,4,5,5-tetramethyl-1,3,2-dioxaborolan-2-yl)pyrazole (3-006)

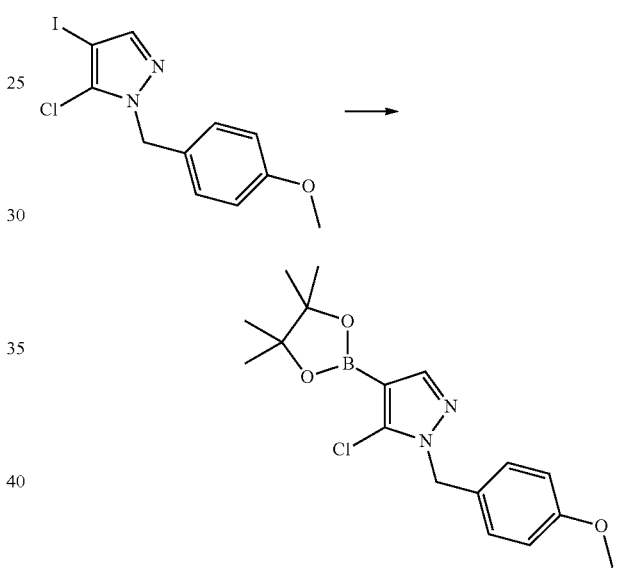

5-Chloro-4-iodo-1-[(4-methoxyphenyl)methyl]pyrazole (3-005) (5.30 g, 15.20 mmol) was dissolved in acetonitrile (4 mL) and to this was added palladium acetate (68.27 mg, 0.304 mmol), copper (I) iodide (0.579 g, 3.04 mmol), triphenylphosphine (79.76 mg, 0.304 mmol), cesium carbonate (7.431 g, 22.81 mmol) and bis(pinacolato)diboron (5.79 g, 22.81 mmol) and the reaction was stirred at room temperature overnight. To the reaction was added a further portion of copper (I) iodide (0.579 g, 3.04 mmol), triphenylphosphine (79.76 mg, 0.304 mmol), palladium acetate (68.27 mg, 0.304 mmol) and the reaction was stirred at room temperature for 5 h. The reaction was concentrated and the residue was purified by column chromatography using an ethyl acetate/petroleum ether gradient eluting with 0-20% ethyl acetate. Fractions containing product were combined and concentrated to give the title compound (3.00 g, 57%) as a colourless oil which crystallized on standing. LCMS: RT 5.06 min, MI 348, Method (4LCMS3); $^1$H NMR (400 MHz, DMSO-$d_6$) δ 7.70 (s, 1H), 7.15 (d, J=8.7 Hz, 2H), 6.90 (d, J=8.7 Hz, 2H), 5.30 (s, 2H), 3.73 (s, 3H), 1.16 (s, 12H).

Synthesis of tert-butyl 4-[5,6-dichloro-2-[5-chloro-1-[(4-methoxyphenyl)methyl]pyrazol-4-yl]pyrimidin-4-yl]-6,6-difluoro-1,4-diazepane-1-carboxylate (3-007)

Synthesis of tert-butyl 4-[5-chloro-2-[5-chloro-1-[(4-methoxyphenyl)methyl]pyrazol-4-yl]-6-oxo-1H-pyrimidin-4-yl]-6,6-difluoro-1,4-diazepane-1-carboxylate (3-008)

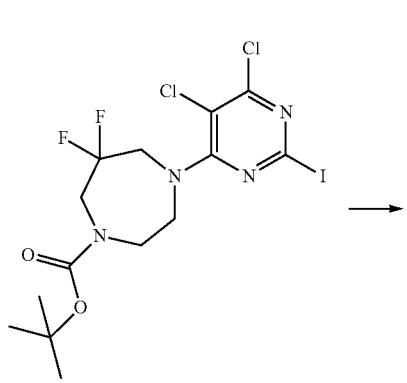

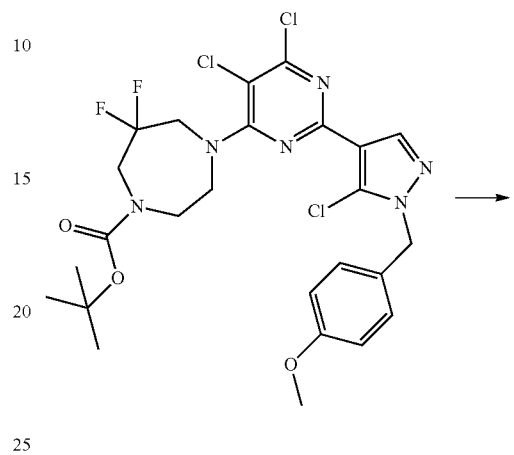

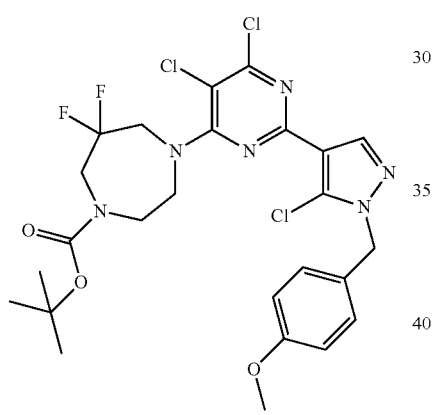

tert-Butyl 4-(5,6-dichloro-2-iodo-pyrimidin-4-yl)-6,6-difluoro-1,4-diazepane-1-carboxylate (3-003) (0.250 g, 0.491 mmol), 5-chloro-1-[(4-methoxyphenyl)methyl]-4-(4,4,5,5-tetramethyl-1,3,2-dioxaborolan-2-yl)pyrazole (3-006) (0.21 g, 0.589 mmol), 1,1'-bis(diphenylphosphino)ferrocene]dichloropalladium(II), complex with dichloromethane (0.04 g, 0.049 mmol), and sodium hydrogen carbonate (0.080 g, 0.982 mmol), were treated with 1,4-dioxane (5 mL) and water (1 mL) and heated to 100° C. overnight. This was then diluted with water (100 mL) which was then extracted into DCM (2×100 mL) and EtOAc (100 mL). The organic fractions were combined and evaporated. The residue was purified by flash chromatography on silica gel (eluting with 0-20% ethyl acetate in cyclohexane). The fractions containing the product were combined and evaporated to give the title compound (110 mg, 37%). LCMS: RT 6.20 min, MI 605, Method (4LCMS1).

tert-Butyl 4-[5,6-dichloro-2-[5-chloro-1-[(4-methoxyphenyl)methyl]pyrazol-4-yl]pyrimidin-4-yl]-6,6-difluoro-1,4-diazepane-1-carboxylate (3-007) (0.110 g, 0.182 mmol) was dissolved in 1,4-dioxane (2 mL) and treated with 2 M aqueous NaOH (1.09 mL, 2.19 mmol). This was then heated in the microwave to 120° C. for 60 minutes. The reaction mixture was then diluted by the addition of DCM and washed with water. The DCM layer was evaporated and the residue purified by flash chromatography on silica gel (eluting with 0-100% ethyl acetate in cyclohexane followed by 0-10% methanol in DCM). The fractions containing the product were combined and evaporated to give the title compound (45 mg, 42%). LCMS: RT 4.95 min, MI 585, Method (4LCMS1); $^1$H NMR (400 MHz, DMSO-$d_6$) δ 12.63 (s, 1H), 8.39 (s, 1H), 7.22 (d, J=8.7 Hz, 2H), 6.99-6.85 (m, 2H), 5.37 (s, 2H), 4.38 (t, J=12.6 Hz, 2H), 3.80 (d, J=14.3 Hz, 6H), 3.73 (s, 3H), 1.39 (d, J=12.5 Hz, 9H).

Synthesis of 5-chloro-2-(5-chloro-1H-pyrazol-4-yl)-4-(6,6-difluoro-1,4-diazepan-1-yl)-1H-pyrimidin-6-one hydrochloride (40)

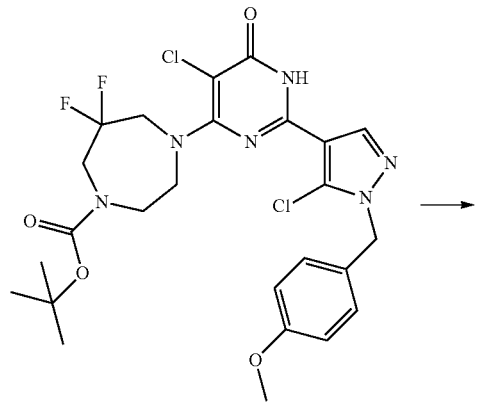

tert-Butyl 4-[5-chloro-2-[5-chloro-1-[(4-methoxyphenyl)methyl]pyrazol-4-yl]-6-oxo-1H-pyrimidin-4-yl]-6,6-difluoro-1,4-diazepane-1-carboxylate (3-008) (0.050 g, 0.077 mmol) was dissolved in TFA (1.00 mL, 0.077 mmol) and DCM (1 mL) and left to stir at room temperature for 4 hours, then 80° C. for 2 hours. The reaction mixture was then allowed to return to room temperature and evaporated to dryness. The residue was treated with 2 M HCl in diethyl ether (1 mL), the reaction was filtered and washed with ether. The solid was then dissolved in DMSO and purified by preparative HPLC. The fractions recovered were then treated with 2 M HCl in diethyl ether (1 mL) and evaporated to give the title compound (12 mg, 39%). LCMS: RT 1.74 min, MI 365, Method (4LCMS1); $^1$H NMR (400 MHz, DMSO-$d_6$) δ 13.71 (s, 1H), 12.61 (s, 1H), 8.64 (s, 1H), 4.60 (t, J=13.3 Hz, 2H), 4.01 (d, J=5.5 Hz, 2H), 3.76 (t, J=12.9 Hz, 2H), 3.56-3.42 (m, 2H).

Synthesis of (3R)-4-(5,6-dichloro-2-iodo-pyrimidin-4-yl)-3-methyl-morpholine (3-009)

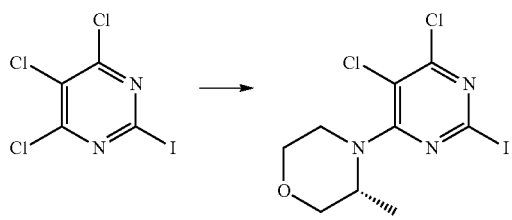 [SMILES: Clc1nc(I)nc(Cl)c1Cl ; C[C@@H]1COCCN1c1nc(I)nc(Cl)c1Cl]

To a stirred solution of 4,5,6-trichloro-2-iodo-pyrimidine (3-002) (2.00 g, 6.47 mmol) and triethylamine (0.950 mL, 6.79 mmol) in chloroform (60 mL) was added (R)-3-methylmorpholine (0.730 mL, 6.47 mmol). The reaction mixture was stirred at room temperature under nitrogen for 100 h. Water (30 mL) was added and the two phases were separated. The aqueous was further extracted with DCM (2×15 mL). The combined organics were dried (phase separator) and concentrated to a yellow oil. The oil was purified using flash chromatography on silica gel eluting with a mixture of ethyl acetate in petroleum ether (0-50%). Desired fractions were concentrated affording the title compound (1.53 g, 63%) as a white powder. LCMS: 5.25 min, MI 374, method (4LCMS1); $^1$H NMR (400 MHz, CDCl$_3$) δ 4.55 (qd, J=6.9, 3.0 Hz, 1H), 4.17-4.07 (m, 1H), 3.94 (ddd, J=11.3, 3.4, 1.4 Hz, 1H), 3.71 (d, J=2.2 Hz, 2H), 3.62 (td, J=11.7, 2.5 Hz, 1H), 3.54-3.43 (m, 1H), 1.43 (d, J=6.8 Hz, 3H).

Synthesis of (3R)-4-[5,6-dichloro-2-[5-(trifluoromethyl)-1H-pyrazol-4-yl]pyrimidin-4-yl]-3-methyl-morpholine (3-010)

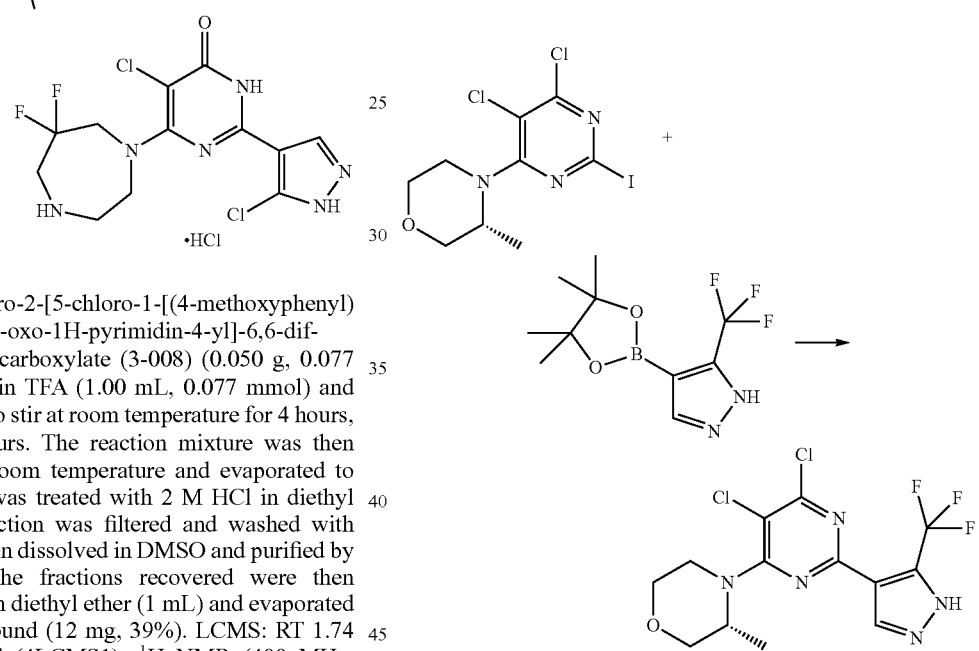

(3R)-4-(5,6-dichloro-2-iodo-pyrimidin-4-yl)-3-methyl-morpholine (3-009) (0.630 g, 1.68 mmol), 4-(4,4,5,5-tetramethyl-1,3,2-dioxaborolan-2-yl)-5-(trifluoromethyl)-1H-pyrazole (0.440 g, 1.68 mmol), 1,1'-bis(diphenylphosphino)ferrocene]dichloropalladium(II), complex with dichloromethane (0.140 g, 0.168 mmol), and sodium hydrogen carbonate (0.280 g, 3.37 mmol) were treated with 1,4-dioxane (1.5 mL) and water (0.5 mL) and heated to 120° C. in the microwave for 20 minutes. This was then diluted with DCM (20 mL) and washed with water (20 mL). The DCM was then evaporated and purified by flash chromatography on silica gel (eluting with 0-50% ethyl acetate in cyclohexane). The fractions containing the product were combined and evaporated to give the title compound (0.550 g, 85%). LCMS: RT 4.93 min, MI 382, Method (4LCMS1); $^1$H NMR (400 MHz, DMSO-$d_6$) (13.99 (s, 1H), 8.74-8.39 (m, 1H), 4.50 (d, J=7.3 Hz, 1H), 4.14-4.04 (m, 1H), 3.89 (d, J=11.2 Hz, 1H), 3.71-3.40 (m, 3H), 1.40 (s, 1H), 1.36 (d, J=6.8 Hz, 3H).

Synthesis of 5-chloro-4-[(3R)-3-methylmorpholin-4-yl]-2-[5-(trifluoromethyl)-1H-pyrazol-4-yl]-1H-pyrimidin-6-one (41)

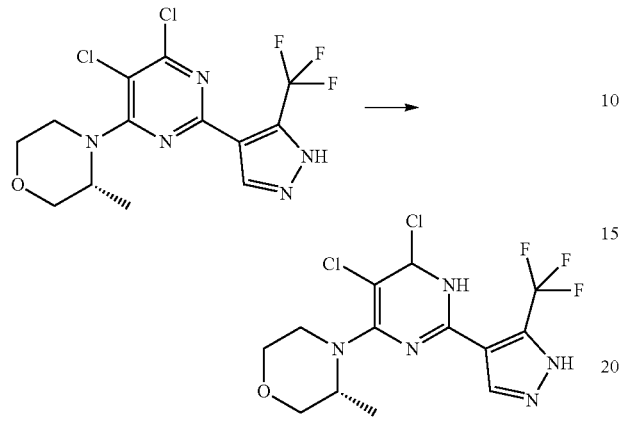

(3R)-4-[5,6-dichloro-2-[5-(trifluoromethyl)-1H-pyrazol-4-yl]pyrimidin-4-yl]-3-methyl-morpholine (3-010) (0.550 g, 1.44 mmol) was treated with 1,4-dioxane (8.6 mL) and 2 M aqueous sodium hydroxide (8.63 mL, 17.27 mmol) and heated to 100° C. for 3 days. The reaction mixture was cooled to room temperature overnight then cooled to 5° C. in an ice bath and treated with saturated sodium citrate (10 mL), a white precipitate was formed. The mixture was treated with ethyl acetate (75 mL) and water (25 mL) and gently mixed. The layers were separated and the aqueous was extracted with further ethyl acetate (75 mL). The organic layers were combined, washed with water (50 mL) then brine (50 mL), and passed through a phase separator and the filtrate evaporated. The residue was purified by flash chromatography on silica gel, eluting with 0-100% ethyl acetate then 0-10% methanol in DCM. The appropriate fractions were combined and concentrated under reduced pressure to give a pale yellow solid. The solid was suspended in diethyl ether, filtered, washed with more ether and dried overnight in a vacuum oven. The solid was then suspended in methanol and concentrated. The residue was suspended in water and then concentrated. The residue was purified by SCX, washing first with methanol then with 2 M methanolic ammonia. The first fraction eluted was evaporated to give the title compound (0.029 g, 6%) as a yellow powder. LCMS: RT 3.45 min, MI 364, Method (4LCMS1); $^1$H NMR (400 MHz, DMSO-$d_6$) δ 14.09 (s, 1H), 12.57 (s, 1H), 8.70 (s, 1H), 4.37 (d, J=7.3 Hz, 1H), 3.86 (t, J=12.4 Hz, 2H), 3.70-3.35 (m, 4H), 1.30 (d, J=6.8 Hz, 3H).

Synthesis of 1-[(4-methoxyphenyl)methyl]-4-(4,4,5,5-tetramethyl-1,3,2-dioxaborolan-2-yl)-5-(trifluoromethyl)pyrazole (3-011)

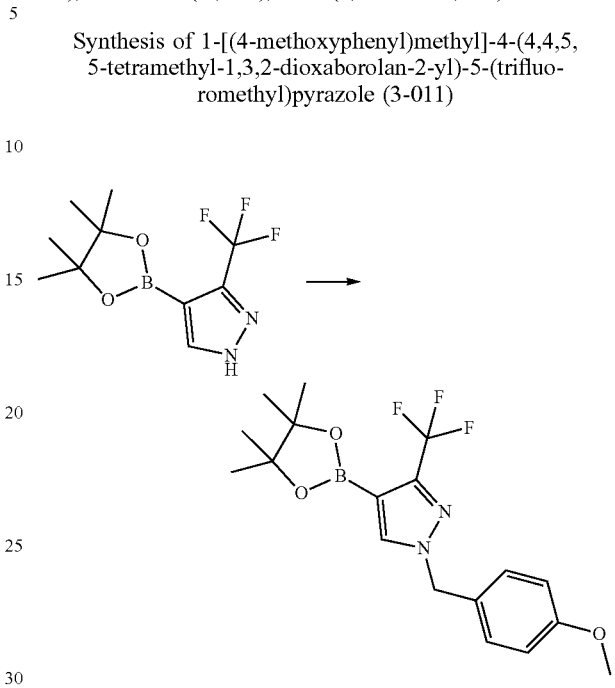

Potassium carbonate (678.8 g, 4911 mmol) was added to a solution of 4-(4,4,5,5-tetramethyl-1,3,2-dioxaborolan-2-yl)-5-(trifluoromethyl)-1H-pyrazole (2.00 g, 7.63 mmol) in MeCN (30 mL) followed by 4-methoxybenzyl chloride (1.03 mL, 7.63 mmol) and the reaction mixture was refluxed overnight. The mixture was concentrated under reduced pressure and the residue diluted with brine and EtOAc. The aqueous phase was extracted with EtOAc. The organic solvent was dried over MgSO$_4$, filtered and concentrated under reduced pressure. The residue was purified by flash chromatography on silica gel, eluting with 0-30% EtOAC:cyclohexane. Fractions containing product were combined and evaporated to give the title compound (2.27 g, 78%) as a mixture of pyrazole isomers. LCMS: RT 3.46/3.59 min, MI 383, Method (1 LCMS13).

The following compounds were synthesised according to the general synthesis shown in scheme [3]:

| No | [F3-4] | Product [F3-6] | Characterisation |
|---|---|---|---|
| 42 | (structure) | (structure) | RT 3.09 min, MI 329/331, Method (4LCMS1); $^1$H NMR (400 MHz, DMSO-$d_6$) δ 13.62 (s, 1H), 12.39 (s, 1H), 8.60 (s, 1H), 4.46 (d, J = 7.1 Hz, 1H), 4.20-3.93 (m, 1H), 3.93-3.76 (m, 1H), 3.69-3.58 (m, 2H), 3.53 (td, J = 11.4, 2.6 Hz, 1H), 3.38 (m 1H), 1.33 (d, J = 6.8 Hz, 3H). |

-continued

| No | [F3-4] | Product [F3-6] | Characterisation |
|---|---|---|---|
| 43 | | | RT 1.68 min, MI 329, Method (4LCMS1); $^1$H NMR (400 MHz, DMSO-$d_6$) δ 13.72 (s, 1H), 12.58 (s, 1H), 9.67-9.20 (m, 1H), 9.02 (s, 1H), 8.63 (s, 1H), 4.60 (dd, J = 7.3, 3.8 Hz, 1H), 4.14 (d, J = 14.7 Hz, 1H), 3.43 (ddd, J = 14.6, 11.7, 2.8 Hz, 1H), 3.27 (d, J = 12.5 Hz, 1H), 3.17 (s, 3H), 1.43 (d, J = 7.0 Hz, 3H). |
| 44 | | | RT 1.79 min, MI 363, Method (4LCMS1); $^1$H NMR (400 MHz, DMSO-$d_6$) δ 14.21 (s, 1H), 12.77 (s, 1H), 9.41 (s, 1H), 9.02 (s, 1H), 8.73 (s, 1H), 4.54 (dt, J = 7.0, 3.4 Hz, 1H), 4.04-3.92 (m, 1H), 3.49-3.39 (m, 1H), 3.21 (d, J = 27.1 Hz, 3H), 2.99 (d, J = 10.8 Hz, 1H), 1.39 (d, J = 7.0 Hz, 3H). |
| 45 | | | RT 2.49 min, MI 399/401, Method (2LCMS5) |
| 46 | | | RT 2.02 min, MI 377/378, Method (1LCMS12) |

-continued

| No | [F3-4] | Product [F3-6] | Characterisation |
|---|---|---|---|
| 47 | | | RT 3.23 min, MI 350/351, Method (1LCMS12); ¹H NMR (600 MHz, DMSO-d₆) δ 8.70 (s, 1H), 3.68-3.64 (m, 4H), 3.63-3.58 (m, 4H). |
| 48 | | | RT 1.65 min, MI 309/310, Method (1LCMS12); ¹H NMR (600 MHz, Methanol-d₄) δ 8.03 (s, 1H), 4.02 (dq, J = 10.0, 6.2, 5.8 Hz, 1H), 3.37-3.32 (m, 1H), 3.27-3.20 (m, 1H), 3.02 (dd, J = 12.5, 3.7 Hz, 1H), 2.97-2.87 (m, 2H), 2.67 (dd, J = 12.6, 5.3 Hz, 1H), 2.60 (s, 3H), 1.16 (d, J = 6.5 Hz, 3H). |
| 49 | | ·HCl | RT 1.65 min, MI 310/312, Method (4LCMS1); ¹H NMR (400 MHz, DMSO-d6) δ 12.90 (s, 1H), 9.56 (s, 1H), 9.53-9.43 (m, 1H), 9.12 (s, 1H), 4.60-4.47 (m, 1H), 4.01 (dd, J = 14.6, 3.2 Hz, 1H), 3.49-3.39 (m, 1H), 3.31-3.24 (m, 1H), 3.22-3.12 (m, 2H), 3.12-2.97 (m, 1H), 1.40 (d, J = 7.0 Hz, 3H). |
| 50 | | ·HCl | RT 1.57 min, MI 309, Method (4LCMS1). ¹H NMR (400 MHz, DMSO-d₆) δ 12.85 (s, 1H), 9.36 (s, 1H), 9.00 (s, 1H), 7.57 (s, 1H), 7.19 (s, 1H), 4.54 (d, J = 7.1 Hz, 1H), 4.15 (s, 3H), 4.04-3.93 (m, 1H), 3.45 (ddd, J = 14.6, 11.7, 2.9 Hz, 1H), 3.31-3.24 (m, 1H), 3.19 (d, J = 3.4 Hz, 2H), 3.06 (t, J = 11.8 Hz, 1H), 1.40 (d, J = 7.0 Hz, 3H). |
| 51 | | | RT 2.66 min, MI 296/298, Method (1LCMS12) |

| No | [F3-4] | Product [F3-6] | Characterisation |
|---|---|---|---|
| 52 | 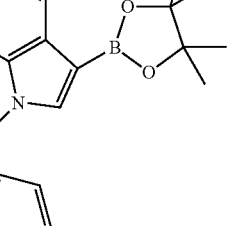 | 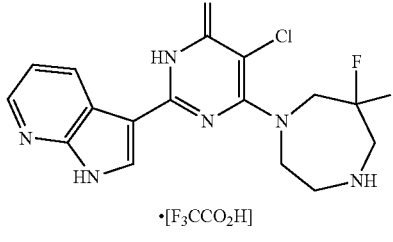 •[F$_3$CCO$_2$H] | RT 1.72 min, MI 381, Method (1LCMS13); $^1$H NMR (600 MHz, DMSO-d$_6$) δ 12.56 (s, 2H), 8.61 (s, 1H), 8.51 (d, J = 7.9 Hz, 1H), 8.36 (d, J = 4.7 Hz, 1H), 7.29 (dd, J = 8.0, 4.7 Hz, 1H), 4.56 (t, J = 13.3 Hz, 2H), 3.99 (s, 2H), 3.63 (t, J = 13.1 Hz, 2H), 3.45 (s, 2H). |
| 53 | 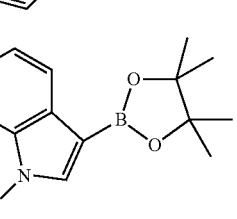 | 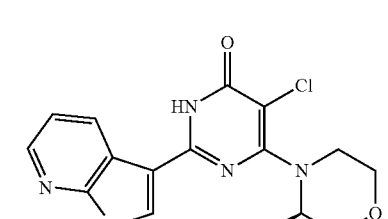 | RT 2.26 min, MI 346, Method (1LCMS13); $^1$H NMR (600 MHz, DMSO-d$_6$) δ 12.49 (br s, 1H), 12.44 (br s, 1H), 8.61 (br d, J = 2.4 Hz, 1H), 8.57 (d, J = 7.4 Hz, 1H), 8.34 (dd, J = 4.5, 1.4 Hz, 1H), 7.27 (dd, J = 7.9, 4.6 Hz, 1H), 4.41-4.40 (m, 1H), 3.95-3.93 (m, 1H), 8.83 (d, J = 13.2 Hz, 1H), 3.71-3.65 (m, 2H), 3.62-3.58 (m, 1H), 3.53-3.48 (m, 1H), 1.32 (d, J = 6.7 Hz, 3H). |
| 54 | 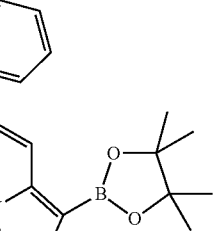 | 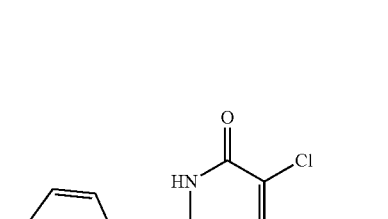 | RT 3.39 min, MI 346.12, Method (1LCMS12); $^1$H NMR (600 MHz, Methanol-d$_4$/CDCl$_3$) δ 8.67 (s, 1H), 8.64 (d, J = 6.7 Hz, 1H), 8.39 (d, J = 9.0 Hz, 1H), 7.54 (t, J = 7.9 Hz, 1H), 7.22 (t, J = 6.9 Hz, 1H), 4.56 (q, J = 6.2 Hz, 1H), 4.04-3.97 (m, 2H), 3.83 (dd, J = 3.0 and 11.3 Hz, 1H), 3.77-3.70 (m, 2H), 3.63 (ddd, J = 3.2, 11.4 and 14.0 Hz, 1H), 1.44 (d, J = 6.8 Hz, 3H). |

Synthesis of tert-butyl (3R)-4-(5,6-dichloro-2-iodo-pyrimidin-4-yl)-3-methyl-piperazine-1-carboxylate (3-012)

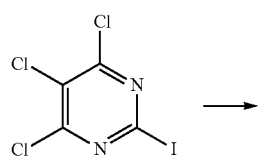

To a stirred solution of 4,5,6-trichloro-2-iodo-pyrimidine (3-002) (18.8 g, 60.8 mmol) and triethylamine (8.9 mL, 63.9 mmol) in chloroform (160 mL) was added (R)-1-boc-3-methylpiperazine (12.2 g, 60.8 mmol). The reaction was stirred at room temperature under nitrogen for 20 h. Water (100 mL) was added and the two phases were separated. The aqueous was extracted with DCM (2×100 mL). The combined organics were dried and concentrated affording a yellow oil. The oil was dissolved into a small amount of warm methanol. The mixture cooled causing a white precipitate to form. The precipitate was collected via vacuum filtration and dried under vacuum affording the title compound (19 g, 66%) as a white powder. LCMS: RT 5.98 min, MI 473, method (4LCMS1); $^1$H NMR (400 MHz, CDCl$_3$) δ 4.61 (s, 1H), 4.25-3.80 (m, 3H), 3.34 (dd, J=13.8, 3.5 Hz, 1H), 3.18-2.89 (m, 2H), 1.48 (s, 9H), 1.32 (d, J=6.7 Hz, 3H).

Synthesis of tert-butyl (3R)-4-(5-chloro-2-iodo-6-oxo-1H-pyrimidin-4-yl)-3-methyl-piperazine-1-carboxylate (3-013)

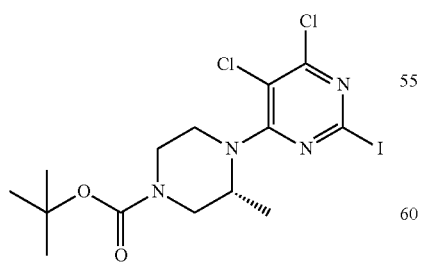

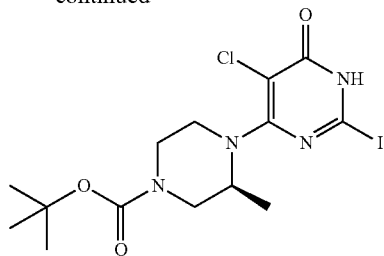

A suspension of tert-butyl (3R)-4-(5,6-dichloro-2-iodo-pyrimidin-4-yl)-3-methyl-piperazine-1-carboxylate (3-012) (0.200 g, 0.423 mmol) in 1,4-dioxane (3 mL) was prepared and NaOH (3.17 mL of a 2M aq solution, 6.34 mmol) was added. The reaction mixture was stirred at room temperature for 1 h, then heated to 100° C. for 1 h. The reaction mixture was cooled to room temperature and neutralised to pH 7 by addition of a saturated aqueous solution of NH$_4$Cl then HCl (1 M aq). The mixture was extracted with CH$_2$Cl$_2$ (2×25 mL) then 9:1 CHCl$_3$:iso-propanol (20 mL). The combined organic extracts were dried over MgSO$_4$, filtered and concentrated by rotary evaporation. The residue was purified by column chromatography on silica gel, eluting with 50-75% EtOAc in cyclohexane. The appropriate fractions were combined and concentrated to give the title compound (0.107 g, 56%). LCMS RT 2.88 min, MI 455, Method (1LCMS13).

Synthesis of tert-butyl (3R)-4-[2-[1-(benzenesulfonyl)pyrrolo[2,3-b]pyridin-3-yl]-5-chloro-6-oxo-1H-pyrimidin-4-yl]-3-methyl-piperazine-1-carboxylate (3-014)

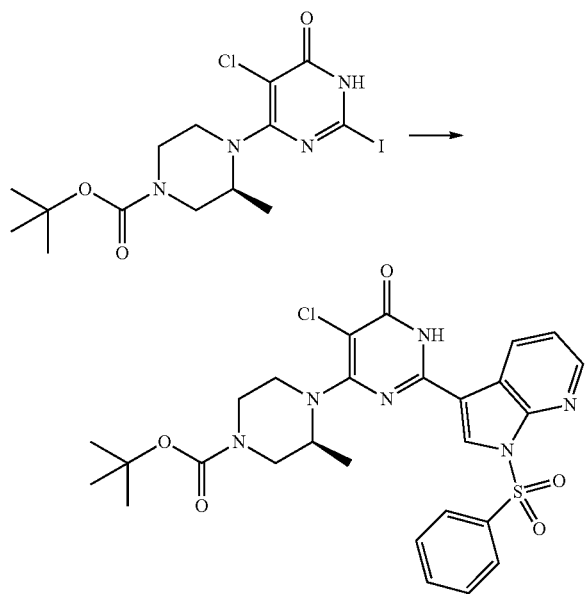

A suspension of tert-butyl (3R)-4-(5-chloro-2-iodo-6-oxo-1H-pyrimidin-4-yl)-3-methyl-piperazine-1-carboxylate (3-013) (0.100 g, 0.220 mmol), 1-(phenylsulfonyl)-7-azaindole-3-boronic acid pinacol ester (0.089 g, 0.231 mmol), cesium carbonate (0.107 g, 0.330 mmol) and tetrakis(triphenylphosphine)palladium (0.013 g, 0.011 mmol) in 1,4-dioxane (1 mL) and water (0.3 mL) was prepared, degassed, and heated to 80° C. for 1 h. The reaction mixture was partitioned between NaHCO$_3$ (sat. aq) and CH$_2$Cl$_2$. The organic phase was separated and the aqueous extracted with CH$_2$Cl$_2$. The combined organic portions were dried over MgSO$_4$, filtered and concentrated by rotary evaporation. The residue was purified by column chromatography on silica gel, eluting with cyclohexane containing 5-50% EtOAc. The appropriate fractions were combined and concentrated to the title compound (0.050 g, 39%) as a colourless solid. LCMS: RT 3.33 min, MI 585, Method (1LCMS13); $^1$H NMR (600 MHz, DMSO-d$_6$) δ 12.82 (s, 1H), 9.15 (s, 1H), 8.60 (d, J=7.9 Hz, 1H), 8.47 (dd, J=4.9, 1.6 Hz, 1H), 8.16-8.15 (m, 2H), 7.78-7.75 (m, 1H), 7.66 (t, J=7.9 Hz, 2H), 7.50 (dd, J=8.0, 4.8 Hz, 1H), 4.47 (br s, 1H), 4.04-3.99 (m, 2H), 3.78 (dt, J=13.2, 2.1 Hz, 1H), 3.35-3.30 (m, 1H), 3.20-2.95 (br m, 2H), 1.41 (s, 9H), 1.21 (d, J=6.7 Hz, 3H).

Synthesis of tert-butyl (3R)-4-[5-chloro-6-oxo-2-(1H-pyrrolo[2,3-b]pyridin-3-yl)-1H-pyrimidin-4-yl]-3-methyl-piperazine-1-carboxylate (3-015)

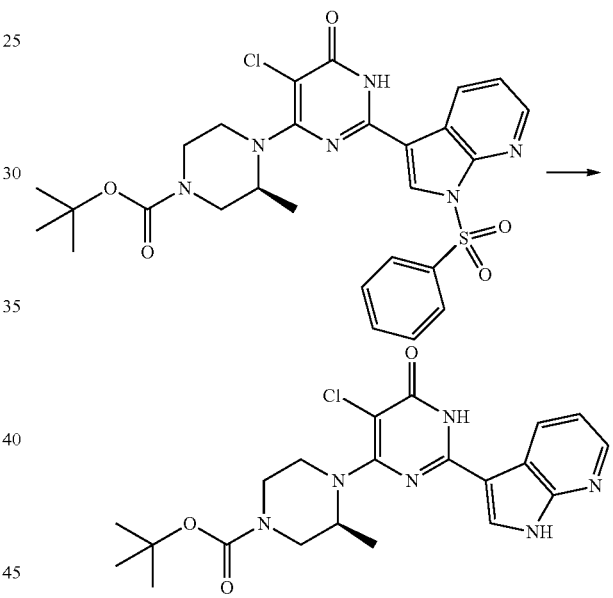

A suspension of tert-butyl (3R)-4-[2-[1-(benzenesulfonyl)pyrrolo[2,3-b]pyridin-3-yl]-5-chloro-6-oxo-1H-pyrimidin-4-yl]-3-methyl-piperazine-1-carboxylate (3-014) (0.050 g, 0.085 mmol) in 1,4-dioxane (1 mL) was prepared and sodium tert-butoxide (0.012 g, 0.128 mmol) was added. The mixture was heated to 80° C. for 1 h then cooled to room temperature, diluted with water and extracted with CHCl$_3$:iso-propanol. The combined organic portions were dried over MgSO$_4$, filtered and concentrated by rotary evaporation. The residue was purified by column chromatography on silica gel, eluting with dichloromethane containing 0-10% MeOH, then 10-20% MeOH. The appropriate fractions were combined and concentrated to give the title compound (0.012 g, 32%). LCMS: RT 2.73 min, MI 445, Method (1LCMS13). $^1$H NMR (600 MHz, DMSO-d$_6$) δ 12.48 (br s, 1H), 12.42 (br s, 1H), 8.61-8.58 (m, 2H), 8.34 (dd, J=4.7, 1.6 Hz, 1H), 7.30 (dd, J=8.0, 4.6 Hz, 1H), 4.50 (br s, 1H), 4.06-3.93 (m, 2H), 3.79 (d, J=13.2 Hz, 1H), 3.37-3.34 (br m, 1H), 3.21-3.00 (m, 2H), 1.43 (s, 9H), 1.24 (d, J=6.9 Hz, 3H).

Synthesis of 5-chloro-4-[(2R)-2-methylpiperazin-1-yl]-2-(1H-pyrrolo[2,3-b]pyridin-3-yl)-1H-pyrimidin-6-one 2,2,2-trifluoroacetic acid (55)

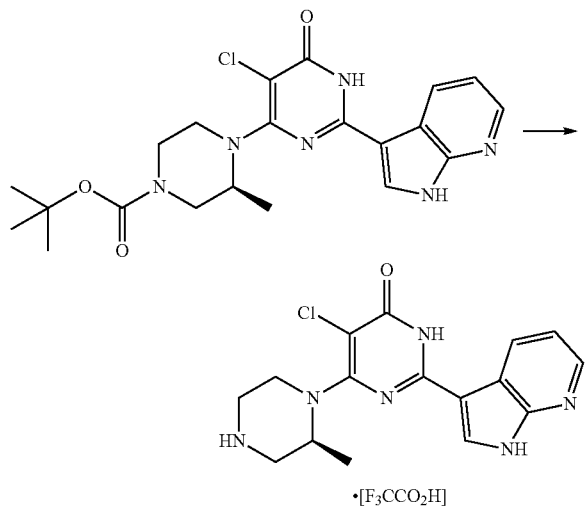

·[F₃CCO₂H]

A solution of tert-butyl (3R)-4-[5-chloro-6-oxo-2-(1H-pyrrolo[2,3-b]pyridin-3-yl)-1H-pyrimidin-4-yl]-3-methyl-piperazine-1-carboxylate (0.027 g, 0.0607 mmol) (3-015) in chloroform (0.500 mL) was prepared and trifluoroacetic acid (0.093 mL, 1.21 mmol) was added. The reaction mixture was stirred at room temperature for 3 h. The reaction mixture was concentrated by rotary evaporation and the residue was triturated in diethyl ether. The resulting yellow solid was filtered and dried under vacuum to give the title compound (0.008 g, 29%). LCMS: RT 1.66 min, MI 345, Method (1LCMS13); $^1$H NMR (500 MHz, DMSO-d$_6$) δ 12.59 (s, 1H), 12.54 (s, 1H), 8.82 (br d, J=141.6 Hz, 2H), 8.64 (d, J=3.1 Hz, 1H), 8.54 (dd, J=8.1, 1.5 Hz, 1H), 8.36 (dd, J=4.7, 1.7 Hz, 1H), 7.27 (dd, J=8.0, 4.7 Hz, 1H), 4.60-4.52 (m, 1H), 4.05-3.98 (m, 1H), 3.54-3.46 (m, 1H), 3.39-3.36 (m, 1H), 3.29-3.13 (m, 3H), 1.39 (d, J=6.9 Hz, 3H).

Synthesis of (3R)-4-[5,6-dichloro-2-(2-methylimidazol-1-yl)pyrimidin-4-yl]-3-methyl-morpholine (3-016)

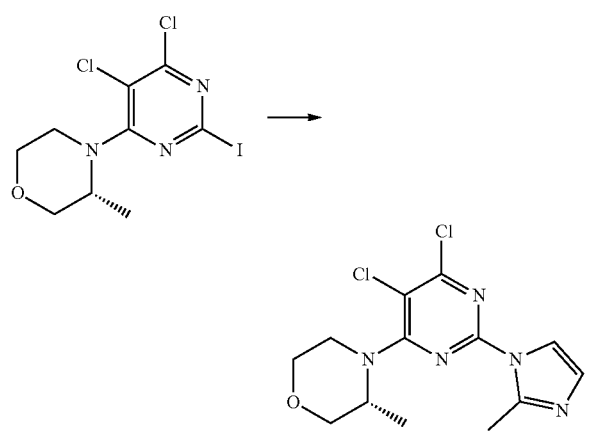

To a thoroughly degassed solution of (3R)-4-(5,6-dichloro-2-iodo-pyrimidin-4-yl)-3-methyl-morpholine (200 mg, 0.535 mmol) (3-009), 2-methylimidazole (43.9 mg, 0.535 mmol), potassium carbonate (81.3 mg, 0.588 mmol) and 8-hydroxyquinoline (3.88 mg, 0.027 mmol) in DMSO (5 mL) was added copper iodide (5.09 mg, 0.027 mmol). The mixture was heated to 110° C. for 2 h. The mixture was then cooled to room temperature and diluted with water (50 mL) causing a blue precipitate to form. The mixture was filtered and the filter cake was washed with ethyl acetate (2×20 mL). The filtrate was separated with the aqueous being further extracted with ethyl acetate (3×20 mL), the combined organics were concentrated to dryness to afford a green oil. The oil was purified using flash chromatography on C18 silica gel eluting with a mixture of acetonitrile in water (5-40% with 0.1% formic acid). The desired fractions were passed through an SCX-2 cartridge and the product was eluted with ammonia in methanol. The basic eluent was concentrated to dryness to afford the title compound (126 mg, 72%) as a yellow green film. LCMS: 2.51 min, MI 328, Method (4LCMS1); $^1$H NMR (400 MHz, CDCl$_3$) δ 7.72 (d, J=1.7 Hz, 1H), 6.93 (d, J=1.7 Hz, 1H), 4.57 (d, J=7.0 Hz, 1H), 4.10 (dt, J=13.5, 1.2 Hz, 1H), 4.01-3.96 (m, 1H), 3.76 (d, J=2.2 Hz, 2H), 3.68 (td, J=11.5, 2.4 Hz, 1H), 3.60-3.51 (m, 1H), 2.77 (s, 3H), 1.46 (d, J=6.8 Hz, 3H).

Synthesis of 5-chloro-2-(2-methylimidazol-1-yl)-4-[(3R)-3-methylmorpholin-4-yl]-1H-pyrimidin-6-one (56)

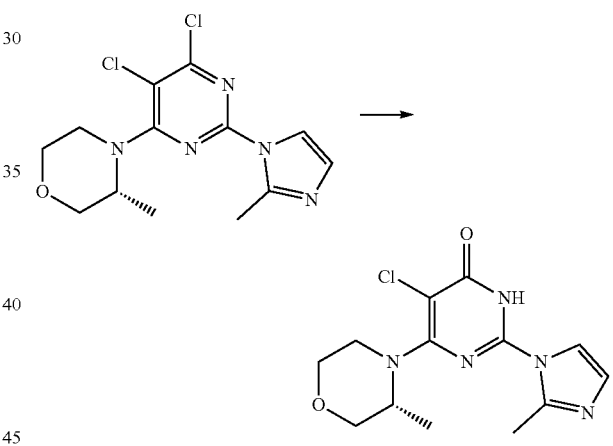

To a vial containing (3R)-4-[5,6-dichloro-2-(2-methylimidazol-1-yl)pyrimidin-4-yl]-3-methyl-morpholine (3-016) (126 mg, 0.384 mmol) in 1,4-dioxane (2 mL) and water (0.5 mL) was added sodium hydroxide (0.18 g, 4.61 mmol). The vial was sealed and irradiated in the microwave to 120° C. for 20 min. 1 M aqueous HCl was added to bring the mixture to pH 7 before being passed through an SCX-2 cartridge. The cartridge was washed with methanol before the compound was eluted with 2.0 M ammonia in methanol. The basic fraction was concentrated to dryness to afford a white film. The film was purified by flash chromatography on C18 silica gel eluting with a mixture of acetonitrile in water (5-100% with 0.1% formic acid). The desired fractions were concentrated to dryness to afford the title compound (5.43 mg, 5%) as a white powder. LCMS: 2.21 min, MI 310, Method (4LCMS1); $^1$H NMR (400 MHz, Methanol-d$_4$) δ 7.89 (d, J=1.9 Hz, 1H), 7.03 (d, J=1.8 Hz, 1H), 4.37-4.30 (m, 1H), 3.89 (dt, J=11.3, 3.0 Hz, 1H), 3.79 (dd, J=11.3, 3.1 Hz, 1H), 3.70 (td, J=10.9, 2.8 Hz, 1H), 3.64 (dd, J=11.2, 2.7 Hz, 2H), 3.55-3.46 (m, 1H), 2.82 (s, 3H), 1.29 (d, J=6.7 Hz, 3H).

General Scheme 4.

In one approach (General Scheme 4), compounds of general formula [F4-3] were prepared by the reaction of a 4,6-dichloro-5-halo-2-iodo-pyrimidine derivative of general formula [F4-1] in a nucleophilic aromatic substitution type reaction utilising a suitable amine of general formula [F4-2], and a base such as Et₃N or N,N-diisopropylethylamine in a polar solvent such as ethanol, 1,4-dioxane, DMA or DMF at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. 5-Halo-(2-heterocyclyl)-3H-pyrimidin-4-one derivatives of general formula [F4-5] were prepared by a metal catalysed C—H activation coupling reaction of compounds of general formula [F4-3] with a suitable heterocycle of general formula [F4-4] utilising a suitable catalyst such as palladium acetate and a base such as cesium carbonate, with or without a suitable ligand such as tri-tert-butylphosphonium tetrafluoroborate, in a polar solvent such as tert-butanol, iso-amylalcohol or DMA at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. In cases where the heterocycle (het) or substituent R' or R" contained an amine protected by a standard amine protecting group such as tert-butyloxycarbonyl (Boc), compounds of formula [F4-5] are prepared by a suitable deprotection reaction, for example reaction with an acid such as TFA or HCl in a suitable solvent such as DCM at ambient temperature. After reaction work up, typically by a liquid-liquid extraction or purification by acidic ion exchange catch-release the crude product was purified by flash column chromatography, reverse phase preparative HPLC or re-crystallisation.

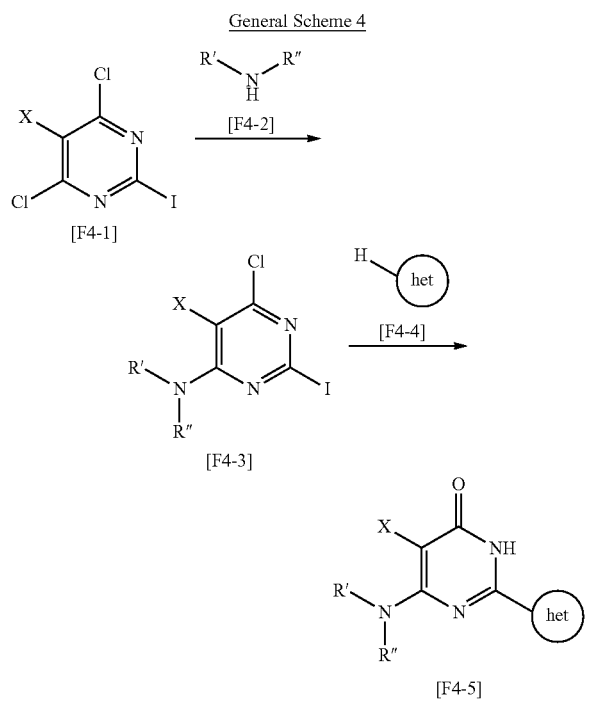

[F4-1]

[F4-3]

[F4-5]

Synthesis of tert-butyl 4-[5-chloro-2-(4-methylthi-azol-5-yl)-6-oxo-1H-pyrimidin-4-yl]-6,6-difluoro-1,4-diazepane-1-carboxylate (4-001)

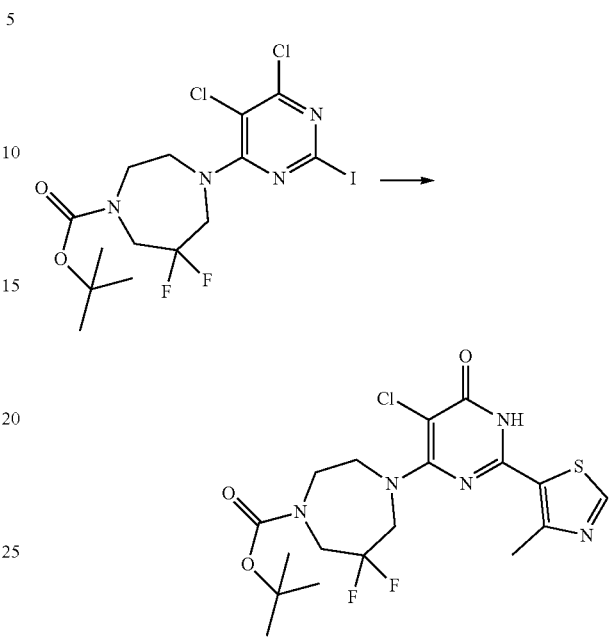

A stirred solution of 4-methylthiazole (0.15 mL, 1.62 mmol), tert-butyl 4-(5,6-dichloro-2-iodo-pyrimidin-4-yl)-6,6-difluoro-1,4-diazepane-1-carboxylate (3-003, prepared in scheme 3) (0.75 g, 1.47 mmol) and cesium carbonate (1.44 g, 4.42 mmol) in DMA (10 mL) was degassed and placed under a nitrogen atmosphere. Palladium acetate (0.03 g, 0.147 mmol) was added and the mixture was heated to 110° C. for 18 h. The reaction mixture was concentrated, affording a black oil. The oil was purified using flash chromatography on silica gel eluting with a mixture of ethyl acetate in DCM (20-100%). The desired fractions were concentrated to dryness affording the title compound (0.254 g, 37%) as a yellow film. LCMS: 4.17 min, MI 462, method (4LCMS1); ¹H NMR (400 MHz, CDCl₃) δ 12.57 (s, 1H), 8.85 (s, 1H), 4.34 (t, J=12.2 Hz, 2H), 3.86 (d, J=12.4 Hz, 6H), 2.80 (s, 3H), 1.49 (s, 9H).

Synthesis of 5-chloro-4-(6,6-difluoro-1,4-diazepan-1-yl)-2-(4-methylthiazol-5-yl)-1H-pyrimidin-6-one hydrochloride (57)

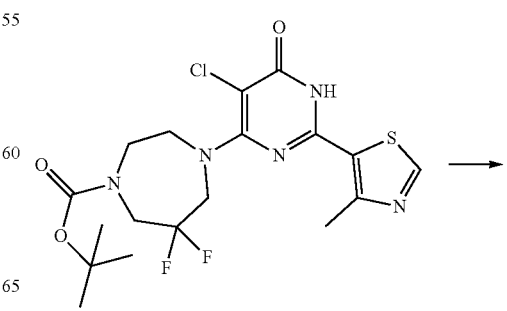

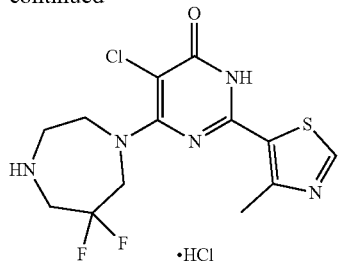

To a stirred solution of tert-butyl 4-[5-chloro-2-(4-methylthiazol-5-yl)-6-oxo-1H-pyrimidin-4-yl]-6,6-difluoro-1,4-diazepane-1-carboxylate (4-001) (0.25 g, 0.55 mmol) in DCM (5 mL) was added HCl (2.75 mL of a 2.0 M solution in diethyl ether, 5.49 mmol) under nitrogen. The reaction was allowed to stir for 18 h. After this time, a yellow precipitate formed in the reaction which was collected via vacuum filtration. The resulting powder was purified using basic preparative LCMS. The desired fractions were concentrated affording a white powder. The powder was dissolved in DCM and 2.0 M hydrogen chloride in diethyl ether was added causing precipitation of a yellow powder. The powder was collected via vacuum filtration to give the title compound (160 mg, 73%) as a yellow powder. LCMS: 1.93 min, MI 362, Method (2LCMS1); $^1$H NMR (400 MHz, Methanol-$d_4$) δ 9.50 (s, 1H), 4.56 (t, J=13.5 Hz, 2H), 4.17 (t, J=5.4 Hz, 2H), 3.89 (t, J=11.9 Hz, 2H), 3.68 (t, J=5.4 Hz, 2H), 2.87 (s, 3H).

The following compounds were synthesised according to the general synthesis shown in scheme [4]:

| Number | Product [F4-5] | Characterisation |
|---|---|---|
| 58 | | RT 1.64 min, MI 326, Method (4LCMS1); $^1$H NMR (400 MHz, Methanol-$d_4$) δ 9.70 (s, 1H), 4.80-4.66 (m, 1H), 4.17 (dt, J = 14.9, 2.9 Hz, 1H), 3.63 (td, J = 14.8, 3.0 Hz, 1H), 3.47-3.23 (m, 4H), 2.92 (s, 3H), 1.48 (d, J = 7.0 Hz, 3H). |
| 59 | | RT 3.17 min, MI 327; Method (4LCMS1); $^1$H NMR (400 MHz, Methanol-$d_4$) δ 8.98 (s, 1H), 4.51-4.45 (m, 1H), 4.04-3.84 (m, 2H), 3.81-3.49 (m, 4H), 2.75 (s, 3H), 1.39 (d, J = 6.8 Hz, 3H). |
| 60 | | RT 1.89 min, MI 380, Method (2LCMS1); $^1$H NMR (400 MHz, Methanol-$d_4$) δ 9.18 (s, 1H), 5.62-5.43 (m, 1H), 4.28 (d, J = 15.0 Hz, 1H), 3.89 (d, J = 14.3 Hz, 1H), 3.78 (t, J = 13.9 Hz, 1H), 3.64 (dd, J = 14.3, 6.0 Hz, 1H), 3.55-3.42 (m, 1H), 3.39-3.20 (m, 1H), 2.80 (s, 3H). |
| 61 | | RT 1.71 min, MI 362, Method (2LCMS1); $^1$H NMR (400 MHz, Methanol-$d_4$) δ 9.37 (s, 1H), 6.48 (td, J = 53.7, 2.2 Hz, 1H), 4.36 (d, J = 15.1 Hz, 1H), 3.80 (d, J = 13.9 Hz, 1H), 3.72 (t, J = 13.9 Hz, 1H), 3.54-3.42 (m, 3H), 3.41-3.31 (m, 1H), 2.84 (s, 3H). |

-continued

| Number | Product [F4-5] | Characterisation |
|---|---|---|
| 62 | 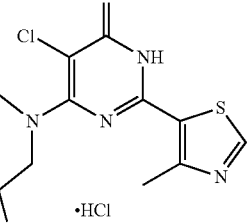 | RT 1.74 min, MI 344, Method (2LCMS1); $^1$H NMR (400 MHz, Methanol-$d_4$) δ 9.12 (s, 1H), 5.35 (dd, J = 44.3, 4.6 Hz, 1H), 4.63-4.42 (m, 1H), 4.32-3.95 (m, 3H), 3.85-3.76 (m, 1H), 3.74-3.65 (m, 1H), 3.64-3.50 (m, 1H), 3.30-3.23 (m, 1H), 2.77 (s, 3H). |
| 63 | 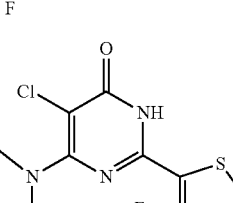 | RT 2.03 min, MI 416, Method (4LCMS1); $^1$H NMR (400 MHz, DMSO-$d_6$) δ 9.39 (s, 1H), 4.61 (t, J = 13.3 Hz, 2H), 4.10 (t, J = 5.2 Hz, 2H), 3.85 (t, J = 12.8 Hz, 2H), 3.54 (t, J = 5.3 Hz, 2H). |
| 64 | 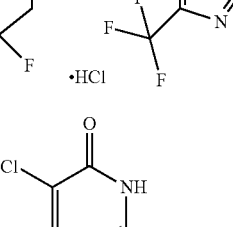 | RT 3.45 min, MI 347, Method (4LCMS1); $^1$H NMR (400 MHz, DMSO-$d_6$) δ 12.65 (s, 1H), 9.21 (s, 1H), 4.42 (d, J = 7.3 Hz, 1H), 4.01-3.78 (m, 2H), 3.64 (d, J = 2.4 Hz, 2H), 3.55 (td, J = 11.4, 2.6 Hz, 1H), 3.50-3.36 (m, 1H), 1.32 (d, J = 6.8 Hz, 3H). |

General Scheme 5.

In one approach (General Scheme 5), compounds of general formula [F5-3] were prepared by a metal catalysed C—H activation coupling reaction of 6-chloro-5-halo-2-iodo-pyrimidine derivatives of general formula [F5-1] with a suitable heterocycle of general formula [F5-2] utilising a suitable catalyst such as palladium acetate and a base such as cesium carbonate, with or without a suitable ligand such as tri-tert-butylphosphonium tetrafluoroborate, in a polar solvent such as tert-butanol, iso-amylalcohol or DMA at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. 6-Allyloxy-5-halo-2-heterocyclyl-pyrimidine derivatives of general formula [F5-4] were prepared by a nucleophilic aromatic substitution type reaction of compounds of general formula [F5-3] utilising allyl alcohol, and a suitable base such as sodium hydride in a polar solvent such as THF at low temperature or room temperature. After reaction work up, typically by a liquid-liquid extraction, the crude product was purified by flash column chromatography, reverse phase preparative HPLC or re-crystallisation. 5-Halo-(2-heterocyclyl)-3H-pyrimidin-4-one derivatives of general formula [F5-5] were prepared by a metal catalysed deprotection reaction of compounds of general formula [F5-4] utilising a suitable catalyst such as [1,1'-bis(diphenylphosphino)ferrocene]dichloropalladium(II) and a suitable base such as morpholine, in a suitable solvent such as dichloromethane at ambient temperature. After reaction work up, typically by a liquid-liquid extraction, the crude product could be purified by flash column chromatography, reverse phase preparative HPLC or re-crystallisation. In cases where the heterocycle (het) or substituent R' or R" contained an amine protected by a standard amine protecting group such as tert-butyloxycarbonyl (Boc), compounds of formula [F5-5] are prepared by a suitable deprotection reaction, for example reaction with an acid such as TFA or HCl in a suitable solvent such as DCM at ambient temperature. After reaction work up, typically by a liquid-liquid extraction or purification by acidic ion exchange catch-release, the crude product was purified by flash column chromatography, reverse phase preparative HPLC or re-crystallisation.

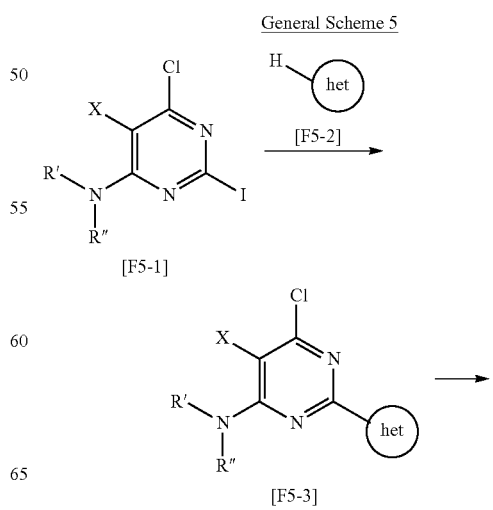

General Scheme 5

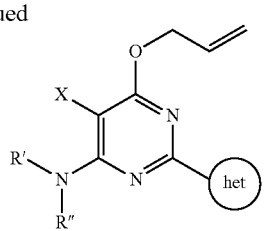

[F5-4]

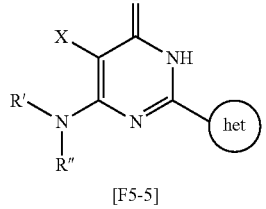

[F5-5]

Synthesis of tert-butyl (3R)-4-[5,6-dichloro-2-(4-chlorothiazol-5-yl)pyrimidin-4-yl]-3-methyl-piperazine-1-carboxylate (5-001)

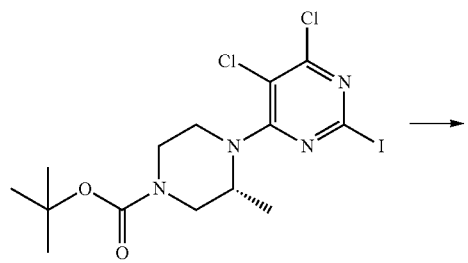

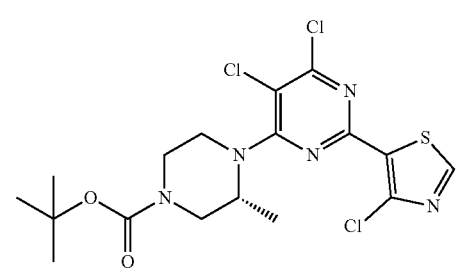

To a thoroughly degassed stirred solution of tert-butyl (3R)-4-(5,6-dichloro-2-iodo-pyrimidin-4-yl)-3-methyl-piperazine-1-carboxylate (3-012, prepared in Scheme 3) (19.0 g, 40.2 mmol), 4-chlorothiazole (4.8 g, 40.2 mmol) and cesium carbonate (19.6 g, 60.2 mmol) in tert-butanol (200 mL) was added tri-tert-butylphosphonium tetrafluoroborate (1.16 g, 4.01 mmol) and palladium acetate (0.45 g, 2.014 mmol). The reaction was heated to 80° C. for 72 h. The reaction mixture was cooled to room temperature, filtered and the filtrate concentrated to dryness to afford a brown oil. This was purified by flash column chromatography on silica gel (eluting with a mixture of ethyl acetate in cyclohexane 0-60%) to give the title compound (3.80 g, 20%) as a yellow powder. LCMS: RT 3.34 min, MI 466, Method (4LCMS6); $^1$H NMR (400 MHz, CDCl$_3$) δ 8.75 (s, 1H), 4.70 (s, 1H), 4.32-3.84 (m, 4H), 3.41 (td, J=13.9, 13.0, 3.3 Hz, 1H), 3.17 (s, 1H), 1.49 (s, 9H), 1.37 (d, J=6.7 Hz, 3H).

Synthesis of tert-butyl (3R)-4-[6-allyloxy-5-chloro-2-(4-chlorothiazol-5-yl)pyrimidin-4-yl]-3-methyl-piperazine-1-carboxylate (5-002)

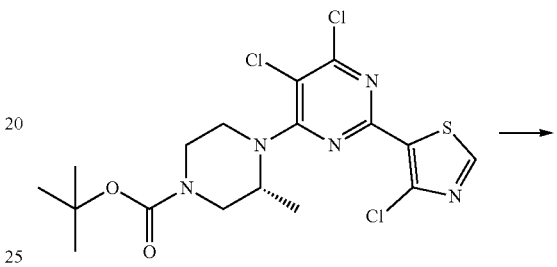

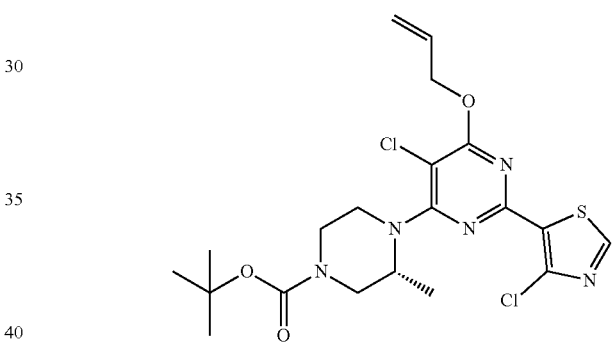

To a stirred solution of allyl alcohol (2.78 mL, 40.9 mmol) in THF (10 mL) at 0° C. under nitrogen was added sodium hydride (60% in mineral oil, 1.63 g, 40.9 mmol) in portions. The mixture was stirred for 10 min. The allyl alcohol mixture was added drop wise to a solution of tert-butyl (3R)-4-[5,6-dichloro-2-(4-chlorothiazol-5-yl)pyrimidin-4-yl]-3-methyl-piperazine-1-carboxylate (5-001) (3.8 g, 8.17 mmol) in THF (20 mL) at 0° C. under nitrogen. Once the addition was complete the reaction was stirred for a further 10 min. Water (100 mL) was added and the mixture was extracted with ethyl acetate (3×150 mL). The combined organics were dried (MgSO$_4$) and concentrated to dryness to afford a yellow film. The film was purified using flash chromatography on silica gel eluting with a mixture of ethyl acetate in cyclohexane (0-30%). The desired fractions were concentrated to dryness to give the title compound (3.5 g, 88%) as a yellow film. $^1$H NMR (400 MHz, CDCl$_3$) δ 8.71 (s, 1H), 6.11 (ddt, J=17.3, 10.5, 5.6 Hz, 1H), 5.47 (dq, J=17.2, 1.5 Hz, 1H), 5.33-5.27 (m, 1H), 5.00 (dt, J=5.6, 1.4 Hz, 2H), 4.58 (s, 1H), 4.21-3.79 (m, 3H), 3.37 (td, J=13.6, 3.3 Hz, 1H), 3.23-2.9 (m, 2H), 1.49 (s, 9H), 1.32 (d, J=6.7 Hz, 3H).

Synthesis of tert-butyl (3R)-4-[5-chloro-2-(4-chloro-thiazol-5-yl)-6-oxo-1H-pyrimidin-4-yl]-3-methyl-piperazine-1-carboxylate (5-003)

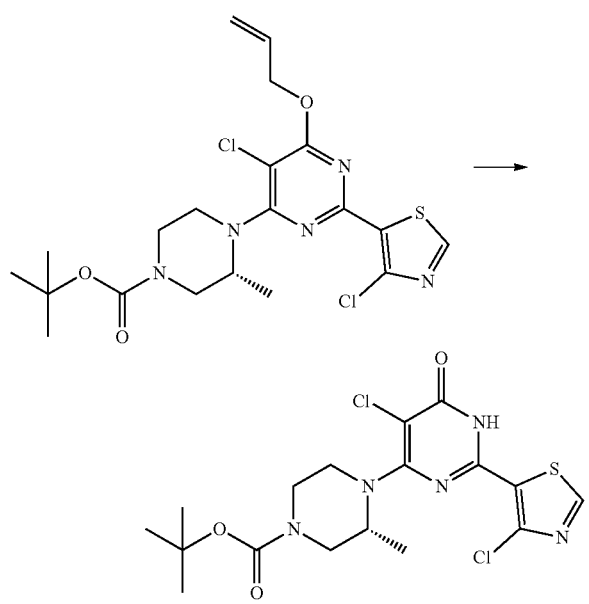

To a degassed stirred solution of tert-butyl (3R)-4-[6-allyloxy-5-chloro-2-(4-chlorothiazol-5-yl)pyrimidin-4-yl]-3-methyl-piperazine-1-carboxylate (5-002) (3.81 g, 7.84 mmol) and morpholine (2.06 mL, 23.5 mmol) in DCM (80 mL) under nitrogen was added [1,1'-bis(diphenylphosphino)ferrocene]dichloropalladium(II), complex with dichloromethane (0.32 g, 0.392 mmol). The mixture was stirred for 18 h. Water (20 mL) was added and the two phases were separated. The aqueous was further extracted with DCM (2×20 mL) before the combined organics were passed through a phase separator and concentrated to dryness to afford a yellow film. The film was sonicated in diethyl ether and left to sit for 90 min. A cream precipitate formed. The precipitate was collected via vacuum filtration affording the title compound (1.74 g, 49%) as a tan powder. LCMS: RT 4.49 min, MI 446, Method (4LCMS1); $^1$H NMR (400 MHz, CDCl$_3$) δ 8.86 (s, 1H), 4.55 (s, 1H), 4.29-3.76 (m, 3H), 3.36 (td, J=13.6, 3.4 Hz, 1H), 3.13 (s, 2H), 1.49 (s, 9H), 1.34 (d, J=6.7 Hz, 3H).

Synthesis of 5-chloro-2-(4-chlorothiazol-5-yl)-4-[(2R)-2-methylpiperazin-1-yl]-1H-pyrimidin-6-one hydrochloride (65)

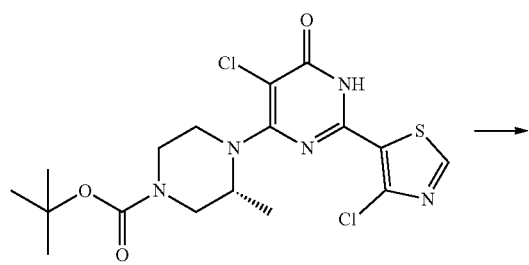

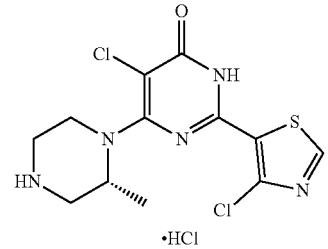
•HCl

To a stirred solution of tert-butyl (3R)-4-[5-chloro-2-(4-chlorothiazol-5-yl)-6-oxo-1H-pyrimidin-4-yl]-3-methyl-piperazine-1-carboxylate (5-003) (1.74 g, 3.91 mmol) in DCM (20 mL) was added hydrogen chloride (19.53 mL of a 4.0 M solution in 1,4-dioxane, 78.1 mmol). The mixture was stirred for 2 h. Ether (100 mL) was added and the resulting precipitate was collected via vacuum filtration affording a white powder. The powder was dissolved in methanol (10 mL) and 2.0 M HCl in diethyl ether (10 mL) was added causing a pale yellow precipitate to form. The precipitate was collected via vacuum filtration affording a yellow powder. The yellow powder was dried in vacuo to give the title compound (0.843 g, 56%). LCMS: RT 1.65 min, MI 346, Method (5LCMS1); $^1$H NMR (400 MHz, DMSO-d$_6$) δ 12.87 (s, 1H), 9.48 (s, 1H), 9.23 (s, 1H), 9.11 (s, 1H), 4.64-4.49 (m, 1H), 4.11 (d, J=14.6 Hz, 1H), 3.47 (dd, J=14.8, 2.9 Hz, 1H), 3.28 (d, J=12.5 Hz, 1H), 3.19 (s, 2H), 3.11 (s, 1H), 1.44 (d, J=7.1 Hz, 3H).

Synthesis of tert-butyl 4-[5,6-dichloro-2-(4-chloro-thiazol-5-yl)pyrimidin-4-yl]-6,6-difluoro-1,4-diaz-epane-1-carboxylate (5-004)

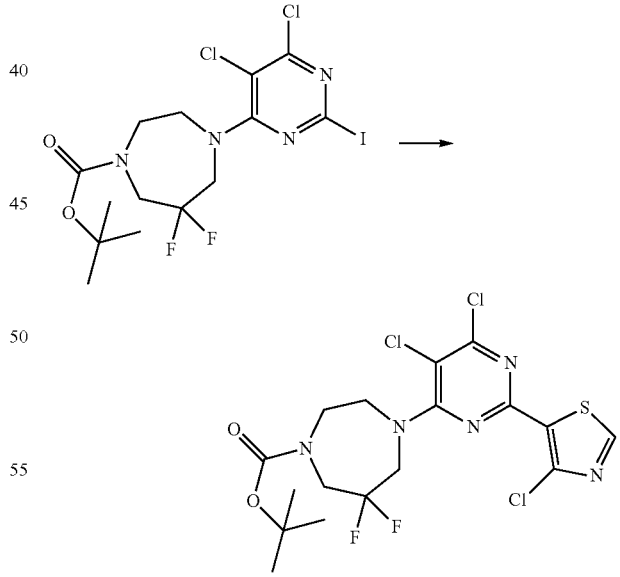

To a thoroughly degassed solution of tert-butyl 4-(5,6-dichloro-2-iodo-pyrimidin-4-yl)-6,6-difluoro-1,4-diaz-epane-1-carboxylate (3-003, prepared in scheme 3) (1.6 g, 3.14 mmol), 4-chlorothiazole (0.38 g, 3.14 mmol) and cesium carbonate (1.54 g, 4.71 mmol) in isoamyl alcohol (16 mL) was added palladium acetate (0.04 g, 0.157 mmol) and tri-tert-butylphosphonium tetrafluoroborate (0.09 g, 0.314 mmol). The mixture was heated to 90° C. for 18 h. The reaction mixture was cooled before being diluted with ethyl acetate and 2 M HCl, and the two phases were separated. The aqueous was further extracted with ethyl acetate, the combined organics were dried (MgSO$_4$) and concentrated to dryness affording a dark brown film. The film was purified using flash chromatography on silica gel eluting with a mixture of ethyl acetate in cyclohexanes (0-50%). The desired fractions were concentrated to dryness to give the title compound (282 mg, 18%) as a brown film. LCMS: RT 5.82 min, MI 502, Method (4LCMS1); $^1$H NMR (400 MHz, CDCl$_3$) δ 8.78 (s, 1H), 4.49 (t, J=12.1 Hz, 2H), 3.94 (s, 4H), 3.86-3.77 (m, 2H), 1.49 (s, 9H).

Synthesis of tert-butyl 4-[6-allyloxy-5-chloro-2-(4-chlorothiazol-5-yl)pyrimidin-4-yl]-6,6-difluoro-1,4-diazepane-1-carboxylate (5-005)

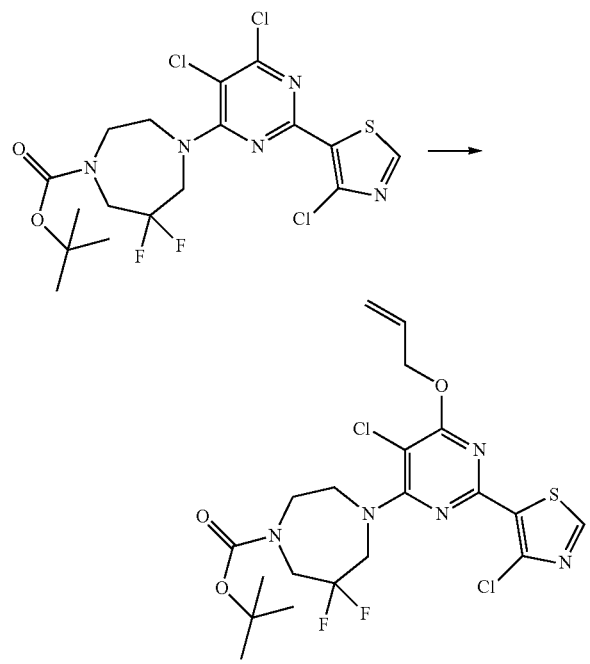

To a stirred solution of allyl alcohol (0.18 mL, 2.62 mmol) in THF (4 mL) at 0° C. under nitrogen was added sodium hydride (60% in mineral oil, 80 mg, 3.14 mmol) in portions. The mixture was stirred for 2 min. tert-Butyl 4-[5,6-dichloro-2-(4-chlorothiazol-5-yl)pyrimidin-4-yl]-6,6-difluoro-1,4-diazepane-1-carboxylate (5-004) (328 mg, 0.524 mmol) in THF (6 mL) was added to the allyl alcohol solution. The mixture was stirred for 5 min. Water (20 mL) was added dropwise. The mixture was extracted with ethyl acetate (3×40 mL), the combined organics were dried (MgSO$_4$) and concentrated to dryness to afford a brown film. The residue was purified by flash chromatography on silica gel eluting with a mixture of ethyl acetate in cyclohexane (0-30%) to afford the title compound (214 mg, 78%) as a yellow film. LCMS: RT 6.15 min, MI 522, Method (5LCMS1); $^1$H NMR (400 MHz, CDCl$_3$) δ 8.72 (s, 1H), 6.11 (ddt, J=17.2, 10.5, 5.6 Hz, 1H), 5.48 (dq, J=17.2, 1.6 Hz, 1H), 5.32 (dq, J=10.4, 1.3 Hz, 1H), 5.00 (dt, J=5.6, 1.4 Hz, 2H), 4.41 (t, J=12.4 Hz, 2H), 3.96-3.76 (m, 6H), 1.49 (s, 9H).

Synthesis of tert-butyl 4-[5-chloro-2-(4-chlorothiazol-5-yl)-6-oxo-1H-pyrimidin-4-yl]-6,6-difluoro-1,4-diazepane-1-carboxylate (5-006)

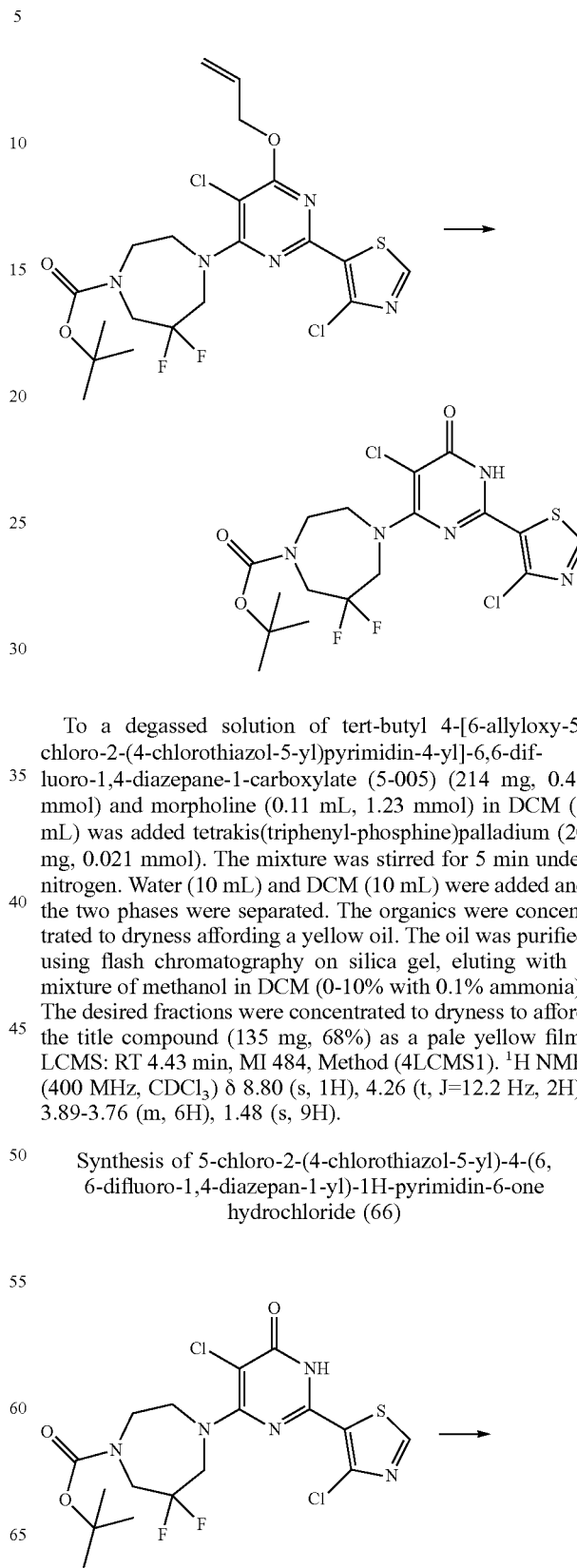

To a degassed solution of tert-butyl 4-[6-allyloxy-5-chloro-2-(4-chlorothiazol-5-yl)pyrimidin-4-yl]-6,6-difluoro-1,4-diazepane-1-carboxylate (5-005) (214 mg, 0.41 mmol) and morpholine (0.11 mL, 1.23 mmol) in DCM (6 mL) was added tetrakis(triphenyl-phosphine)palladium (20 mg, 0.021 mmol). The mixture was stirred for 5 min under nitrogen. Water (10 mL) and DCM (10 mL) were added and the two phases were separated. The organics were concentrated to dryness affording a yellow oil. The oil was purified using flash chromatography on silica gel, eluting with a mixture of methanol in DCM (0-10% with 0.1% ammonia). The desired fractions were concentrated to dryness to afford the title compound (135 mg, 68%) as a pale yellow film. LCMS: RT 4.43 min, MI 484, Method (4LCMS1). $^1$H NMR (400 MHz, CDCl$_3$) δ 8.80 (s, 1H), 4.26 (t, J=12.2 Hz, 2H), 3.89-3.76 (m, 6H), 1.48 (s, 9H).

Synthesis of 5-chloro-2-(4-chlorothiazol-5-yl)-4-(6,6-difluoro-1,4-diazepan-1-yl)-1H-pyrimidin-6-one hydrochloride (66)

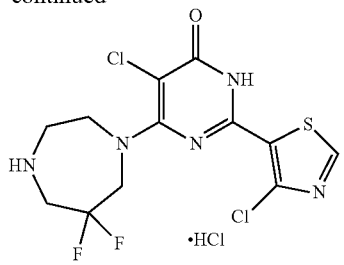

To a stirred solution of tert-butyl 4-[5-chloro-2-(4-chlorothiazol-5-yl)-6-oxo-1H-pyrimidin-4-yl]-6,6-difluoro-1,4-diazepane-1-carboxylate (5-006) (199 mg, 0.413 mmol) in DCM (2 mL) was added hydrogen chloride (4.63 mL of a 4 M solution in 1,4-dioxane, 18.5 mmol). The mixture was stirred for 1 h before concentrating to dryness to afford a yellow powder. The powder was loaded onto a SCX-2 cartridge, washed with methanol and eluted with 2 M ammonia in methanol. The basic fractions were concentrated to dryness to afford a yellow powder. The powder was taken into methanol and hydrogen chloride (1 mL of a 4 M solution in 1,4-dioxane) was added. The mixture was concentrated to afford the title compound (103 mg, 60%) as a light yellow powder. LCMS: RT 1.81 min, MI 382, Method (5LCMS1); $^1$H NMR (400 MHz, DMSO-$d_6$) δ 9.24 (s, 1H), 4.59 (t, J=13.2 Hz, 2H), 4.05 (s, 2H), 3.76 (t, J=13.3 Hz, 2H), 3.52-3.49 (m, 2H).

The following compounds were synthesised according to the general synthesis shown in scheme [5]:

condensation reaction utilising a suitably substituted heterocyclic carboximidamide derivative of general formula [F6-2] in a polar solvent such as methanol or THF in the presence of a base such as sodium methoxide, potassium tert-butoxide or DBU. The reaction is suitably conducted at ambient temperature or at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. Derivatives of general formula [F6-4] were prepared by the reaction of a 5-halo-2-heterocyclyl-1H-pyrimidine-4,6-dione derivative of general formula [F6-3] with a halogenating agent such as phosphorous oxychloride at high temperature. After reaction work up, typically by the addition of water followed by the addition of a base such as aqueous sodium hydroxide, the crude reaction mixture was purified by liquid-liquid extraction, and the reaction product was used crude in the next step or purified by flash column chromatography, reverse phase preparative HPLC or re-crystallisation. Compounds of general formula [F6-6] were prepared by reaction of 4,6-dichloro-5-halo-2-heterocyclyl-pyrimidine derivatives of general formula [F6-4] in a nucleophilic aromatic substitution type reaction utilising a suitable amine of general formula [F6-5], and a base such as Et$_3$N or NaH, or a mineral acid such as HCl, in a polar solvent such as ethanol, butanol, dioxane, DMA or DMF at high temperature either by heating thermally or using a microwave reactor. After reaction work up, typically by a liquid-liquid extraction, the reaction product was used crude in the next step or purified by flash column chromatography, reverse phase preparative HPLC or re-crystallisation. 6-Allyloxy-5-halo-2-heterocyclyl-pyrimidine derivatives of general formula [F6-7] were prepared by a nucleophilic aromatic substitution type reaction of compounds of general formula [F6-6] utilising allyl alcohol, and a suitable base such as sodium hydride in a polar solvent such as THF at low temperature or room temperature. After reaction work up,

| Number | Product [F5-5] | Characterisation |
|---|---|---|
| 67 | (structure) | RT 1.94 min, MI 382, Method (2LCMS1); $^1$H NMR (400 MHz, Methanol-$d_4$) δ 9.08 (s, 1H), 6.51 (t, J = 54.8 Hz, 1H), 4.42 (d, J = 15.2 Hz, 1H), 3.80 (d, J = 13.9 Hz, 1H), 3.76-3.64 (m, 3H), 3.59-3.56 (m, 1H), 3.52-3.44 (m, 1H). |
| 68 | (structure) | RT 1.84 min, MI 400, Method (5LCMS1); $^1$H NMR (400 MHz, Methanol-$d_4$) δ 9.08 (s, 1H), 5.71-5.49 (m, 1H), 4.33 (d, J = 15.1 Hz, 1H), 3.88 (d, J = 14.2 Hz, 1H), 3.77 (t, J = 13.5 Hz, 1H), 3.64 (dd, J = 14.3, 5.9 Hz, 1H), 3.44 (d, J = 12.8 Hz, 1H), 3.28-3.26 (m, 1H). |

General Scheme 6

In one approach (General Scheme 6), compounds of general formula [F6-3] were prepared by the reaction of an α-halo-malonate derivative of general formula [F6-1] in a typically by a liquid-liquid extraction, the crude product was purified by flash column chromatography, reverse phase preparative HPLC or re-crystallisation. 5-Halo-(2-heterocyclyl)-3H-pyrimidin-4-one derivatives of general formula [F6-8] were prepared by a metal catalysed deprotection reaction of compounds of general formula [F6-7] utilising a suitable catalyst such as [1,1'-bis(diphenylphosphino)ferrocene] dichloropalladium(II) and a suitable base such as morpholine, in a suitable solvent such as dichloromethane at ambient temperature. After reaction work up, typically by a liquid-liquid extraction, the crude product could be purified by flash column chromatography, reverse phase preparative HPLC or re-crystallisation. In cases where the heterocycle (het) or substituent R' or R" contained an amine protected by a standard amine protecting group such as tert-butyloxycarbonyl (Boc), compounds of formula [F6-8] are prepared by a suitable deprotection reaction, for example reaction with an acid such as TFA or HCl in a suitable solvent such as DCM at ambient temperature. After reaction work up, typically by a liquid-liquid extraction or purification by acidic ion exchange catch-release the crude product was purified by flash column chromatography, reverse phase preparative HPLC or re-crystallisation.

was added (150 mL) and the residue triturated to form an off-white solid. This was removed by filtration and washed with further EtOAc (100 mL). The filtrate was concentrated under reduced pressure to afford a brown oil which was purified by flash chromatography on silica gel, eluting with 0-20% EtOAc/cyclohexane to afford the title compound (5.57 g, 69%) as a white solid. LCMS: RT 3.18 min, MI 145, Method (4LCMS1); $^1$H NMR (400 MHz, DMSO-$d_6$) δ 9.45 (s, 1H).

Synthesis of
4-chloro-N-hydroxy-thiazole-5-carboxamidine
(6-002)

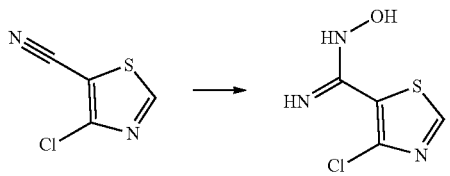

A solution of 4-chlorothiazole-5-carbonitrile (6-001) (5.60 g, 38.73 mmol) in ethanol (129 mL) was prepared and hydroxylamine 50% w/w in water (4.74 mL, 77.47 mmol)

General Scheme 6

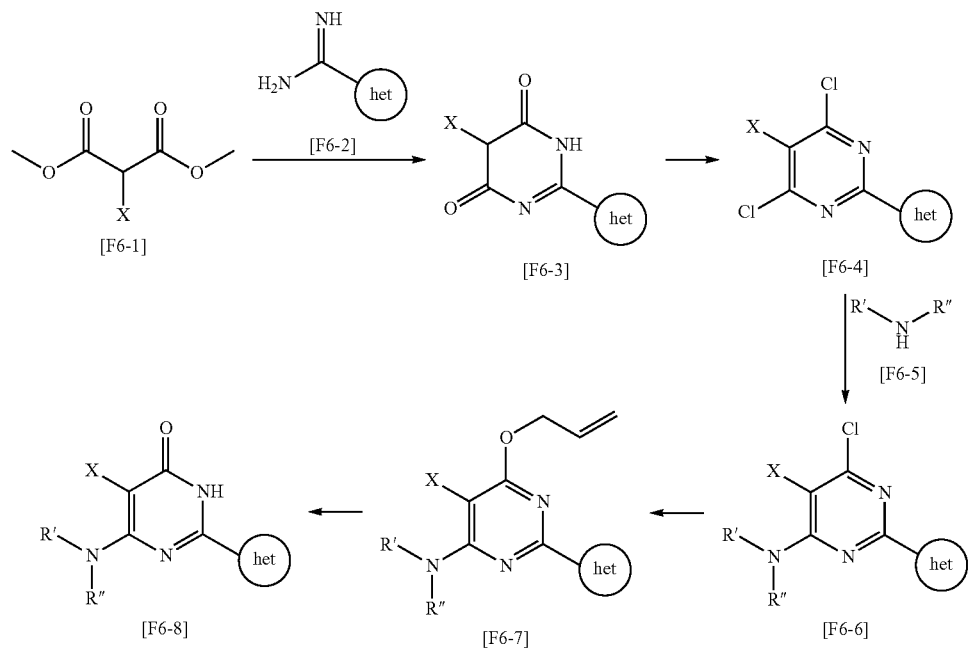

Synthesis of 4-chlorothiazole-5-carbonitrile (6-001)

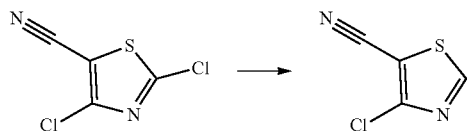 [SMILES: N#Cc1sc(Cl)nc1Cl ; N#Cc1scnc1Cl]

2,4-Dichloro-thiazole-5-carbonitrile (10.0 g, 55.86 mmol) was dissolved in acetic acid (100 mL) then treated with zinc powder (10.96 g, 167.57 mmol) and allowed to stir for 2 days under nitrogen at room temperature. A further 4 g of zinc was added followed by acetic acid (10 mL) and this was left to stir overnight. A further 2 g of zinc, followed by acetic acid (10 mL) was added and the mixture allowed to stir at room temperature for 48 h. The mixture was then filtered through celite, washing with methanol (300 mL) and the filtrate concentrated under reduced pressure. Ethyl acetate was added. The reaction was heated to 80° C. for 2 hours. The reaction mixture was concentrated by rotary evaporation to give the title compound (6.50 g, 94%) as a yellow solid which used without further purification. LCMS: RT 1.43 min, MI 178, Method (4LCMS1); $^1$H NMR (400 MHz, DMSO-$d_6$) δ 10.08 (s, 1H), 9.07 (s, 1H), 5.97 (s, 2H).

Synthesis of 4-chlorothiazole-5-carboxamidine
hydrochloride (6-003)

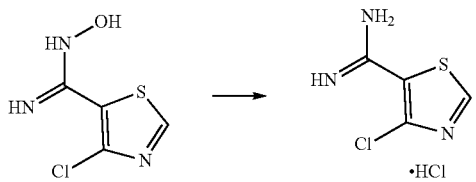 [SMILES: N=C(NO)c1scnc1Cl ; N=C(N)c1scnc1Cl ; Cl]

A solution of 4-chloro-N-hydroxy-thiazole-5-carboxamidine (6-002) (3.16 g, 17.76 mmol) in acetic acid (59 mL) was prepared. Acetic anhydride (2.52 mL, 26.64 mmol) was added and the reaction mixture stirred at room temperature for 1 hour. The mixture was evacuated and back-filled with nitrogen 3 times before the addition of 10% Pd/C (0.95 g, 8.882 mmol). The mixture was then purged with hydrogen (×3) and allowed to stir under a balloon of hydrogen at room temperature overnight. Further 10% Pd/C (0.95 g, 8.882 mmol) was added and the mixture allowed to stir under hydrogen at room temperature overnight. Further 10% Pd/C (0.95 g, 8.882 mmol) was added and the mixture allowed to stir under hydrogen at room temperature overnight. The reaction mixture was filtered through celite, washing with methanol (500 mL) and the filtrate concentrated. The residue was dissolved in 1,4-dioxane (10 mL) before the dropwise addition of 4 M hydrogen chloride solution in 1,4-dioxane (17.8 mL, 71.1 mmol). The mixture was allowed to stir at room temperature for 5 min before the addition of diethyl ether (30 mL). The resulting tan solid was collected by filtration, washed with further diethyl ether (20 mL) and air dried to afford the title compound (1.80 g, 43%). $^1$H NMR (400 MHz, DMSO-$d_6$) δ 9.86-9.69 (d, J=6.4 Hz, 4H), 9.44 (s, 1H).

Synthesis of 5-chloro-2-(4-chlorothiazol-5-yl)-1H-pyrimidine-4,6-dione (6-004)

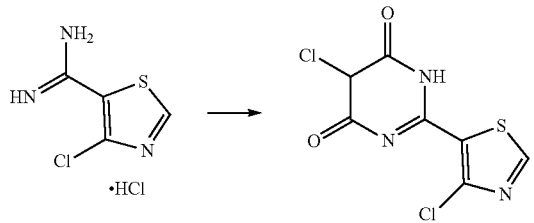 [SMILES: N=C(N)c1scnc1Cl ; Cl ; O=C1N=C(c2scnc2Cl)NC(=O)C1Cl]

To a stirred solution of 4-chlorothiazole-5-carboxamidine hydrochloride (6-003) (1.77 g, 7.53 mmol) and dimethyl chloromalonate (1.84 mL, 7.53 mmol) in methanol (50 mL) was added 1,8-diazabicyclo[5.4.0]undec-7-ene (2.36 mL, 15.8 mmol) dropwise. The mixture was stirred for 10 min at room temperature before being heated to reflux for 2 h. The reaction was cooled to room temperature and concentrated to afford a dark red oil. The oil was purified by flash chromatography on C18 silica, eluting with a mixture of acetonitrile in water (5-50% with 0.1% formic acid). The desired fractions were concentrated to remove the acetonitrile before being acidified to pH 2 causing brown crystals to form. The crystals were collected via vacuum filtration to afford the title compound (0.550 g, 28%) as a brown solid. LCMS: 2.37 min, MI 264; method (4LCMS1); $^1$H NMR (400 MHz, Methanol-$d_4$) 9.12 (s, 1H).

Synthesis of 4-chloro-5-(4,5,6-trichloropyrimidin-2-yl)thiazole (6-005)

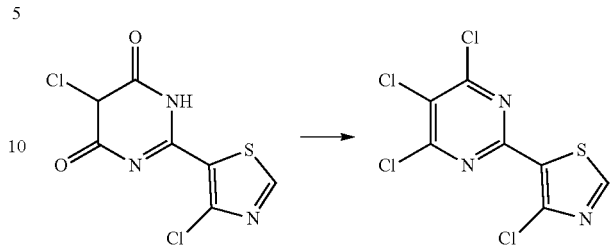

To a stirred solution of 5-chloro-2-(4-chlorothiazol-5-yl)-1H-pyrimidine-4,6-dione (6-004) (550 mg, 2.08 mmol) and N,N-diisopropylethylamine (1.45 mL, 8.33 mmol) in toluene (10 mL) under nitrogen was added phosphorus oxychloride (0.78 mL, 8.33 mmol) dropwise and the mixture was heated at 100° C. for 1 h. The reaction was cooled to room temperature and then added dropwise to a solution of ammonium hydroxide 50:50 in ice with DCM (100 mL). After complete addition the two phases were separated and the aqueous was further extracted with DCM (2×100 mL). The combined organics were washed with a saturated aqueous sodium citrate solution (2×100 mL) before being passed through a phase separator. The organics were concentrated to afford a brown powder. The powder was triturated in methanol and the resulting solid was collected via vacuum filtration. The collected cream precipitate was dried under vacuum to afford the title compound (502 mg, 80%). LCMS: RT 5.29 min, MI 302, Method (4LCMS1); $^1$H NMR (400 MHz, CDCl$_3$) δ 8.84 (s, 1H).

Synthesis of tert-butyl 4-[5,6-dichloro-2-(4-chlorothiazol-5-yl)pyrimidin-4-yl]-3-(difluoromethyl)piperazine-1-carboxylate (6-006)

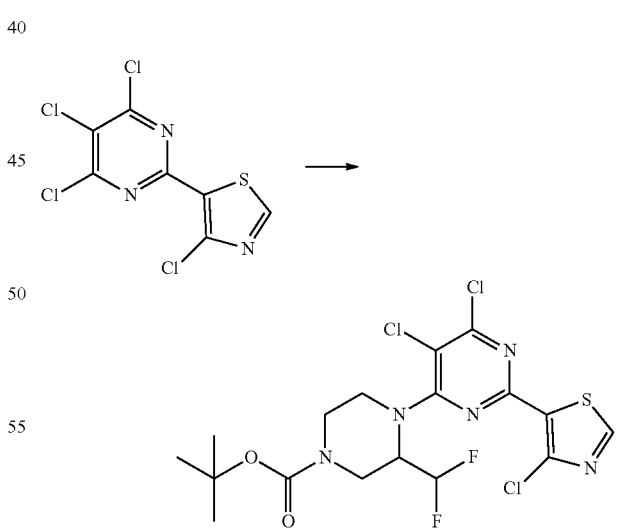

To a stirred solution of tert-butyl 3-(difluoromethyl)piperazine-1-carboxylate (0.43 g, 1.83 mmol) in THF (5 mL) at 0° C. under nitrogen was added sodium hydride (60% in mineral oil, 0.09 g, 2.168 mmol) in portions. Once addition was complete the mixture was stirred for 20 min. The deprotonated amine solution was added dropwise to a stirred solution of 4-chloro-5-(4,5,6-trichloropyrimidin-2-yl)thiazole (6-005) (0.50 g, 1.67 mmol) in THF (5 mL) also at 0° C. under nitrogen. The mixture was allowed to warm to room temperature with stirring for 1 h, before being heated to reflux for 96 h. The reaction was cooled to room temperature and diluted with ethyl acetate (200 mL). The organics were washed with water (2×200 mL). The combined aqueous were extracted with ethyl acetate (3×200 mL). The combined organics were dried (MgSO$_4$) and concentrated to dryness affording a brown oil. The oil was purified by flash chromatography on silica gel eluting with a mixture of ethyl acetate in cyclohexane (0-100%) to afford the title compound (0.40 g, 47%) as a cream powder. LCMS: 5.81 min, MI 502, Method (4LCMS1); $^1$H NMR (400 MHz, DMSO-d$_6$) δ 9.27 (s, 1H), 6.45 (t, J=54.9 Hz, 1H), 4.94 (s, 1H), 4.26 (d, J=14.3 Hz, 1H), 4.16 (d, J=13.7 Hz, 1H), 4.08-3.95 (m, 1H), 3.60-3.47 (m, 1H), 3.34-3.24 (m, 1H), 3.01 (s, 1H), 1.42 (s, 9H).

Synthesis of tert-butyl 4-[6-allyloxy-5-chloro-2-(4-chlorothiazol-5-yl)pyrimidin-4-yl]-3-(difluoromethyl)piperazine-1-carboxylate (6-007)

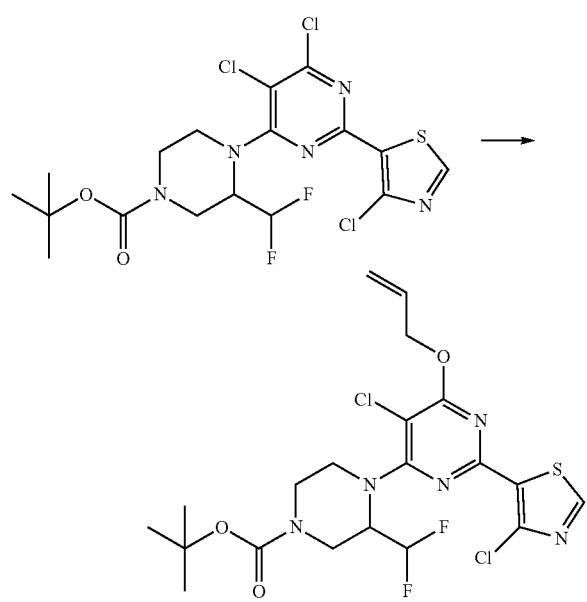

To a stirred solution of allyl alcohol (0.27 mL, 4.00 mmol) in THF (10 mL) at 0° C. under nitrogen was added sodium hydride (60% in mineral oil, 0.16 g, 4.00 mmol) in portions. The mixture was stirred for 10 min. The allyl alcohol mixture was added dropwise to a solution of tert-butyl 4-[5,6-dichloro-2-(4-chlorothiazol-5-yl)pyrimidin-4-yl]-3-(difluoromethyl)piperazine-1-carboxylate (6-006) (0.4 g, 0.801 mmol) in THF (20 mL) also at 0° C. under nitrogen. Once addition was complete the reaction was stirred for a further 10 min. Water (20 mL) was added dropwise and the mixture was extracted with ethyl acetate (3×40 mL). The combined organics were dried (MgSO$_4$) and concentrated to dryness to afford a yellow film. The film was purified using flash chromatography on silica gel eluting with a mixture of ethyl acetate in cyclohexane (0-30%). The desired fractions were concentrated to dryness to afford the title compound (0.358 g, 86%) as a yellow film. LCMS: 6.10 min, MI 466, Method (4LCMS1); $^1$H NMR (400 MHz, CDCl$_3$) δ 8.72 (s, 1H), 6.36-5.95 (m, 2H), 5.48 (dq, J=17.2, 1.5 Hz, 1H), 5.32 (dq, J=10.5, 1.4 Hz, 1H), 5.01 (d, J=5.5 Hz, 2H), 4.73 (s, 1H), 4.40 (d, J=14.1 Hz, 1H), 4.26-4.05 (m, 2H), 3.51 (td, J=14.1, 3.5 Hz, 1H), 3.32 (dt, J=14.2, 3.7 Hz, 1H), 3.20-2.94 (m, 1H), 1.49 (s, 9H).

Synthesis of tert-butyl 4-[5-chloro-2-(4-chlorothiazol-5-yl)-6-oxo-1H-pyrimidin-4-yl]-3-(difluoromethyl)piperazine-1-carboxylate (6-008)

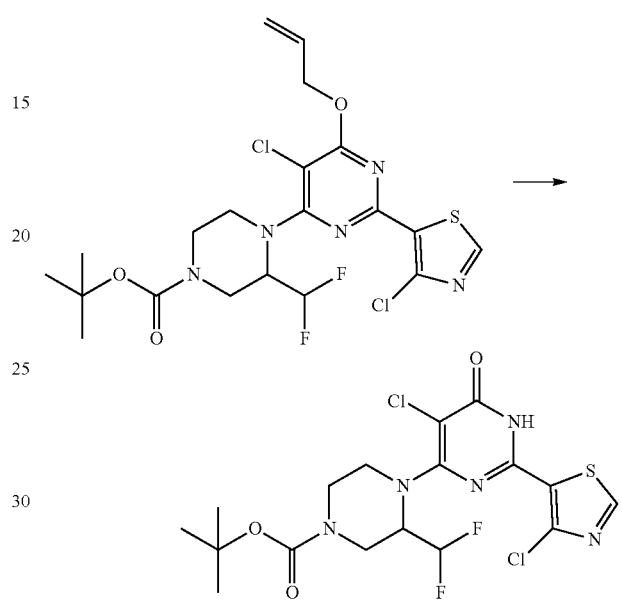

To a degassed solution of tert-butyl 4-[6-allyloxy-5-chloro-2-(4-chlorothiazol-5-yl)pyrimidin-4-yl]-3-(difluoromethyl)piperazine-1-carboxylate (6-007) (0.358 g, 0.685 mmol) and morpholine (0.18 mL, 2.06 mmol) in DCM (8 mL) was added tetrakis(triphenylphosphine) palladium (0.04 g, 0.034 mmol). The mixture was stirred for 5 min under nitrogen. Water (10 mL) and DCM (10 mL) were added and the two phases were separated. The organics were concentrated to dryness to afford a yellow oil. The oil was purified using flash chromatography on silica gel eluting with a mixture of methanol in DCM (0-10% with 0.1% ammonia). The desired fractions were concentrated to dryness to afford the title compound (0.178 g, 54%) as a pale yellow film. LCMS: 4.44 min, MI 482, Method (4LCMS1); $^1$H NMR (400 MHz, CDCl$_3$) b 8.87 (s, 1H), 6.06 (td, J=55.9, 5.0 Hz, 1H), 4.78-4.47 (m, 1H), 4.39 (d, J=14.1 Hz, 1H), 4.21 (s, 1H), 4.03 (d, J=13.7 Hz, 1H), 3.48 (dd, J=12.3, 3.2 Hz, 1H), 3.25 (d, J=14.2 Hz, 1H), 3.02 (s, 1H), 1.49 (s, 9H).

Chiral Separation of tert-butyl 4-[5-chloro-2-(4-chlorothiazol-5-yl)-6-oxo-1H-pyrimidin-4-yl]-3-(difluoromethyl)piperazine-1-carboxylate tert-Butyl 4-[5-chloro-2-(4-chlorothiazol-5-yl)-6-oxo-1H-pyrimidin-4-yl]-3-(difluoromethyl)piperazine-1-carboxylate (6-008) (0.18 g, 0.369 mmol) was dissolved to 30 mg/mL in methanol and was then purified by SFC (Column=Lux C1 (21.2 mm×250 mm, 5 μm; Column temperature 40° C.; Flow rate=50 mL/min, BPR=125 BarG, Isocratic conditions 40:60 MeOH:CO$_2$). Appropriate fractions containing the first eluting isomer (enantiomer 1, unknown absolute stereochemistry) were concentrated to dryness affording tert-butyl 4-[5-chloro-2-(4-chlorothiazol-5-yl)-6-oxo-1H-pyrimidin-4-yl]-3-(difluoromethyl)piperazine-1-carboxylate, enantiomer 1 (6-009) (0.0686 g, 39%) as a cream powder with 98.4% ee (RT: 2.76 min; Column details: Lux C1 4.6 mm×250 mm, 5 μm; Column Temperature: 40° C.; Flow Rate: 4 mL/min; Isocratic Conditions: 40:60 MeOH:CO$_2$). LCMS: 2.49 min, MI 480, Method (4LCMS3); $^1$H NMR (400 MHz, CDCl$_3$) δ 8.89 (s, 1H), 6.07 (td, J=55.8, 4.9 Hz, 1H), 4.63 (s, 1H), 4.39 (d, J=14.1 Hz, 1H), 4.28-4.13 (m, 1H), 4.05 (d, J=13.4 Hz, 1H), 3.49 (td, J=13.1, 3.4 Hz, 1H), 3.25 (d, J=13.7 Hz, 1H), 3.02 (s, 1H), 1.49 (s, 9H).

The appropriate fractions containing the second eluting isomer (enantiomer 2, unknown absolute stereochemistry) were concentrated to dryness affording tert-butyl 4-[5-chloro-2-(4-chlorothiazol-5-yl)-6-oxo-1H-pyrimidin-4-yl]-3-(difluoromethyl)piperazine-1-carboxylate, enantiomer 2 (6-010) (0.0709 g, 40%) as a cream powder with 98.6% ee (RT: 3.16 min; Column details: Lux C1 4.6 mm×250 mm, 5 μm; Column Temperature: 40° C.; Flow Rate: 4 mL/min; Isocratic Conditions: 40:60 MeOH:CO$_2$). LCMS: 2.49 min, MI 480, Method (4LCMS3); $^1$H NMR (400 MHz, CDCl$_3$) δ 8.87 (s, 1H), 6.07 (td, J=55.9, 4.9 Hz, 1H), 4.63 (s, 1H), 4.39 (d, J=14.1 Hz, 1H), 4.26-4.11 (m, 1H), 4.04 (d, J=13.7 Hz, 1H), 3.56-3.43 (m, 1H), 3.25 (d, J=13.8 Hz, 1H), 3.02 (s, 1H), 1.49 (s, 9H).

Synthesis of 5-chloro-2-(4-chlorothiazol-5-yl)-4-[2-(difluoromethyl)piperazin-1-yl]-1H-pyrimidin-6-one hydrochloride, Enantiomer 1 (69)

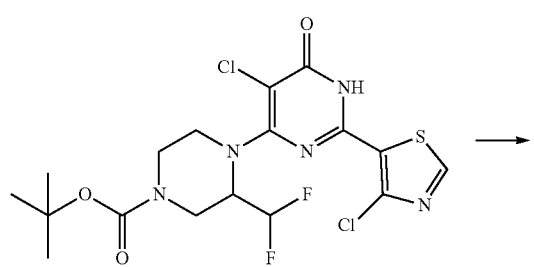

To a stirred solution of tert-butyl 4-[5-chloro-2-(4-chlorothiazol-5-yl)-6-oxo-1H-pyrimidin-4-yl]-3-(difluoromethyl)piperazine-1-carboxylate, enantiomer 1 (6-009) (69 mg, 0.142 mmol) in DCM (2 mL) was added hydrogen chloride (1.42 mL of a 4 M solution in 1,4-dioxane, 2.85 mmol). The mixture was stirred for 20 min. Diethyl ether (10 mL) was added and the resulting precipitate was collected via vacuum filtration. The cream powder was dried in vacuo to afford the title compound (46.1 mg, 77%). LCMS: 1.75 min, MI 382, Method (4LCMS1); $^1$H NMR (400 MHz, DMSO-d$_6$) δ 13.11 (s, 1H), 9.36 (s, 1H), 9.25 (s, 1H), 8.99 (s, 1H), 6.68 (td, J=55.1, 4.8 Hz, 1H), 4.92 (t, J=13.3 Hz, 1H), 4.19 (d, J=14.5 Hz, 1H), 3.63-3.51 (m, 2H), 3.42-3.24 (m, 2H), 3.19-3.04 (m, 1H).

Synthesis of 5-chloro-2-(4-chlorothiazol-5-yl)-4-[2-(difluoromethyl)piperazin-1-yl]-1H-pyrimidin-6-one hydrochloride, Enantiomer 2 (70)

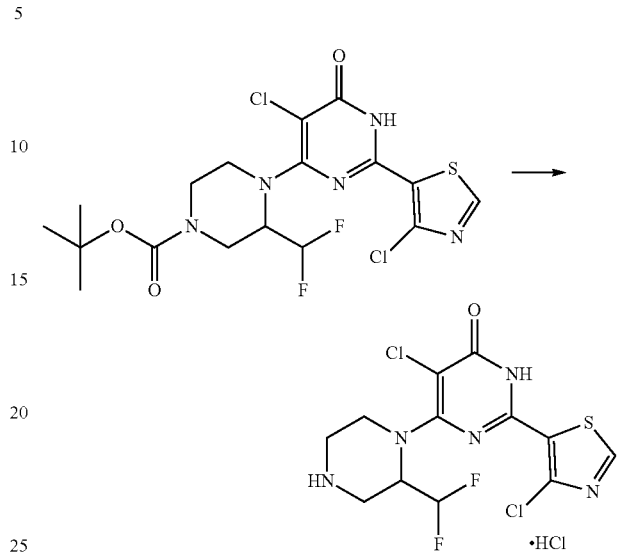

To a stirred solution of tert-butyl 4-[5-chloro-2-(4-chlorothiazol-5-yl)-6-oxo-1H-pyrimidin-4-yl]-3-(difluoromethyl)piperazine-1-carboxylate, enantiomer 2 (6-010) (70 mg, 0.147 mmol) with DCM (2 mL) was added hydrogen chloride (1.47 mL of a 4 M solution in 1,4-dioxane, 2.94 mmol). The mixture was stirred for 1 h. Diethyl ether (10 mL) was added and the resulting precipitate was collected via vacuum filtration. The cream powder was dried in vacuo overnight to afford the title compound (50 mg, 82%). LCMS: 1.75 min, MI 382, Method (4LCMS1); $^1$H NMR (400 MHz, DMSO-d$_6$) δ 13.11 (s, 1H), 9.47 (s, 1H), 9.25 (s, 1H), 9.07 (s, 1H), 6.71 (td, J=55.1, 5.0 Hz, 1H), 4.94 (s, 1H), 4.20 (d, J=14.8 Hz, 1H), 3.67-3.48 (m, 2H), 3.40-3.26 (m, 2H), 3.13 (t, J=12.2 Hz, 1H).

Synthesis of tert-butyl 4-[5,6-dichloro-2-(4-chlorothiazol-5-yl)pyrimidin-4-yl]-6-fluoro-1,4-diazepane-1-carboxylate (6-011)

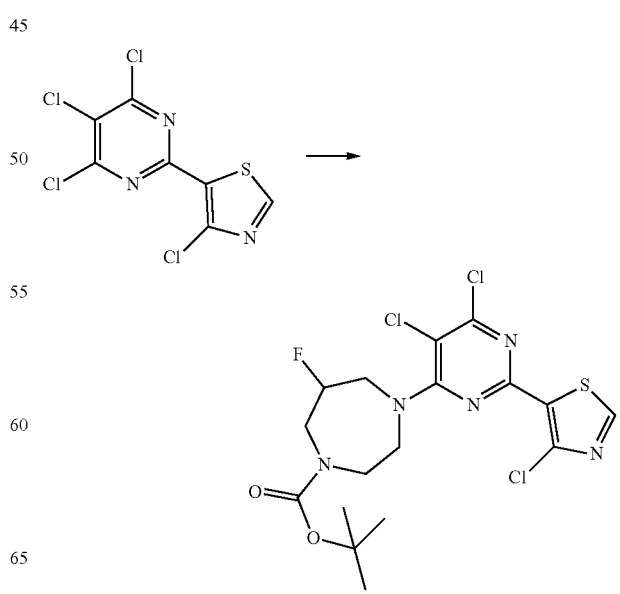

A solution of 4-chloro-5-(4,5,6-trichloropyrimidin-2-yl)thiazole (6-005) (398 mg, 1.32 mmol) and triethylamine (0.19 mL, 1.39 mmol) in chloroform (11 mL) was prepared, to which tert-butyl 6-fluoro-1,4-diazepane-1-carboxylate (0.29 g, 1.32 mmol) was added. The reaction mixture was stirred for 5 days. The crude reaction mixture was partitioned between DCM (400 mL) and water (400 mL). The organic phase was separated and the aqueous phase was extracted further with DCM (2×200 mL). The combined organic phase was dried over MgSO₄, filtered and concentrated by rotary evaporation to give the title compound (614 mg, 64%). LCMS: RT 5.72 min, MI 383, Method (4LCMS1).

Synthesis of tert-butyl 4-[6-allyloxy-5-chloro-2-(4-chlorothiazol-5-yl)pyrimidin-4-yl]-6-fluoro-1,4-diazepane-1-carboxylate (6-012)

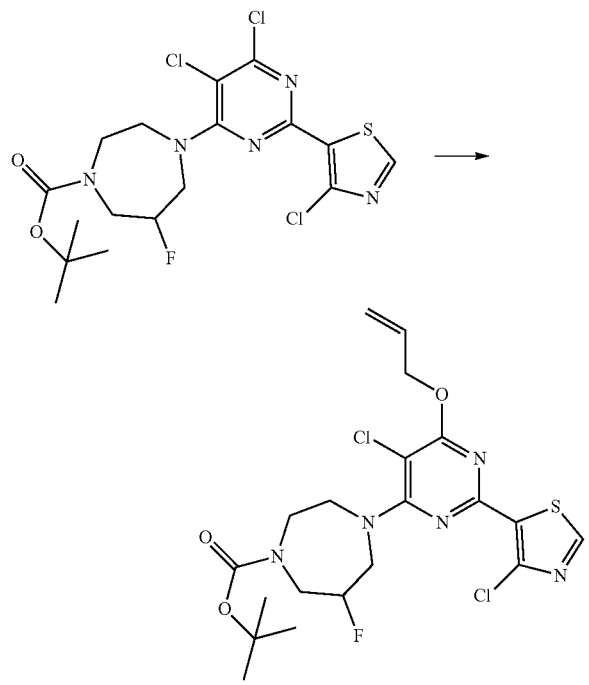

To a stirred solution of allyl alcohol (0.28 mL, 4.14 mmol) in THF (10 mL) at 0° C. under nitrogen was added sodium hydride (60% in mineral oil, 0.17 g, 4.14 mmol) in portions. The mixture was stirred for 10 min. The allyl alcohol mixture was added dropwise to a solution of tert-butyl 4-[5,6-dichloro-2-(4-chlorothiazol-5-yl)pyrimidin-4-yl]-6-fluoro-1,4-diazepane-1-carboxylate (6-011) (0.4 g, 0.829 mmol) in THF (20 mL) also at 0° C. under nitrogen. Once addition was completed, the reaction was stirred for a further 10 min. Water (20 mL) was added dropwise and the mixture was extracted with ethyl acetate (3×40 mL). The combined organics were dried (MgSO₄) and concentrated to dryness to afford a yellow film. The film was purified using flash chromatography on silica gel eluting with a mixture of ethyl acetate in cyclohexane (0-30%). The desired fractions were concentrated to dryness to afford the title compound (0.290 g, 69%) as a yellow film. LCMS: 6.06 min, MI 504, Method (4LCMS1); ¹H NMR (400 MHz, CDCl₃) δ 8.71 (s, 1H), 6.11 (ddt, J=17.2, 10.5, 5.6 Hz, 1H), 5.47 (dq, J=17.2, 1.6 Hz, 1H), 5.31 (dq, J=10.4, 1.3 Hz, 1H), 5.22-5.01 (m, 1H), 4.99 (d, J=5.6 Hz, 2H), 4.32-3.91 (m, 4H), 3.87-3.55 (m, 4H), 1.42 (s, 9H).

Synthesis of tert-butyl 4-[5-chloro-2-(4-chlorothiazol-5-yl)-6-oxo-1H-pyrimidin-4-yl]-6-fluoro-1,4-diazepane-1-carboxylate (6-013)

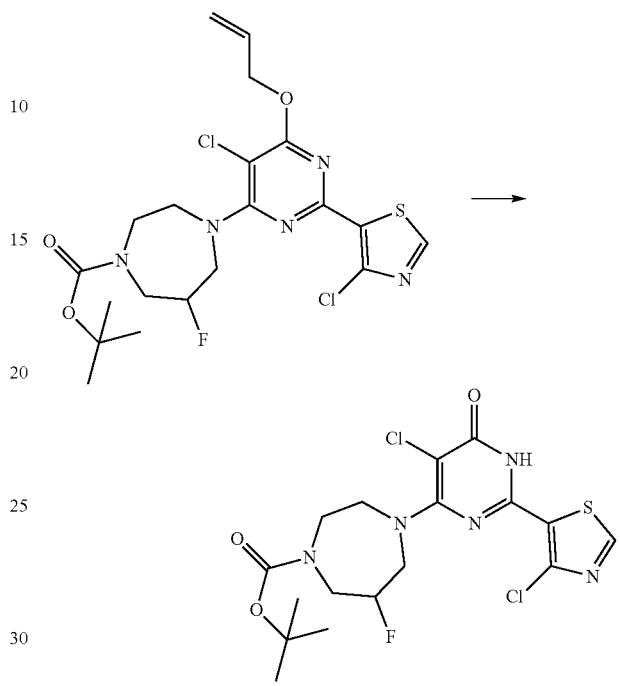

To a degassed solution of tert-butyl 4-[6-allyloxy-5-chloro-2-(4-chlorothiazol-5-yl)pyrimidin-4-yl]-6-fluoro-1,4-diazepane-1-carboxylate (6-012) (290 mg, 0.575 mmol) and morpholine (0.15 mL, 1.73 mmol) in DCM (5 mL) was added Pd(dppf)C₂ complex with DCM (0.02 g, 0.029 mmol). The mixture was stirred for 5 min under nitrogen. Water (10 mL) and DCM (10 mL) were added and the two phases separated. The organics were concentrated to dryness to afford a yellow oil. The oil was purified using flash chromatography on C18 silica gel eluting with a mixture of acetonitrile in water (5-60% with 0.1% formic acid). The desired fractions were concentrated to dryness to afford the title compound (0.149 g, 56%) as a pale yellow powder. LCMS: 4.21 min, MI 464, Method (4LCMS1); ¹H NMR (400 MHz, CDCl₃) δ 8.88 (s, 1H), 5.42-4.78 (m, 1H), 4.25-3.93 (m, 3H), 3.89-3.28 (m, 5H), 1.50-1.37 (m, 9H).

Synthesis of 5-chloro-2-(4-chlorothiazol-5-yl)-4-(6-fluoro-1,4-diazepan-1-yl)-1H-pyrimidin-6-one hydrochloride (racemic) (71)

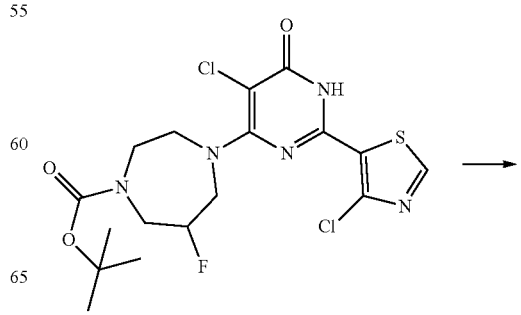

-continued

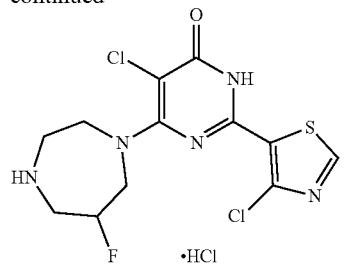

To a stirred solution of tert-butyl 4-[5-chloro-2-(4-chlorothiazol-5-yl)-6-oxo-1H-pyrimidin-4-yl]-6-fluoro-1,4-diazepane-1-carboxylate (6-013) (33.0 mg, 0.071 mmol) in DCM (1.5 mL) was added hydrogen chloride (0.36 mL, 1.421 mmol, 4 M in dioxane). The mixture was allowed to stir for 3 days before concentrating under reduced pressure to afford an orange powder. The powder was sonicated into DCM (2 mL) and ether (2 mL). The resulting solid was collected via vacuum filtration. The collected brown solid was sonicated in methanol, filtered, and the filtrate concentrated to afford a brown powder. This was sonicated in DCM and 2 M HCl in diethyl ether. The resulting solid was collected via vacuum filtration and dried in vacuo to afford the title compound (9.7 mg, 34%) as a brown powder. LCMS: RT 1.76 min, MI 364, Method (4LCMS1); $^1$H NMR (400 MHz, DMSO-$d_6$) δ 12.74 (s, 1H), 9.84 (s, 1H), 9.23 (s, 1H), 9.16 (s, 1H), 5.34 (d, J=44.4 Hz, 1H), 4.44-4.29 (m, 1H), 4.27-4.12 (m, 2H), 3.98-3.86 (m, 1H), 3.62-3.42 (m, 3H), 3.31 (s, 1H).

Chiral Separation of tert-butyl 4-[5-chloro-2-(4-chlorothiazol-5-yl)-6-oxo-1H-pyrimidin-4-yl]-6-fluoro-1,4-diazepane-1-carboxylate tert-butyl 4-[5-chloro-2-(4-chlorothiazol-5-yl)-6-oxo-1H-pyrimidin-4-yl]-6-fluoro-1,4-diazepane-1-carboxylate (6-013) (0.15 g, 0.32 mmol) was dissolved to 30 mg/mL in methanol and was then purified by SFC (Column=Amy-C (20 mm×250 mm, 5 μm; Column temperature 40° C.; Flow rate=50 mL/min, BPR=125 BarG, Isocratic conditions 35:65 MeOH:CO$_2$). Appropriate fractions containing the first eluting isomer (enantiomer 1, unknown absolute stereochemistry) were concentrated to dryness affording tert-butyl 4-[5-chloro-2-(4-chlorothiazol-5-yl)-6-oxo-1H-pyrimidin-4-yl]-6-fluoro-1,4-diazepane-1-carboxylate, enantiomer 1 (6-014) (59.3 mg, 40%) as a brown powder with 100% ee (RT: 2.25 min; Column details: Lux A1 4.6 mm×250 mm, 5 μm; Column Temperature: 40° C.; Flow Rate: 4 mL/min; Isocratic Conditions: 35:65 MeOH:CO$_2$). LCMS: 2.41 min, MI 464, Method (4LCMS3); $^1$H NMR (400 MHz, CDCl$_3$) δ 8.86 (s, 1H), 5.20-4.83 (m, 1H), 4.19-3.94 (m, 3H), 3.92-3.27 (m, 5H), 1.49-1.40 (m, 9H).

The appropriate fractions containing the second eluting isomer (enantiomer 2, unknown absolute stereochemistry) were concentrated to dryness affording tert-butyl 4-[5-chloro-2-(4-chlorothiazol-5-yl)-6-oxo-1H-pyrimidin-4-yl]-6-fluoro-1,4-diazepane-1-carboxylate, enantiomer 2 (6-015) (60.4 mg, 41%) as a brown powder with 98.8% ee (RT: 2.26 min; Column details: Lux A1 4.6 mm×250 mm, 5 μm; Column Temperature: 40° C.; Flow Rate: 4 mL/min; Isocratic Conditions: 35:65 MeOH:CO$_2$). LCMS: 2.37 min, MI 464, Method (4LCMS3); $^1$H NMR (400 MHz, CDCl$_3$) δ 8.87 (S, 1H), 5.18-4.88 (m, 1H), 4.18-3.95 (m, 3H), 3.93-3.27 (m, 5H), 1.58-1.16 (m, 9H).

Synthesis of 5-chloro-2-(4-chlorothiazol-5-yl)-4-(6-fluoro-1,4-diazepan-1-yl)-1H-pyrimidin-6-one hydrochloride, Enantiomer 1 (72)

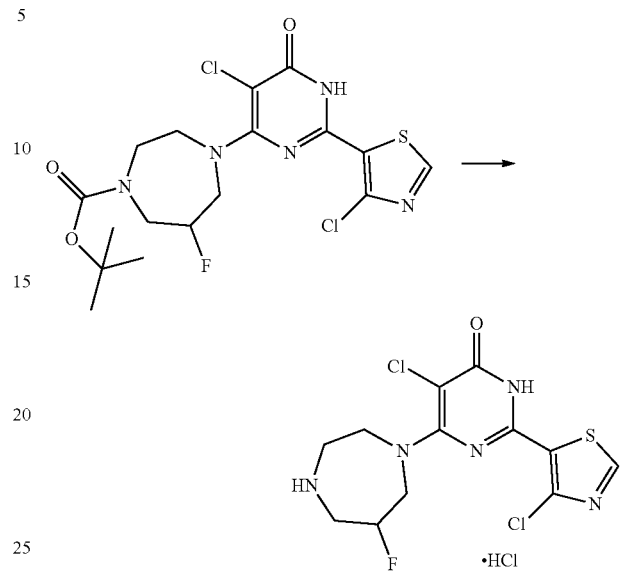

To a stirred solution of tert-butyl 4-[5-chloro-2-(4-chlorothiazol-5-yl)-6-oxo-1H-pyrimidin-4-yl]-6-fluoro-1,4-diazepane-1-carboxylate, enantiomer 1 (6-014) (0.06 g, 0.128 mmol) in DCM (2 mL) was added hydrogen chloride (0.64 mL, 2.55 mmol) (4.0 M in 1,4-dioxane). The mixture was stirred for 20 min. The reaction mixture was then concentrated to dryness and suspended in ether. The resulting precipitate was collected via vacuum filtration and dried under vacuum to afford the title compound (42.5 mg, 83%) as a brown powder. LCMS: 1.71 min, MI 364, Method (4LCMS1); $^1$H NMR (400 MHz, DMSO-$d_6$) δ 12.75 (s, 1H), 9.77 (s, 1H), 9.23 (s, 1H), 9.14-8.90 (m, 1H), 5.32 (d, J=44.9 Hz, 1H), 4.42-4.30 (m, 1H), 4.26-4.10 (m, 2H), 4.00-3.85 (m, 1H), 3.62-3.40 (m, 4H).

Synthesis of 5-chloro-2-(4-chlorothiazol-5-yl)-4-(6-fluoro-1,4-diazepan-1-yl)-1H-pyrimidin-6-one hydrochloride, Enantiomer 2 (73)

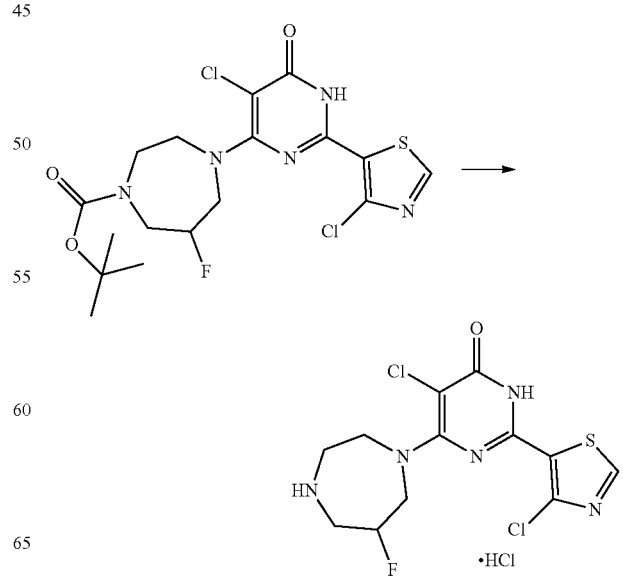

To a stirred solution of tert-butyl 4-[5-chloro-2-(4-chlorothiazol-5-yl)-6-oxo-1H-pyrimidin-4-yl]-6-fluoro-1,4-diazepane-1-carboxylate, enantiomer 2 (6-015) (0.06 g, 0.13 mmol) in DCM (2 mL) was added hydrogen chloride (1.3 mL of a 4 M solution in 1,4-dioxane, 2.60 mmol). The mixture was stirred for 20 min. The reaction mixture was then concentrated to dryness and suspended in ether causing a brown precipitate to form. The precipitate was collected via vacuum filtration and dried under vacuum to afford the title compound (51.8 mg, 99%) as a brown powder. LCMS: 2.00 min, MI 364, Method (2LCMS1); $^1$H NMR (400 MHz, DMSO-$d_6$) δ 12.75 (s, 1H), 9.78 (s, 1H), 9.23 (s, 1H), 9.07 (s, 1H), 5.34 (d, J=43.9 Hz, 1H), 4.43-4.30 (m, 1H), 4.27-4.12 (m, 2H), 3.99-3.87 (m, 1H), 3.65-3.39 (m, 4H).

Biology

Assays and Model Systems and Methods

The compounds disclosed herein were tested for their ability to inhibit the activity of Cdc7 according to the methods described below. In general, the compounds of Formula I were found to effectively inhibit the activity of Cdc7.

Cdc7 Biochemical Assays

Method 1

This protocol describes a method for assaying Cdc7/ASK for activity. The assay is a 384 well ELISA assay, utilising a whole protein substrate (MCM2) and an antibody against Phospho MCM2 (S53). This site is thought to be specific to Cdc7/ASK phosphorylation and the assay has been validated using knockout mutants.

Reagents

TBS: 25 mM Tris pH 7.2, 150 mM NaCl. (Dilute 10× stock by 1:10).

Wash Buffer: TBS+0.05% Tween 20. (Add 100 mL 1 M Tris pH 7.2, 120 mL 5 M NaCl and 2 mL 100% Tween 20 per 4 L).

Kinase Reaction Buffer: 50 mM Tris-HCl pH 8.5, 10 mM $MgCl_2$, 1 mM DTT. (Dilute 10× stock by 1:10 and add 100 µL 1M DTT per 100 mL prior to assay).

Diethanolamine Buffer: 1 M diethanolamine pH 9.8, 0.5 mM $MgCl_2$.

Stop Solution: 1 M NaOH.

MCM2 was expressed and purified in-house and used in the assay at a final assay concentration of 436 ng/well.

Cdc7/ASK is purchased from commercial suppliers and used in the assay at a final assay concentration of 37.97 ng/well or 20.63 nM.

ATP used as a final assay concentration of 2 µM.

Primary Antibody: Rabbit anti-Phospho MCM2 (S53) Antibody (BL3353)), is purchased from commercial suppliers at 0.2 mg/mL and used at a final assay concentration by diluting 1:800 in TBS.

Secondary Antibody: Anti-Rabbit/AP Antibody is supplied is purchased from commercial suppliers at 1 mg/mL and used at a final assay concentration by diluting 1:2000 in TBS.

Development Reagent: Dissolve one 20 mg PNPP tablet (Sigma, product N2765, 20 mg per tablet) per 20 mL diethanolamine Buffer (or one 5 mg PNPP tablet per 5 mL diethanolamine buffer). Cover in foil and leave shaking on a roller shaker at room temperature for up to an hour to dissolve.

Methods

1. Add 20 µL 1× working stock of Substrate (MCM2) in TBS to all wells of a clear, 384 well, Nickel-chelate microplate to give a final concentration of 250 ng/well. Incubate at room temperature for at least 1 hour. Plates can be pre-coated for 1 hour and stored at 4° C. for up to 8 days.
2. Wash with TBS+0.05% Tween 20 (80 µL×3).
3. Add 2 µL 10× test compounds, including the positive control, in 40% DMSO/water to 'test' wells. Add 2 µL 40% DMSO/water to 'control' and 'blank' wells. The final DMSO concentration will be 4%.
4. Add 13 µL CDC7/ASK Kinase (1.5× stock) in Kinase Reaction Buffer to 'test' and 'control' wells to give a final concentration of 5 ng/well. Add 13 µL Kinase Reaction Buffer to 'blank' wells.
5. Add 5 µL ATP (4× stock) in Kinase Reaction Buffer to all wells to give a final concentration of 2 µM.
6. Incubate at room temperature for 90 minutes.
7. Wash with TBS+0.05% Tween 20 (80 µL×3).
8. Add 20 µL 1× working solution of Primary Antibody in TBS to all wells. Incubate at room temperature for 30 minutes.
9. Wash with TBS+0.05% Tween 20 (80 µL×3).
10. Add 20 µL 1× working solution of Secondary Antibody in TBS to all wells. Incubate at room temperature for 30 minutes.
11. Wash with TBS+0.05% Tween 20 (80 µL×3).
12. Add 20 µL 1× Development Reagent to all wells.
13. Incubate at room temperature for 2 hours. Stop the reaction by adding 20 µL Stop Solution to all wells and record Absorbance on a Pherastar plate reader.

Percentage inhibition values were calculated from absorbance values, using the no compound (DMSO) and no enzyme control values as 0% and 100% inhibition, respectively. $IC_{50}$ determination was performed with ExcelFit software (IDBS) using curve fit 205. Z' factors were determined for each plate tested and were all above 0.5.

Method 2

This protocol describes a method for assaying a compounds' ability to inhibit Cdc7 activity by measuring pS40MCM2 levels in a Cdc7/Dbf4 Enzyme TR-FRET Assay.

2.5 nM Cdc7/Dbf4 was incubated with 100 nM of biotin-labelled peptide 35-TDALTS(pS)PGRDLP in the presence of 1 µM ATP at 25° C. for 120 minutes. The phosphorylation of the peptide was detected using TR-FRET. Anti-Mcm2 (pS40) antibody, Terbium anti-rabbit secondary antibody and Streptavidin-Alexa Fluor488 form the detection system.

Method 3

This protocol describes a method for assaying Cdc7/ASK for activity. The assay is an off-chip mobility shift assay (MSA) run at Carna Biosciences.

Materials and Methods

1. Preparation of Test Compound Solution.

The test compound was dissolved in and diluted with dimethylsulfoxide (DMSO) to achieve 100-fold higher concentration which was specified by the sponsor. Then the solution was further 25-fold diluted with assay buffer to make the final test compound solution. Reference compounds for assay control were prepared similarly.

2. Kinase

Cdc7/ASK: Full-length human Cdc7 [1-574(end) amino acids of accession number NP_003494.1] was co-expressed as N-terminal GST-fusion protein (92 kDa) with Dbf4(ASK) [1-674(end) amino acids of accession number NP_006707.1] using baculovirus expression system. GST-Cdc7 was purified by using glutathione sepharose chromatography.

3. Assay Reagents and Procedures
Off-Chip Mobility Shift Assay (MSA)
1) The 5 mL of ×4 compound solution, 5 mL of ×4 Substrate/ATP/Metal solution, and 10 mL of ×2 kinase solution were prepared with assay buffer (20 mM HEPES, 0.01% Triton X-100, 1 mM DTT, pH 7.5) and mixed and incubated in a well of polypropylene 384 well microplate for 5 hours at room temperature.
2) 70 mL of Termination Buffer (QuickScout Screening Assist MSA; Carna Biosciences) was added to the well.
3) The reaction mixture was applied to LabChip system (Perkin Elmer), and the product and substrate peptide peaks were separated and quantitated.
4) The kinase reaction was evaluated by the product ratio calculated from peak heights of product (P) and substrate (S) peptides (P/(P+S)).
4. Reaction Conditions

| Kinase | Platform | Substrate Name | (nM) | ATP (μM) Km | Assay | Metal Name | (mM) | Positive control |
|---|---|---|---|---|---|---|---|---|
| Cdc7/ASK | MSA | MCM2 peptide | 1000 | 2.8 | 5 | Mg | 10 | Staurosporine |

Reaction time is 5 hours.
5. Data Analysis
The readout value of reaction control (complete reaction mixture) was set as a 0% inhibition, and the readout value of background (Enzyme(−)) was set as a 100% inhibition, then the percent inhibition of each test solution was calculated.
$IC_{50}$ value was calculated from concentration vs. % Inhibition curves by fitting to a four parameter logistic curve.
Results

| Number | Biochemical method 1 ($pIC_{50}$) | Biochemical Method 2 ($pIC_{50}$) | Biochemical method 3 ($pIC_{50}$) |
|---|---|---|---|
| 1 | 6.64 | | |
| 2 | 8.50 | | |
| 3 | 7.24 | | |
| 4 | 8.79 | | |
| 5 | 6.90 | | |
| 6 | 8.42 | 8.71 | |
| 7 | 6.61 | | |
| 8 | 7.52 | | |
| 9 | 6.25 | | |
| 10 | 7.03 | | |
| 11 | 6.16 | | |
| 12 | 6.44 | | |
| 13 | 7.48 | | |
| 14 | 8.74 | | |
| 15 | 7.43 | | |
| 16 | 8.56 | 8.14 | |
| 17 | 8.92 | 8.84 | |
| 18 | 7.22 | | |
| 19 | 7.39 | | |
| 20 | 8.35 | | |
| 21 | 8.40 | | |
| 22 | 8.36 | | |
| 23 | 8.48 | | |
| 24 | 8.40 | | |
| 25 | 8.32 | | |
| 26 | 8.78 | | |
| 27 | 7.25 | | |
| 28 | 8.68 | | |
| 29 | 8.50 | | |
| 30 | 8.46 | | |
| 31 | 8.44 | | |
| 32 | 8.06 | | |
| 33 | 8.57 | | |
| 34 | 6.80 | | |
| 35 | 8.85 | | |
| 36 | 8.23 | | |
| 37 | 8.48 | | |
| 38 | 8.64 | | |
| 39 | 7.67 | 8.13 | |
| 40 | | | 8.43 |
| 41 | | 9.08 | 8.4 |
| 42 | | | 8.42 |
| 43 | | 8.74 | 8.41 |
| 44 | | 8.57 | 8.21 |
| 45 | | 8.71 | |
| 46 | | 8.78 | |
| 47 | | 9.11 | |
| 48 | | 8.65 | |
| 49 | | | 7.29 |
| 50 | | | 7.36 |
| 51 | | 8.23 | |
| 52 | | 8.15 | |
| 53 | | 8.89 | |
| 54 | | 7.14 | |
| 56 | | | 7.35 |
| 57 | | | 8.19 |
| 58 | | | 8.15 |
| 59 | | | 8.13 |
| 60 | | | 7.7 |
| 61 | | | 7.89 |
| 62 | | | 7.67 |
| 63 | | | 8.26 |
| 64 | | | 8.38 |
| 65 | | | 8.41 |
| 66 | | | 8.37 |
| 67 | | | 8.22 |
| 68 | | | 8.16 |
| 69 | | | 8.47 |
| 70 | | | 8.17 |
| 71 | | | 8.24 |
| 72 | | | 8.42 |
| 73 | | | 7.99 |

Cdc7 Cell Pharmacodynamics Assays
Method 1
This protocol describes a method to investigate the inhibition of Cdc7 activity of compounds by measuring pS53MCM2 levels in cells after treatment.
Reagents
HCT116 cells (wild type P53 positive)
McCoys 5A media (PAA Laboratories Ltd, E15-022)
10% FCS (Sera Laboratories International Ltd, EU000F Batch:108005)
100× L-Glutamine (Invitrogen, 25030-024)
D-PBS without $CaCl_2$ and $MgCl_2$ (Invitrogen, ref. 14190-094)
Trypsin/EDTA (Invitrogen 25300-054)

2% BSA in PBS
Cell Extraction Buffer (Invitrogen FNN0011)
Protease inhibitor cocktail (Sigma P-2714)
PMSF 0.3M stock in DMSO (Sigma P7626)
Antibody-rabbit pMCM2 Ser53 (Bethyl #A300-756A)
Antibody-goat MCM2 (Bethyl #A300-122A)
Antibody-goat Anti Rabbit IgG HRP (Perbio Science UK Ltd 31462)
1×PBS
FACE Wash buffer (0.02% Triton X100 in 1×PBS)
SuperSignal ELISA Pico Chemiluminescent Substrate (Perbio Science UK Ltd 37070)

Method 72 hours prior to the start of the experiment plate 1×10$^6$ HCT116 cells in a 150 cm$^2$ flask in complete McCoys 5A media (+10% FCS+1× L-glutamine).

Plate 20,000 HCT116 cells per well in standard TC treated 96 well plate in 100 μL complete McCoys 5A media.

Allow cells to settle overnight in incubator set at 37° C. and 5% $CO_2$.

Remove intermediate plate from fridge and place at 37° C. overnight to allow to equilibrate.

Cell treatment: cell assay plate 100 μL; daughter to cell transfer volume 3.33 μL; daughter volume 45 μL; mother plate to daughter volume 5 μL.

Once all cells are treated remove the cells to the incubator and incubate for 6 hours.

Dilute the capture antibody (total MCM2 #A300-122A) 1 in 250 in the required volume of PBS (5 mL per assay plate) and add 50 μL to each well of a Hybond plate excluding wells 12E to 12H. In these wells add 50 μL PBS. Seal the plate and incubate at room temperature for a minimum of 2 hours.

Defrost aliquot of Invitrogen Cell Extraction Buffer (FNN0011) on ice and supplement with appropriate volume of both Sigma protease inhibitor cocktail (P-2714) and PMSF (final conc 1 mM from a 1 M stock in DMSO).

After the 6 hour cell treatment time tap out the media from the assay plates and place them in the −70° C. freezer for at least 5 minutes.

Remove plates from freezer and add 20 μL of ice cold complete lysis buffer on ice. Incubate cells for 30 minutes at 4° C.

Add 80 μL per well 2% BSA.

Transfer 80 μL from the lysis plate to the same wells in the capture/ELISA plate. Cover with plate seal and incubate plates overnight at 4° C.

Wash plates with PBS, remove any residual remaining liquid and add 50 μL per well of pMCM2 Ser53 antibody (#A300-756A) diluted 1 in 100 in 2% BSA. Cover plate and incubate at room temperature for 2 hours with gentle shaking.

Wash plates with PBS, remove any residual remaining liquid and Incubate with 50 μL goat anti rabbit antibody (1 in 800 dilution in 2% BSA) for 1 hour at room temperature.

Wash plates with PBS, remove any residual remaining liquid and add 50 μL mixed SuperSignal Pico substrate.

Incubate each plate for 5 minutes at room temperature shielding the plates from direct light (with a cover plate). Read plates with the luminescent detection.

Method 2

This protocol describes a method to investigate the inhibition of Cdc7 activity by measuring pS40MCM2 levels in cells, after treatment with compounds.

Reagents

HCT116 cells (ATCC, #CCL-247)
McCoys 5A with L-glutamine (Cellgro, #10-050-CV)
10% FCS (Cellgro, #35-010-CV)
D-PBS without $CaCl_2$ and $MgCl_2$ (Cellgro, #21-031-CV)
Trypsin/EDTA (Cellgro, #25-052-CL)
BSA (Calbiochem, 126593)
Cell Extraction Buffer (Invitrogen FNN0011)
Protease inhibitor cocktail (Sigma P-2714)
PMSF 0.3M stock in DMSO (Sigma P7626)
Antibody-rabbit pMCM2 Ser40 (Abcam, AB133243)
Antibody-goat MCM2 (Bethyl #A300-122A)
Antibody-goat Anti Rabbit IgG HRP (Thermo, 31462)
SuperSignal ELISA Pico Chemiluminescent Substrate (Perbio Science UK Ltd 37069)
10×PBS (Growcells, MRGF-6236)
Triton X100 (Sigma, P-T8787)
DMSO (Fisher, D128-1)
2-Propanol (J.T. Baker, 9095-03)

Method

Seed 1×10$^6$ HCT116 cells into each of two 175 cm$^2$ flask containing 30 mL Cell Growth Media and incubate at 37° C., 5% $CO_2$ for 3 days.

Harvest the cells from one T175 cm$^2$ flask and count.

Dilute with Cell Growth Media to a cell density of 2×10$^5$. Dispense 100 μL to each well (20,000 HCT116 cells/well) of TC treated 96-well plate(s).

Allow cells to settle overnight in incubator set at 37° C. and 5% $CO_2$.

Cell treatment: Transfer 0.25 μL/well from the compound plate to the wells of the cell plate(s). This is a 1:400 dilution of compound in the assay.

Once all cells are treated place the cells back to the incubator and incubate for 18 hours.

Dilute the capture antibody (total MCM2 #A300-122A) 1 in 250 in the required volume of PBS (5 mL per assay plate, plus 5 mL for dead volume) and add 50 μL to each well of a Hybond plate except wells A12 & B12. Seal the plate and incubate at room temperature for a minimum of 2 hours.

Defrost aliquot of Invitrogen Cell Extraction Buffer (FNN0011) on ice and supplement with appropriate volume of both Sigma protease inhibitor cocktail (P-2714) and PMSF (final conc 1 mM from a 1 M stock in DMSO).

After the 6 hour or 18 hour cell treatment time, tap out the media from the assay plates and place them in the −70° C. freezer for at least 5 minutes.

Flick out the remaining liquid in the previously prepared capture Ab plate(s) and add 200 μL 2% BSA per well. Incubate for 1 hour at room temperature.

Remove plates from freezer and add 20 μL of ice cold complete lysis buffer. Incubate cells for 30 minutes at 4° C.

Add 30 μL per well 2% BSA

At the end of the 1 hour incubation, wash the Capture/ELISA plate(s) with Wash Buffer on the BioTek plate washer.

Transfer 40 μL per well of the lysis plate(s) to the same wells in the Capture/ELISA plate. Incubate cells overnight at 4° C.

At the end of the overnight incubation, wash the ELISA plate(s) with Wash Buffer on BioTek plate washer.

Prepare Detection Antibody Buffer and dispense 50 μL to all wells of ELISA plate(s) except wells G1 & H1. Cover plate and incubate at room temperature for 2 hours with gentle shaking.

At the end of the 2 hour incubation, wash the ELISA plate(s) with Wash Buffer on the BioTek plate washer.

Prepare the Conjugated Antibody Buffer and dispense 50 µL to all wells of ELISA plate(s).

Cover the plate and incubate at room temperature for 1 hour with gentle shaking.

At the end of the 1 hour incubation, wash the ELISA plate(s) with Wash Buffer on the BioTek plate washer.

Prepare Substrate Buffer and dispense 50 µL to all wells of ELISA plate(s).

Incubate for a minimum of 10 minutes and read plates on the EnVision 2100 Multilabel Reader (Mirror: Luminescence (404) & Luminescence 700 (212); Measurement Height: 6.5 mm; Measurement Time: 0.2 s).

Method 3

This protocol describes a method to investigate the inhibition of Cdc7 activity by measuring pS53MCM2 levels in cells, after treatment with compounds.

Reagents
SW48 cells
RPMI 1640 (Sigma, R5886)
10% FCS (Sera Laboratories International Ltd, EU000F Batch:108005)
100× L-Glutamine (Invitrogen, 25030-024)
D-Glucose Solution (10%) (Sigma, G8644)
HEPES Buffer Solution (Sigma, 83264)
Sodium Pyruvate (Sigma, S8636)
PBS (Fisger, BP399-4)
Trypsin/EDTA (Invitrogen 25300-054)
2% BSA in PBS
Cell Extraction Buffer (Invitrogen FNN0011)
Protease inhibitor cocktail (Sigma P-2714)
PMSF 0.3M stock in DMSO (Sigma P7626)
Antibody-rabbit pMCM2 Ser53 (Bethyl #A300-756A)
Antibody-goat MCM2 (Bethyl #A300-122A)
Antibody-goat Anti Rabbit IgG HRP (Perbio Science UK Ltd 31462)
SuperSignal ELISA Pico Chemiluminescent Substrate (Perbio Science UK Ltd 37070)

Method

Plate 30,000 SW48 cells per well in standard TC treated 96 well plate in 100 µL complete RPMI 1640 medium.

Allow cells to settle overnight in incubator set at 37° C. and 5% $CO_2$.

Cell treatment: prepare a 384 well plate containing 80 µl PBS/well. The PBS should be at room temperature—to be referred to as intermediate plate. Transfer 2 µL of compound from mother plate to intermediate (daughter plate) 1:40 dilution, then 5 µL intermediate to cell (daughter) plate.

Once all cells are treated place the cells back to the incubator and incubate for 6 hours.

Dilute the capture antibody (total MCM2 #A300-122A) 1 in 250 in the required volume of PBS (5 mL per assay plate, plus 5 mL for dead volume) and add 50 µL to each well of a Hybond plate. Seal the plate and incubate at room temperature for a minimum of 2 hours.

Defrost aliquot of Invitrogen Cell Extraction Buffer (FNN0011) on ice and supplement with appropriate volume of both Sigma protease inhibitor cocktail (P-2714) and PMSF (final conc 1 mM from a 1 M stock in DMSO).

After the 6 hour cell treatment time, tap out the media from the assay plates and place them in the −80° C. freezer for at least 5 minutes.

Remove plates from freezer and add 20 µL of ice cold complete lysis buffer, with the multidrop. Incubate cells for 30 minutes at 4° C.

Add 80 µL per well 2% BSA.

Flick out the remaining liquid from the capture plate and transfer 80 µL from the lysis plate to the same wells in the capture/ELISA plate, using the Biomek. Cover with plate seal and incubate plates overnight at 4° C.

Wash plates with PBS, remove any residual remaining liquid and add 50 µL per well of pMCM2 Ser53 antibody (#A300-756A) diluted 1 in 100 in 2% BSA. Cover plate and incubate at room temperature for 2 hours with gentle shaking.

Wash plates with PBS, remove any residual remaining liquid and Incubate with 50 µL goat anti rabbit antibody (1 in 800 dilution in 2% BSA), for 1 hour at room temperature.

Wash plates with PBS, remove any residual remaining liquid and add 50 µL mixed SuperSignal Pico substrate.

Incubate each plate for 5 minutes at room temperature shielding the plates from direct light (with a cover plate). Read plates with the luminescent detection.

Results

| Number | Biomarker Method 1 ($pEC_{50}$) | Biomarker Method 2 ($pEC_{50}$) | Biomarker Method 3 ($pEC_{50}$) |
| --- | --- | --- | --- |
| 2 | 5.70 | | |
| 4 | 7.34 | | 5.83 |
| 6 | 6.97 | | 5.68 |
| 8 | 6.48 | | |
| 12 | 5.44 | | |
| 13 | 5.96 | | |
| 14 | 6.80 | | 5.61 |
| 15 | 5.76 | | |
| 17 | 6.95 | 6.43 | |
| 23 | 5.41 | | |
| 25 | 6.35 | | |
| 28 | 7.34 | | 5.96 |
| 29 | 6.80 | | |
| 30 | 6.60 | | |
| 31 | 7.07 | | |
| 32 | 6.58 | | |
| 33 | 7.00 | | |
| 35 | 7.62 | | |
| 36 | 6.80 | | |
| 37 | 6.96 | | |
| 38 | 7.08 | | |
| 39 | 6.47 | | |
| 40 | | | 6.71 |
| 41 | | 8.14 | 6.50 |
| 42 | | | 6.41 |
| 43 | | 7.42 | 6.46 |
| 44 | | 7.60 | 6.14 |
| 45 | | 7.35 | 5.93 |
| 46 | | 6.82 | |
| 47 | | 7.42 | 5.93 |
| 48 | | 6.34 | |
| 49 | | | 5.34 |
| 50 | | | 5.44 |
| 52 | | 6.07 | 5.24 |
| 53 | | 7.48 | 6.02 |
| 55 | | 7.00 | |
| 56 | | | 5.38 |
| 57 | | | 6.14 |
| 58 | | | 6.48 |
| 59 | | | 6.14 |
| 60 | | | 5.91 |
| 61 | | | 6.79 |
| 62 | | | 6.01 |
| 63 | | | 6.28 |
| 64 | | | 6.78 |
| 65 | | | 7.42 |
| 66 | | | 7.12 |

-continued

| Number | Biomarker Method 1 (pEC$_{50}$) | Biomarker Method 2 (pEC$_{50}$) | Biomarker Method 3 (pEC$_{50}$) |
|---|---|---|---|
| 67 | | | 7.01 |
| 68 | | | 6.70 |
| 69 | | | 7.78 |
| 70 | | | 6.49 |
| 71 | | | 6.60 |
| 72 | | | 7.02 |
| 73 | | | 5.88 |

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise paragraphed. No language in the specification should be construed as indicating any non-paragraphed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the paragraphs appended hereto as permitted by applicable law.

The invention claimed is:
1. A compound of Formula I:

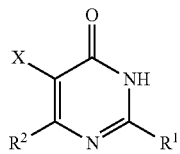

Formula I or a salt or solvate thereof wherein,
X is chosen from halogen, haloC$_1$-C$_6$alkyl, NO$_2$, OCN, SCN, —C(=O)NR$^5$R$^6$, —NHS(O)$_2$R$^6$, and CN;
R$^2$ is a group A-B-C wherein,
A is a bond or is C$_1$-C$_{10}$alkyl;
B is absent or is chosen from S(O)$_p$, NR$^3$, O, C$_2$-C$_{10}$alkenyl, and C$_2$-C$_{10}$alkynyl; and
C is a 3 to 15 membered heterocycloalkyl group or a 4 to 11 membered cycloalkyl group either of which is optionally substituted with one or more R$^5$ groups;
R$^1$ is a heteroaryl group of Formula A

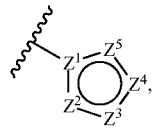

Formula A wherein
Z$^1$ is selected from C and N,
Z$^2$ is selected from CR$^a$, NR$^b$, N, O and S,
Z$^3$ is selected is N and NR$^c$,
Z$^4$ and Z$^5$ are independently selected from O, N, S, NR$^d$ and CR$^e$;
R$^a$ is selected from hydrogen, hydroxyl, halogen, COOR$^3$, C$_1$-C$_6$alkyl, C$_2$-C$_6$alkenyl, C$_2$-C$_6$alkynyl, C$_0$-C$_6$alkylaryl, C$_0$-C$_6$alkylcycloalkyl, C$_0$-C$_6$alkylheterocycloalkyl, C$_0$-C$_6$alkylheteroaryl, C$_0$-C$_6$alkylCN, C$_0$-C$_6$alkylC(=O)C$_0$-C$_6$alkylR$^3$, C$_0$-C$_6$alkylC(=O)C$_0$-C$_6$alkylOR$^3$, C$_0$-C$_6$alkylC(=O)C$_0$-C$_6$alkylNR$^3$R$^4$, haloC$_1$-C$_6$alkyl, NO$_2$, C$_0$-C$_6$alkylNR$^3$R$^4$, C$_0$-C$_6$alkylNR$^3$C$_0$-C$_6$alkylOR$^4$, C$_0$-C$_6$alkylOS(=O)R$^4$, —C$_0$-C$_6$alkylOS(=O)$_2$R$^4$, —C$_0$-C6alkylS(=O)$_p$R$^4$, —OCN, and —SCN, wherein any of the foregoing is optionally substituted with one or more R$^5$ groups; and
R$^b$ and R$^c$ are independently selected from hydrogen, C$_1$-C$_6$ alkyl and C$_3$-C$_6$ cycloalkyl; or
R$^a$ and R$^c$ are taken together to form a fused 6-membered ring optionally substituted with one or more R$^5$ groups;
R$^d$ is selected from hydrogen, C$_1$-C$_6$ alkyl and C$_3$-C$_6$ cycloalkyl;
R$^e$ is selected from hydrogen, hydroxyl, halogen, OR$^3$, COOR$^3$, C$_1$-C$_6$alkyl, C$_2$-C$_6$alkenyl, C$_2$-C$_6$alkynyl, C$_0$-C$_6$alkylaryl, C$_0$-C$_6$alkylcycloalkyl, C$_0$-C$_6$alkylheterocycloalkyl, C$_0$-C$_6$alkylheteroaryl, C$_0$-C$_6$alkylCN, C$_0$-C$_6$alkylC(=O)C$_0$-C$_6$alkylR$^3$, C$_0$-C$_6$alkylC(=O)C$_0$-C$_6$alkylOR$^3$, C$_0$-C$_6$alkylC(=O)C$_0$-C$_6$alkylNR$^3$R$^4$, haloC$_1$-C$_6$alkyl, NO$_2$, C$_0$-C$_6$alkylNR$^3$R$^4$, C$_0$-C$_6$alkylNR$^3$C$_0$-C$_6$alkylOR$^4$, C$_0$-C$_6$alkylOS(=O)R$^4$, —C$_0$-C$_6$alkylOS(=O)$_2$R$^4$, —C$_0$-C$_6$alkylS(=O)$_p$R$^4$, —OCN, and —SCN; or
two adjacent R$_e$ groups, adjacent R$^c$ and R$^e$ or adjacent R$^e$ and R$^d$ groups are taken together to form a fused 6-membered ring optionally substituted with one or more R$^5$ groups;
each R$^3$ and R$^4$ are each independently chosen from H, C$_1$-C$_6$alkyl, C$_2$-C$_6$alkenyl, C$_2$-C$_6$alkynyl, haloC$_1$-C$_6$alkyl, C$_0$-C$_6$alkylaryl, C$_0$-C$_6$alkylcycloalkyl, C$_0$-C$_6$alkylheteroaryl, C$_0$-C$_6$alkylheterocycloalkyl, wherein any of the foregoing, except for H, is optionally substituted with one or more R$^5$; or
R$^3$ and R$^4$ are taken together to form a 3 to 7 membered carbocyclic or heterocyclic ring system, wherein said ring system is optionally substituted with one or more R$^5$;
each R$^5$ is independently chosen from halogen, hydroxyl, OR$^6$, C$_1$-C$_{10}$alkyl, C$_2$-C$_{10}$alkenyl, C$_2$-C$_{10}$alkynyl, C$_0$-C$_6$alkylaryl, C$_0$-C$_6$alkylcycloalkyl, C$_0$-C$_6$alkylheterocycloalkyl, C$_0$-C$_6$alkylheteroaryl, —C$_0$-C$_6$alkylCN, —C$_0$-C$_6$alkylC(=O)C$_0$-C$_6$alkylR$^6$, —C$_0$-C$_6$alkylC(=O)C$_0$-C$_6$alkylOR$^6$, —C$_0$-C$_6$alkylC(=O)C$_0$-C$_6$alkylNR$^6$R$^6$, —C$_0$-C$_6$alkylC(=O)C$_0$-C$_6$alkylNR$^6$C(=O)OR$^6$, haloC$_1$-C$_6$alkyl, NO$_2$, —C$_0$-C$_6$alkylNR$^6$R$^6$, —C$_0$-C$_6$alkylNR$^6$C$_0$-C$_6$alkylOR$^6$, —C$_0$-C$_6$alkylNR$^6$C$_0$-C$_6$alkylC(=O)R$^6$, —C$_0$-C$_6$alkylOR$^6$, (=O), —C$_0$-C$_6$alkylOC(=O)C$_0$-C$_6$alkylR$^6$, —C$_0$-C$_6$alkylOC(=O)C$_0$-C$_6$alkylNR$^6$R$^6$, —C$_0$-C$_6$alkylOC(=O)C$_0$-C$_6$alkylOR$^6$, —C$_0$-C$_6$alkylOS(=O)R$^6$, —C$_0$-C$_6$alkylOS(=O)$_2$R$^6$, —C$_0$-C$_6$alkylOS(=O)$_2$C$_0$-C$_6$alkylOR$^6$, —C$_0$-C$_6$alkylOS(=O)$_2$C$_0$-C$_6$alkylNR$^6$R$^6$, —C$_0$-C$_6$alkylS(=O)$_p$R$^6$, —C$_0$-C$_6$alkylS(=O)$_2$C$_0$-C$_6$alkylNR$^6$R$^6$, —C$_0$-C$_6$alkylS(=O)C$_0$-C$_6$alkylNR$^6$R$^6$, wherein each of the foregoing is optionally substituted with R$^7$, or together with carbon atoms to which they are attached, two $R^5$ groups are linked to form a fused aryl, heteroaryl, 3 to 6 membered heterocycloalkyl or a 3 to 6 membered cycloalkyl;

each $R^6$ is independently chosen from H, $C_1$-$C_{10}$alkyl, $C_2$-$C_{10}$alkenyl, $C_2$-$C_{10}$alkynyl, halo$C_1$-$C_6$alkyl, $C_0$-$C_6$alkylaryl, $C_0$-$C_6$alkylcycloalkyl, $C_0$-$C_6$alkylheteroaryl, $C_0$-$C_6$alkylheterocycloalkyl, wherein each of the foregoing is optionally substituted with $R^7$; or two $R^6$ are taken together to form a 3 to 15 membered carbocyclic or heterocyclic ring system, wherein said ring system is optionally substituted with one or more $R^7$;

each $R^7$ is independently chosen from halogen, hydroxyl, $C_1$-$C_6$alkyl, $OC_1$-$C_6$alkyl, and halo$C_1$-$C_6$alkyl; and each p is independently 0, 1 or 2;

with the proviso that the compound of Formula I is not one of the following compounds:

6-cyclopentyl-5-iodo-2-(5-thiazolyl)-4(3H)-pyrimidinone;
6-cyclopentyl-2-(1-ethyl-1H-pyrazol-4-yl)-5-iodo-4(3H)-pyrimidinone;
6-cyclopentyl-5-iodo-2-(1-propyl-1H-pyrazol-4-yl)-4(3H)-pyrimidinone;
5-bromo-6-cyclopentyl-2(1-ethyl-1H-pyrazol-4-yl)-4(3H)-pyrimidinone;
5-bromo-6-cyclopentyl-2(1-propyl-1H-pyrazol-4-yl)-4(3H)-pyrimidinone;
5-bromo-6-cyclopentyl-2(1-isopropyl-1H-pyrazol-4-yl)-4(3H)-pyrimidinone;
6-cyclopentyl-5-iodo-2(1-isopropyl-1H-pyrazol-4-yl)-4(3H)-pyrimidinone;
5-bromo-6-cyclopentyl-2(5-thiazolyl)-4(3H)-pyrimidinone;
5-bromo-6-cyclopentyl-2(3,5-dimethyl-4-isoxazolyl)-4(3H)-pyrimidinone;
5-bromo-6-cyclopentyl-2(1-propyl-1H-imidazol-5-yl)-4(3H)-pyrimidinone;
6-cyclopentyl-5-iodo-2-(1methyl-1H-pyrazol-3-yl)-4(3H)-pyrimidinone;
5-bromo-6-cyclopentyl-2(1-cyclopropyl-1H-imidazol-5-yl)-4(3H)-pyrimidinone;
5-bromo-6-cyclopentyl-2(1-methyl-1H-pyrazol-3-yl)-4(3H)-Pyrimidinone;
5-bromo-6-cyclopentyl-2(1,5-dimethyl-1H-pyrazol-4-yl)-4(3H)-pyrimidinone;
6-cyclopentyl-5-iodo-2(1,3,5-trimethyl-1H-pyrazol-4-yl)-4(3H)-pyrimidinone;
6-cyclopentyl-5-iodo-2-[1(1-methylethyl)-1H-imidazol-5-yl]-4(3H)-pyrimidinone;
6-cyclopentyl-5-iodo-2-(1-propyl-1H-imidazol-5-yl)-4(3H)-pyrimidinone;
6-cyclopentyl-2-(1-ethyl1H-imidazol-5-yl)-5-iodo-4(3H)-pyrimidinone;
5-bromo-6-cyclopentyl-2(1-methyl-1H-pyrazol-4-yl)-4(3H)-pyrimidinone;
5-bromo-6-cyclopentyl-2(1-methyl-1H-imidazol-5-yl)-4(3H)-pyrimidinone;
6-cyclopentyl-5-iodo-2-(1methyl-1H-pyrazol-4-yl)-4(3H)-pyrimidinone;
5-bromo-6-cyclopentyl-2(1,3-dimethyl-1H-pyrazol-4-yl)-4(3H)-pyrimidinone;
6-cyclopentyl-2-(1,3-dimethyl-1H-pyrazol-4-yl)-5-iodo-4(3H)-pyrimidinone;
6-cyclopentyl-2-(3,5-dimethyl-4-isoxazolyl)-5-iodo-4(3H)-pyrimidinone;
6-cyclopentyl-5-iodo-2-(1-methyl-1H-imidazol-5-yl)-4(3H)-pyrimidinone;
5-bromo-6-cyclopentyl-2-[1(1-methylethyl)-1H-imidazol-5-yl]-4(3H)-pyrimidinone;
5-bromo-6-cyclopentyl-2(3-ethyl-1-methyl-1H-pyrazol-4-yl)-4(3H)-pyrimidinone;
5-bromo-6-cyclopentyl-2(1,3,5-trimethyl-1H-pyrazol-4-yl)-4(3H)-pyrimidinone;
6-cyclopentyl-2-(1,5-dimethyl-1H-pyrazol-4-yl)-5-iodo-4(3H)-pyrimidinone;
5-bromo-6-cyclopentyl-2(1-ethyl-1H-imidazol-5-yl)-4(3H)-Pyrimidinone;
6-cyclopentyl-2-(1-cyclopropyl-1H-imidazol-5-yl)-5-iodo-4(3H)-pyrimidinone;
5-bromo-6-cyclopentyl-2(1H-1,2,4-triazol-5-yl)-4(3H)-pyrimidinone;
6-cyclopentyl-2-(3-ethyl-1-methyl-1H-pyrazol-4-yl)-5-iodo-4(3H)-pyrimidinone;
6-cyclopentyl-5-iodo-2-(1H-1,2,3-triazol-5-yl)-4(3H)-pyrimidinone;
6-cyclopentyl-5-iodo-2-(1H-1,2,4-triazol-5-yl)-4(3H)-pyrimidinone;
5-bromo-6-cyclopentyl-2(1H-1,2,3-triazol-5-yl)-4(3H)-pyrimidinone;
6-cyclopentyl-5-iodo-2-(1-propyl-1H-pyrazol-5-yl)-4(3H)-pyrimidinone;
5-bromo-6-cyclopentyl-2(1-propyl-1H-pyrazol-5-yl)-4(3H)-pyrimidinone;
5-bromo-6-cyclopentyl-2(1-methyl-1H-pyrazol-5-yl)-4(3H)-pyrimidinone;
6-cyclopentyl-5-iodo-2-(1-methyl-1H-pyrazol-5-yl)-4(3H)-pyrimidinone;
5-bromo-6-cyclopentyl-2(1-ethyl-1H-pyrazol-5-yl)-4(3H)-pyrimidinone; and
6-cyclopentyl-2-(1-ethyl-1H-pyrazol-5-yl)-5-iodo-4(3H)-pyrimidinone.

2. A compound according to claim 1 wherein X is chosen from fluoro, chloro, bromo, iodo and CN.

3. A compound according to claim 1, wherein $R^2$ is a group A-B-C wherein:
A is a bond;
B is absent; and
C is a 3 to 7 membered heterocycloalkyl or a 4 to 8 membered cycloalkyl either of which is optionally substituted with one or more $R^5$ group.

4. A compound according to claim 1, wherein C is a 5 to 7 membered heterocycloalkyl which is optionally substituted with one or more $R^5$ groups.

5. A compound according to claim 1, wherein C is selected from:

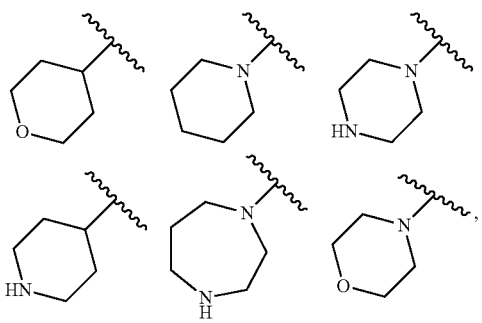

each optionally substituted with one or more $R^5$ groups.

6. A compound according to claim 1, wherein R⁵ is selected from halogen, hydroxyl, OR⁶, C₁-C₁₀alkyl, C₀-C₆alkylC(=O)C₀-C₆alkylR⁶, —C₀-C₆alkylC(=O)C₀-C₆alkylOR⁶, haloC₁-C₆alkyl, —C₀-C₆alkylOR⁶ and (=O), wherein each of the foregoing is optionally substituted with R⁷.

7. A compound according to claim 1, wherein Z¹ is C.

8. A compound according to claim 1, wherein Z² is CRᵃ.

9. A compound according to claim 1, wherein Z³ is N.

10. A compound according to claim 1, wherein R¹ is a heteroaryl group of Formula A1:

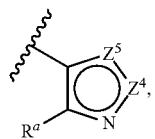

[A1]

wherein Rᵃ, Z⁴ and Z⁵ are as defined in claim 1.

11. A compound according to claim 1, wherein R¹ is a heteroaryl group of formula A2:

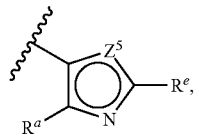

[A2]

wherein Rᵃ, Rᵉ and Z⁵ are as defined in claim 1.

12. A compound according to claim 1, wherein R¹ is a heteroaryl group of formula A3:

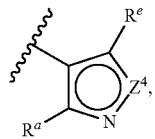

[A3]

wherein Rᵃ, Rᵉ and Z⁴ are as defined in claim 1.

13. A compound according to claim 1, wherein R¹ is selected from:

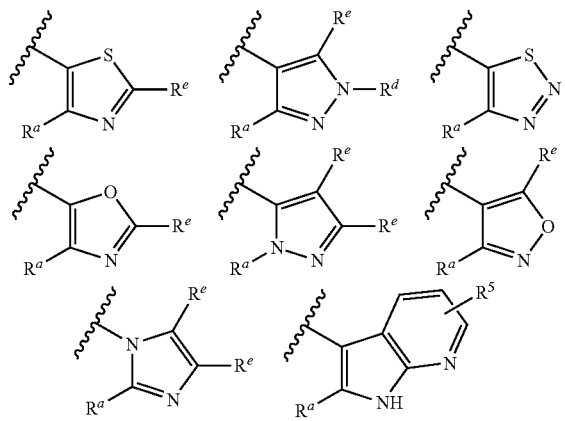

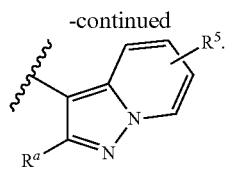

14. A compound according to claim 1, wherein Rᵃ is selected from hydrogen, hydroxyl, halogen, C₁-C₃alkyl, —OCN, —SCN, —CN, and haloC₁-C₃alkyl.

15. A compound according to claim 1, wherein Rᵇ is selected from hydrogen, hydroxyl, halogen, C₁-C₃alkyl, —OCN, —SCN, —CN and haloC₁-C₃alkyl.

16. A compound according to claim 1, wherein Rᵇ is selected from hydrogen and methyl.

17. A compound according to claim 1, wherein R¹ is selected from:

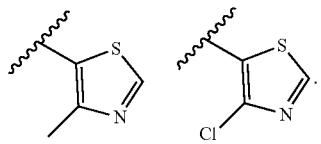

18. A compound according to claim 1 selected from the group consisting of:
tert-butyl 4-[5-chloro-2-(4-methylthiazol-5-yl)-6-oxo-1H-pyrimidin-4-yl]piperidine-1-carboxylate;
5-chloro-2-(4-methylthiazol-5-yl)-4-(4-piperidyl)-1H-pyrimidin-6-one;
5-chloro-4-[1-(2,2-difluorocyclopropanecarbonyl)-4-piperidyl]-2-(4-methylthiazol-5-yl)-1H-pyrimidin-6-one;
5-chloro-4-[1-(4-methylthiazole-5-carbonyl)-4-piperidyl]-2-(4-methylthiazol-5-yl)-1H-pyrimidin-6-one;
5-chloro-2-(4-methylthiazol-5-yl)-4-[1-(thiazole-4-carbonyl)-4-piperidyl]-1H-pyrimidin-6-one;
5-chloro-4-[1-(3-methyl-1H-pyrazole-5-carbonyl)-4-piperidyl]-2-(4-methylthiazol-5-yl)-1H-pyrimidin-6-one;
5-chloro-4-[1-(1,5-dimethylpyrazole-3-carbonyl)-4-piperidyl]-2-(4-methylthiazol-5-yl)-1H-pyrimidin-6-one;
5-chloro-4-[1-(2,5-dimethylpyrazole-3-carbonyl)-4-piperidyl]-2-(4-methylthiazol-5-yl)-1H-pyrimidin-6-one;
5-chloro-4-[1-(5-methylisoxazole-3-carbonyl)-4-piperidyl]-2-(4-methylthiazol-5-yl)-1H-pyrimidin-6-one;
5-chloro-2-(4-methylthiazol-5-yl)-4-[1-(pyridazine-4-carbonyl)-4-piperidyl]-1H-pyrimidin-6-one;
5-chloro-4-(1-isobutyl-4-piperidyl)-2-(4-methylthiazol-5-yl)-1H-pyrimidin-6-one;
5-chloro-2-(4-methylthiazol-5-yl)-4-tetrahydropyran-4-yl-1H-pyrimidin-6-one;
5-chloro-2-(5-ethyl-1H-pyrazol-4-yl)-4-tetrahydropyran-4-yl-1H-pyrimidin-6-one;
5-chloro-4-tetrahydropyran-4-yl-2-thiazol-5-yl-1H-pyrimidin-6-one;
5-chloro-2-(4-methylthiadiazol-5-yl)-4-tetrahydropyran-4-yl-1H-pyrimidin-6-one;
5-chloro-2-(4-methyloxazol-5-yl)-4-tetrahydropyran-4-yl-1H-pyrimidin-6-one;
5-fluoro-2-(4-methylthiazol-5-yl)-4-tetrahydropyran-4-yl-1H-pyrimidin-6-one;
5-bromo-2-(4-methylthiazol-5-yl)-4-tetrahydropyran-4-yl-1H-pyrimidin-6-one;
5-iodo-2-(4-methylthiazol-5-yl)-4-tetrahydropyran-4-yl-1H-pyrimidin-6-one;

2-(4-methylthiazol-5-yl)-6-oxo-4-tetrahydropyran-4-yl-1H-pyrimidine-5-carbonitrile;
5-chloro-2-(2-hydroxy-4-methyl-thiazol-5-yl)-4-tetrahydropyran-4-yl-1H-pyrimidin-6-one;
5-chloro-4-(4-hydroxy-1-piperidyl)-2-(4-methylthiazol-5-yl)-1H-pyrimidin-6-one;
5-chloro-4-(4-methyl-1-piperidyl)-2-(4-methylthiazol-5-yl)-1H-pyrimidin-6-one;
5-chloro-2-(4-methylthiazol-5-yl)-4-[3-(trifluoromethyl)piperazin-1-yl]-1H-pyrimidin-6-one;
5-chloro-4-[(3-methylpiperazin-1-yl]-2-(4-methylthiazol-5-yl)-1H-pyrimidin-6-one;
5-chloro-4-[(3R)-3-methylpiperazin-1-yl]-2-(4-methylthiazol-5-yl)-1H-pyrimidin-6-one;
5-chloro-4-[4-(hydroxymethyl)-1-piperidyl]-2-(4-methylthiazol-5-yl)-1H-pyrimidin-6-one;
4-[5-chloro-2-(4-methylthiazol-5-yl)-6-oxo-1H-pyrimidin-4-yl]-1,4-diazepan-2-one;
5-chloro-4-(3,3-difluoro-1-piperidyl)-2-(4-methylthiazol-5-yl)-1H-pyrimidin-6-one;
5-chloro-4-[3-(hydroxymethyl)-1-piperidyl]-2-(4-methylthiazol-5-yl)-1H-pyrimidin-6-one;
5-chloro-4-[(3S)-3-methylpiperazin-1-yl]-2-(4-methylthiazol-5-yl)-1H-pyrimidin-6-one;
5-chloro-2-(4-methylthiazol-5-yl)-4-piperazin-1-yl-1H-pyrimidin-6-one;
5-chloro-2-(4-ethylthiazol-5-yl)-4-tetrahydropyran-4-yl-1H-pyrimidin-6-one;
5-chloro-2-(3-methyl-1H-pyrazol-4-yl)-4-tetrahydropyran-4-yl-1H-pyrimidin-6-one;
5-chloro-2-(4-methylthiazol-5-yl)-4-[3-(trifluoromethyl)piperazin-1-yl]-1H-pyrimidin-6-one;
5-chloro-2-(4-methylthiazol-5-yl)-4-[(3R)-3-(trifluoromethyl)piperazin-1-yl]-1H-pyrimidin-6-one;
5-chloro-2-(4-chlorothiazol-5-yl)-4-tetrahydropyran-4-yl-1H-pyrimidin-6-one;
5-chloro-4-tetrahydropyran-4-yl-2-[4-(trifluoromethyl)thiazol-5-yl]-1H-pyrimidin-6-one;
5-chloro-4-[3-isopropylpiperazin-1-yl]-2-(4-methylthiazol-5-yl)-1H-pyrimidin-6-one;
5-chloro-4-[(3S)-3-isopropylpiperazin-1-yl]-2-(4-methylthiazol-5-yl)-1H-pyrimidin-6-one;
5-chloro-4-tetrahydropyran-4-yl-2-[5-(trifluoromethyl)-1H-pyrazol-4-yl]-1H-pyrimidin-6-one;
5-chloro-2-(2-methylpyrazol-3-yl)-4-tetrahydropyran-4-yl-1H-pyrimidin-6-one;
5-chloro-2-(5-methyl-1H-pyrazol-4-yl)-4-morpholino-1H-pyrimidin-6-one;
5-chloro-4-morpholino-2-[5-(trifluoromethyl)-1H-pyrazol-4-yl]-1H-pyrimidin-6-one;
5-chloro-4-[2-methylpiperazin-1-yl]-2-(5-methyl-1H-pyrazol-4-yl)-1H-pyrimidin-6-one;
5-chloro-4-[(2R)-2-methylpiperazin-1-yl]-2-(5-methyl-1H-pyrazol-4-yl)-1H-pyrimidin-6-one;
5-chloro-4-[3-methylmorpholin-4-yl]-2-(1H-pyrrolo[2,3-b]pyridin-3-yl)-1H-pyrimidin-6-one;
5-chloro-4-[(3R)-3-methylmorpholin-4-yl]-2-(1H-pyrrolo[2,3-b]pyridin-3-yl)-1H-pyrimidin-6-one;
5-chloro-4-[3-methylmorpholin-4-yl]-2-[5-(trifluoromethyl)-1H-pyrazol-4-yl]-1H-pyrimidin-6-one;
5-chloro-4-[(3R)-3-methylmorpholin-4-yl]-2-[5-(trifluoromethyl)-1H-pyrazol-4-yl]-1H-pyrimidin-6-one;
5-chloro-4-[2-methylpiperazin-1-yl]-2-[5-(trifluoromethyl)-1H-pyrazol-4-yl]-1H-pyrimidin-6-one;
5-chloro-4-[(2R)-2-methylpiperazin-1-yl]-2-[5-(trifluoromethyl)-1H-pyrazol-4-yl]-1H-pyrimidin-6-one;
5-chloro-4-[3-methylmorpholin-4-yl]-2-pyrazolo[1,5-a]pyridin-3-yl-1H-pyrimidin-6-one;
5-chloro-4-[(3R)-3-methylmorpholin-4-yl]-2-pyrazolo[1,5-a]pyridin-3-yl-1H-pyrimidin-6-one;
5-chloro-4-[2-methylpiperazin-1-yl]-2-(1H-pyrrolo[2,3-b]pyridin-3-yl)-1H-pyrimidin-6-one;
5-chloro-4-[(2R)-2-methylpiperazin-1-yl]-2-(1H-pyrrolo[2,3-b]pyridin-3-yl)-1H-pyrimidin-6-one;
5-chloro-4-(6,6-difluoro-1,4-diazepan-1-yl)-2-[5-(trifluoromethyl)-1H-pyrazol-4-yl]-1H-pyrimidin-6-one;
5-chloro-2-(5-chloro-1H-pyrazol-4-yl)-4-[(2R)-2-methylpiperazin-1-yl]-1H-pyrimidin-6-one;
5-chloro-4-(6,6-difluoro-1,4-diazepan-1-yl)-2-(1H-pyrrolo[2,3-b]pyridin-3-yl)-1H-pyrimidin-6-one;
5-chloro-4-(2,2-dimethylpiperazin-1-yl)-2-[5-(trifluoromethyl)-1H-pyrazol-4-yl]-1H-pyrimidin-6-one;
5-chloro-4-[2-methylpiperazin-1-yl]-2-(4-methylthiazol-5-yl)-1H-pyrimidin-6-one;
5-chloro-4-[(2R)-2-methylpiperazin-1-yl]-2-(4-methylthiazol-5-yl)-1H-pyrimidin-6-one;
5-chloro-2-(3-methylisoxazol-4-yl)-4-[(2R)-2-methylpiperazin-1-yl]-1H-pyrimidin-6-one;
5-chloro-4-[3-methylmorpholin-4-yl]-2-(4-methylthiazol-5-yl)-1H-pyrimidin-6-one;
5-chloro-4-[(3R)-3-methylmorpholin-4-yl]-2-(4-methylthiazol-5-yl)-1H-pyrimidin-6-one;
5-chloro-4-(6,6-difluoro-1,4-diazepan-1-yl)-2-(4-methylthiazol-5-yl)-1H-pyrimidin-6-one;
5-chloro-2-(5-chloro-1H-pyrazol-4-yl)-4-[3-methylmorpholin-4-yl]-1H-pyrimidin-6-one;
5-chloro-2-(5-chloro-1H-pyrazol-4-yl)-4-[(3R)-3-methylmorpholin-4-yl]-1H-pyrimidin-6-one;
5-chloro-2-(4-methylthiazol-5-yl)-4-[2-(trifluoromethyl)piperazin-1-yl]-1H-pyrimidin-6-one;
5-chloro-4-[2-(difluoromethyl)piperazin-1-yl]-2-(4-methylthiazol-5-yl)-1H-pyrimidin-6-one;
5-chloro-4-(6-fluoro-1,4-diazepan-1-yl)-2-(4-methylthiazol-5-yl)-1H-pyrimidin-6-one;
5-chloro-2-(4-chlorothiazol-5-yl)-4-[2-methylpiperazin-1-yl]-1H-pyrimidin-6-one;
5-chloro-2-(4-chlorothiazol-5-yl)-4-[(2R)-2-methylpiperazin-1-yl]-1H-pyrimidin-6-one;
5-chloro-4-[2-methylpiperazin-1-yl]-2-(2-methylpyrazol-3-yl)-1H-pyrimidin-6-one;
5-chloro-4-[(2R)-2-methylpiperazin-1-yl]-2-(2-methylpyrazol-3-yl)-1H-pyrimidin-6-one;
5-chloro-2-(4-chlorothiazol-5-yl)-4-[3-methylmorpholin-4-yl]-1H-pyrimidin-6-one;
5-chloro-2-(4-chlorothiazol-5-yl)-4-[(3R)-3-methylmorpholin-4-yl]-1H-pyrimidin-6-one;
5-chloro-2-(4-chlorothiazol-5-yl)-4-(6,6-difluoro-1,4-diazepan-1-yl)-1H-pyrimidin-6-one;
5-chloro-2-(2-methylimidazol-1-yl)-4-[3-methylmorpholin-4-yl]-1H-pyrimidin-6-one;
5-chloro-2-(2-methylimidazol-1-yl)-4-[(3R)-3-methylmorpholin-4-yl]-1H-pyrimidin-6-one;
5-chloro-2-(5-chloro-1H-pyrazol-4-yl)-4-(6,6-difluoro-1,4-diazepan-1-yl)-1H-pyrimidin-6-one;
5-chloro-4-(6,6-difluoro-1,4-diazepan-1-yl)-2-[4-(trifluoromethyl)thiazol-5-yl]-1H-pyrimidin-6-one;
5-chloro-2-(4-chlorothiazol-5-yl)-4-[2-(difluoromethyl)piperazin-1-yl]-1H-pyrimidin-6-one;
5-chloro-2-(4-chlorothiazol-5-yl)-4-[2-(trifluoromethyl)piperazin-1-yl]-1H-pyrimidin-6-one;
5-chloro-2-(4-chlorothiazol-5-yl)-4-(6-fluoro-1,4-diazepan-1-yl)-1H-pyrimidin-6-one;

5-chloro-2-(4-chlorothiazol-5-yl)-4-[2-(difluoromethyl)piperazin-1-yl]-1H-pyrimidin-6-one;

5-chloro-2-(4-chlorothiazol-5-yl)-4-[(2S)-2-(difluoromethyl)piperazin-1-yl]-1H-pyrimidin-6-one;

5-chloro-2-(4-chlorothiazol-5-yl)-4-[(2R)-R-(difluoromethyl)piperazin-1-yl]-1H-pyrimidin-6-one;

5-chloro-2-(4-chlorothiazol-5-yl)-4-[6-fluoro-1,4-diazepan-1-yl]-1H-pyrimidin-6-one;

5-chloro-2-(4-chlorothiazol-5-yl)-4-[(6S)-6-fluoro-1,4-diazepan-1-yl]-1H-pyrimidin-6-one;

5-chloro-2-(4-chlorothiazol-5-yl)-4-[(6R)-6-fluoro-1,4-diazepan-1-yl]-1H-pyrimidin-6-one, or a salt or solvate thereof.

19. A pharmaceutical composition comprising a compound according to claim 1, or a pharmaceutically acceptable salt or solvate thereof, in admixture with a pharmaceutically acceptable diluent or carrier.

20. A combination comprising a compound, or a pharmaceutically acceptable salt or solvate thereof, as defined in of claim 1, with one or more additional therapeutic agents.

* * * * *